US00RE38916E

(19) United States
(12) Reissued Patent
Vogelstein et al.

(10) Patent Number: US RE38,916 E
(45) Date of Reissued Patent: Dec. 6, 2005

(54) APC ANTIBODIES

(75) Inventors: Bert Vogelstein, Baltimore, MD (US); Kenneth W. Kinzler, Bel Air, MD (US); Hans Albertsen, Salt Lake City, UT (US); Rakesh Anand, Chelford (GB); Mary Carlson, Salt Lake City, UT (US); Joanna Groden, Cincinnati, OH (US); Philip John Hedge, Goostrey (GB); Geoff Joslyn, Fremont, CA (US); Alexander Fred Markham, Crewe (GB); Yusuka Nakamura, Tokyo (JP); Andrew Thilveris, Madison, WI (US); Raymond L. White, Tiburon, CA (US)

(73) Assignees: The Johns Hopkins University, Baltimore, MD (US); The University of Utah, Salt Lake City, UT (US); The Cancer Institute, Tokyo (JP); Zeneca Limited, London (GB)

(21) Appl. No.: 09/442,489

(22) Filed: Nov. 18, 1999

Related U.S. Patent Documents

Reissue of:
(64) Patent No.: 5,691,454
Issued: Nov. 25, 1997
Appl. No.: 08/452,654
Filed: May 25, 1995

U.S. Applications:
(62) Division of application No. 08/289,548, filed on Aug. 12, 1994, now Pat. No. 5,648,212, which is a division of application No. 07/741,940, filed on Aug. 8, 1991, now Pat. No. 5,352,775.

(30) Foreign Application Priority Data

Jan. 16, 1991 (GB) ..... 9100962
Jan. 16, 1991 (GB) ..... 9100963
Jan. 16, 1991 (GB) ..... 9100974
Jan. 16, 1991 (GB) ..... 9100975

(51) Int. Cl.[7] ..... C07K 16/32; C12N 5/12; C12N 15/12

(52) U.S. Cl. ..... 530/387.7; 530/388.2; 530/387.9; 530/388.8; 530/389.7; 536/23.5; 424/130.1; 424/138.1; 424/141.1; 424/174.1

(58) Field of Search ..... 530/388.2, 387.9, 530/387.7, 388.8, 389.7, 806, 827, 843, 844, 387.1; 536/23.5; 424/130.1, 138.1, 141.1, 174.1; 435/240.27

(56) References Cited

U.S. PATENT DOCUMENTS 5,098,823 A 3/1992 Bodmer et al.
5,137,806 A * 8/1992 LeMaistre et al.
5,244,801 A * 9/1993 Tobi

FOREIGN PATENT DOCUMENTS

WO WO 89/01481 * 8/1988

OTHER PUBLICATIONS

Kinzler et al., "Identification of FAP Locus Genes from Chromosome 5q21", Science 253: 661–665, 1991.*

Groden et al., "Identification and Characterization of the familial Adenomatous Polyposis Coli Gene", Cell 66:589–600 (1991).*

Joslyn et al. "Identification of Deletion Mutations and Three New Genes at the Familial Polyposis Locus" Cell, 66:601–613 (1991).*

Nishisho et al., "Mutations of Chromosome 5q21 Genes in FAP and Colorectal Cancer Patients" Science, 253:665–669 (1991).*

Orita et al., Genomics, vol. 5, pp. 874–879, 1989.*

Stanbridge et al., "Identifying Tumor Suppressor Genes in Human Colorectal Cancer", Science 247:12–13 (1990).*

Fearon et al., "Identification of a Chromosome 18q Gene that is Altered in Colorectal Cancer" Science 247:49–56 (1990).*

Baker et al., "Chromosome 17 Deletions and p53 Gene Mutations in Colorectal Carcinomas", Science, 244:217–221 (1989).*

Bodmer et al. "Localization of the Gene for familial Adenomatous Polyposis of Chromosome 5" Nature 328:614–616 (1987).*

* cited by examiner

*Primary Examiner*—Christina Chan
*Assistant Examiner*—F. Pierre VanderVegt
(74) *Attorney, Agent, or Firm*—Banner & Witcoff

(57) ABSTRACT

A human gene termed APC is disclosed. Methods and kits are provided for assessing mutations of the APC gene in human tissues and body samples. APC mutations are found in familial adenomatous polyposis patients as well as in sporadic colorectal cancer patients. APC is expressed in most normal tissues. These results suggest that APC is a tumor suppressor.

1 Claim, 40 Drawing Sheets

FIG. 2A

TB1 Amino Acid Sequence

VAPVVVGSGR APRHPAPAAM HPRRPDGFDG LGYRGGARDE QGFGGAFPAR SFSTGSDLGH 60

WVTTPPDIPG SRNLHWGEKS PPYGVPTTST PYEGPTEEPF SSGGGGSVQG QSSEQLNRFA 120

GFGIGLASLF TENVLAHPCI VLRRQCQVNY HAQHYHLTPF TVINIMYSFN KTQGPRALWK 180

GMGSTFIVQG VTLGAEGIIS EFTPLPREVL HKWSPKQIGE HLLLKSLTYV VAMPFYSASL 240

IETVQSEIIR DNTGILECVK EGIGRVIGMG VPHSKRLLPL LSLIFPTVLH GVLHYIISSV 300

IQKFVLLILK RKTYNSHLAE STSPVQSMLD AYFPELIANF AASLCSDVIL YPLETVLHRL 360

HIQGTRTIID NTDLGYEVLP INTQYEGMRD CINTIRQEEG VFGFYKGFGA VIIQYTLHAA 420

VLQITKIIYS TLLQ 434

FIG. 2B

TB2 Amino Acid Sequence

ELRRFDRFLH EKNCMTDLLA KLEAKTGVNR SFIALGVIGL VALYLVFGYG ASLLCNLIGF 60

GYPAYISIKA IESPNKEDDT QWLTYWVVYG VFSIAEFFSD IFLSWFPFYY ILKCGFLLWC 120

MAPSPSNGAE LLYKRIIRPF FLKHESQMDS VVKDLKDKAK ETADAITKEA KKATVNLLGE 180

EKKST 185

FIG. 3A

Met Ala Ala Ala Ser Tyr Asp Gln Leu Leu Lys Gln Val Glu Ala Leu
1 5 10 15

Lys Met Glu Asn Ser Asn Leu Arg Gln Glu Leu Glu Asp Asn Ser Asn
20 25 30

His Leu Thr Lys Leu Glu Thr Glu Ala Ser Asn Met Lys Glu Val Leu
35 40 45

Lys Gln Leu Gln Gly Ser Ile Glu Asp Glu Ala Met Ala Ser Ser Gly
50 55 60

Gln Ile Asp Leu Leu Glu Arg Leu Lys Glu Leu Asn Leu Asp Ser Ser
65 70 75 80

Asn Phe Pro Gly Val Lys Leu Arg Ser Lys Met Ser Leu Arg Ser Tyr
85 90 95

Gly Ser Arg Glu Gly Ser Val Ser Ser Arg Ser Gly Glu Cys Ser Pro
100 105 110

FIG. 3B

Val Pro Met Gly Ser Phe Pro Arg Arg Gly Phe Val Asn Gly Ser Arg
115 120 125

Glu Ser Thr Gly Tyr Leu Glu Glu Leu Glu Lys Glu Arg Ser Leu Leu
130 135 140

Leu Ala Asp Leu Asp Lys Glu Glu Lys Glu Lys Asp Trp Tyr Tyr Ala
145 150 155 160

Gln Leu Gln Asn Leu Thr Lys Arg Ile Asp Ser Leu Pro Leu Thr Glu
165 170 175

Asn Phe Ser Leu Gln Thr Asp Leu Thr Arg Arg Gln Leu Glu Tyr Glu
180 185 190

Ala Arg Gln Ile Arg Val Ala Met Glu Glu Gln Leu Gly Thr Cys Gln
195 200 205

Asp Met Glu Lys Arg Ala Gln Arg Arg Ile Ala Arg Ile Gln Gln Ile
210 215 220

FIG. 3C

Glu Lys Asp Ile Leu Arg Ile Arg Gln Leu Leu Gln Ser Gln Ala Thr
225 230 235 240

Glu Ala Glu Arg Ser Ser Gln Asn Lys His Glu Thr Gly Ser His Asp
245 250 255

Ala Glu Arg Gln Asn Glu Gly Gln Gly Val Gly Glu Ile Asn Met Ala
260 265 270

Thr Ser Gly Asn Gly Gln Gly Ser Thr Thr Arg Met Asp His Glu Thr
275 280 285

Ala Ser Val Leu Ser Ser Ser Ser Thr His Ser Ala Pro Arg Arg Leu
290 295 300

Thr Ser His Leu Gly Thr Lys Val Glu Met Val Tyr Ser Leu Leu Ser
305 310 315 320

Met Leu Gly Thr His Asp Lys Asp Asp Met Ser Arg Thr Leu Leu Ala
325 330 335

FIG. 3D

Met Ser Ser Ser Gln Asp Ser Cys Ile Ser Met Arg Gln Ser Gly Cys
340 345 350

Leu Pro Leu Leu Ile Gln Leu Leu His Gly Asn Asp Lys Asp Ser Val
355 360 365

Leu Leu Gly Asn Ser Arg Gly Ser Lys Glu Ala Arg Ala Arg Ala Ser
370 375 380

Ala Ala Leu His Asn Ile Ile His Ser Gln Pro Asp Asp Lys Arg Gly
385 390 395 400

Arg Arg Glu Ile Arg Val Leu His Leu Leu Glu Gln Ile Arg Ala Tyr
405 410 415

Cys Glu Thr Cys Trp Glu Trp Gln Glu Ala His Glu Pro Gly Met Asp
420 425 430

Gln Asp Lys Asn Pro Met Pro Ala Pro Val Glu His Gln Ile Cys Pro
435 440 445

FIG. 3E

Ala Val Cys Val Leu Met Lys Leu Ser Phe Asp Glu Glu His Arg His
450 455 460

Ala Met Asn Glu Leu Gly Gly Leu Gln Ala Ile Ala Glu Leu Leu Gln
465 470 475 480

Val Asp Cys Glu Met Tyr Gly Leu Thr Asn Asp His Tyr Ser Ile Thr
485 490 495

Leu Arg Arg Tyr Ala Gly Met Ala Leu Thr Asn Leu Thr Phe Gly Asp
500 505 510

Val Ala Asn Lys Ala Thr Leu Cys Ser Met Lys Gly Cys Met Arg Ala
515 520 525

Leu Val Ala Gln Leu Lys Ser Glu Ser Glu Asp Leu Gln Gln Val Ile
530 535 540

Ala Ser Val Leu Arg Asn Leu Ser Trp Arg Ala Asp Val Asn Ser Lys
545 550 555 560

FIG. 3F

Lys Thr Leu Arg Glu Val Gly Ser Val Lys Ala Leu Met Glu Cys Ala
565 570 575

Leu Glu Val Lys Lys Glu Ser Thr Leu Lys Ser Val Leu Ser Ala Leu
580 585 590

Trp Asn Leu Ser Ala His Cys Thr Glu Asn Lys Ala Asp Ile Cys Ala
595 600 605

Val Asp Gly Ala Leu Ala Phe Leu Val Gly Thr Leu Thr Tyr Arg Ser
610 615 620

Gln Thr Asn Thr Leu Ala Ile Ile Glu Ser Gly Gly Gly Ile Leu Arg
625 630 635 640

Asn Val Ser Ser Leu Ile Ala Thr Asn Glu Asp His Arg Gln Ile Leu
645 650 655

Arg Glu Asn Asn Cys Leu Gln Thr Leu Leu Gln His Leu Lys Ser His
660 665 670

FIG. 3G

Ser Leu Thr Ile Val Ser Asn Ala Cys Gly Thr Leu Trp Asn Leu Ser
675 680 685

Ala Arg Asn Pro Lys Asp Gln Glu Ala Leu Trp Asp Met Gly Ala Val
690 695 700

Ser Met Leu Lys Asn Leu Ile His Ser Lys His Lys Met Ile Ala Met
705 710 715 720

Gly Ser Ala Ala Ala Leu Arg Asn Leu Met Ala Asn Arg Pro Ala Lys
725 730 735

Tyr Lys Asp Ala Asn Ile Met Ser Pro Gly Ser Ser Leu Pro Ser Leu
740 745 750

His Val Arg Lys Gln Lys Ala Leu Glu Ala Glu Leu Asp Ala Gln His
755 760 765

Leu Ser Glu Thr Phe Asp Asn Ile Asp Asn Leu Ser Pro Lys Ala Ser
770 775 780

FIG. 3H

His Arg Ser Lys Gln Arg His Lys Gln Ser Leu Tyr Gly Asp Tyr Val
785 790 795 800

Phe Asp Thr Asn Arg His Asp Asp Asn Arg Ser Asp Asn Phe Asn Thr
805 810 815

Gly Asn Met Thr Val Leu Ser Pro Tyr Leu Asn Thr Thr Val Leu Pro
820 825 830

Ser Ser Ser Ser Ser Arg Gly Ser Leu Asp Ser Ser Arg Ser Glu Lys
835 840 845

Asp Arg Ser Leu Glu Arg Glu Arg Gly Ile Gly Leu Gly Asn Tyr His
850 855 860

Pro Ala Thr Glu Asn Pro Gly Thr Ser Ser Lys Arg Gly Leu Gln Ile
865 870 875 880

Ser Thr Thr Ala Ala Gln Ile Ala Lys Val Met Glu Glu Val Ser Ala
885 890 895

FIG. 3I

Ile His Thr Ser Gln Glu Asp Arg Ser Ser Gly Ser Thr Thr Glu Leu
900 905 910

His Cys Val Thr Asp Glu Arg Asn Ala Leu Arg Arg Ser Ser Ala Ala
915 920 925

His Thr His Ser Asn Thr Tyr Asn Phe Thr Lys Ser Glu Asn Ser Asn
930 935 940

Arg Thr Cys Ser Met Pro Tyr Ala Lys Leu Glu Tyr Lys Arg Ser Ser
945 950 955 960

Asn Asp Ser Leu Asn Ser Val Ser Ser Asn Asp Gly Tyr Gly Lys Arg
965 970 975

Gly Gln Met Lys Pro Ser Ile Glu Ser Tyr Ser Glu Asp Asp Glu Ser
980 985 990

Lys Phe Cys Ser Tyr Gly Gln Tyr Pro Ala Asp Leu Ala His Lys Ile
995 1000 1005

FIG. 3J

His Ser Ala Asn His Met Asp Asp Asn Asp Gly Glu Leu Asp Thr Pro
1010 1015 1020

Ile Asn Tyr Ser Leu Lys Tyr Ser Asp Glu Gln Leu Asn Ser Gly Arg
1025 1030 1035 1040

Gln Ser Pro Ser Gln Asn Glu Arg Trp Ala Arg Pro Lys His Ile Ile
1045 1050 1055

Glu Asp Glu Ile Lys Gln Ser Glu Gln Arg Gln Ser Arg Asn Gln Ser
1060 1065 1070

Thr Thr Tyr Pro Val Tyr Thr Glu Ser Thr Asp Asp Lys His Leu Lys
1075 1080 1085

Phe Gln Pro His Phe Gly Gln Gln Glu Cys Val Ser Pro Tyr Arg Ser
1090 1095 1100

Arg Gly Ala Asn Gly Ser Glu Thr Asn Arg Val Gly Ser Asn His Gly
1105 1110 1115 1120

FIG. 3K

Ile Asn Gln Asn Val Ser Gln Ser Leu Cys Gln Glu Asp Asp Tyr Glu
1125 1130 1135

Asp Asp Lys Pro Thr Asn Tyr Ser Glu Arg Tyr Ser Glu Glu Glu Gln
1140 1145 1150

His Glu Glu Glu Glu Arg Pro Thr Asn Tyr Ser Ile Lys Tyr Asn Glu
1155 1160 1165

Glu Lys Arg His Val Asp Gln Pro Ile Asp Tyr Ser Leu Lys Tyr Ala
1170 1175 1180

Thr Asp Ile Pro Ser Ser Gln Lys Gln Ser Phe Ser Phe Ser Lys Ser
1185 1190 1195 1200

Ser Ser Gly Gln Ser Ser Lys Thr Glu His Met Ser Ser Ser Ser Glu
1205 1210 1215

Asn Thr Ser Thr Pro Ser Ser Asn Ala Lys Arg Gln Asn Gln Leu His
1220 1225 1230

FIG. 3L

Pro Ser Ser Ala Gln Ser Arg Ser Gly Gln Pro Gln Lys Ala Ala Thr
1235 1240 1245

Cys Lys Val Ser Ser Ile Asn Gln Glu Thr Ile Gln Thr Tyr Cys Val
1250 1255 1260

Glu Asp Thr Pro Ile Cys Phe Ser Arg Cys Ser Ser Leu Ser Ser Leu
1265 1270 1275 1280

Ser Ser Ala Glu Asp Glu Ile Gly Cys Asn Gln Thr Thr Gln Glu Ala
1285 1290 1295

Asp Ser Ala Asn Thr Leu Gln Ile Ala Glu Ile Lys Gly Lys Ile Gly
1300 1305 1310

Thr Arg Ser Ala Glu Asp Pro Val Ser Glu Val Pro Ala Val Ser Gln
1315 1320 1325

His Pro Arg Thr Lys Ser Ser Arg Leu Gln Gly Ser Ser Leu Ser Ser
1330 1335 1340

FIG. 3M

Glu Ser Ala Arg His Lys Ala Val Glu Phe Pro Ser Gly Ala Lys Ser
1345 1350 1355 1360

Pro Ser Lys Ser Gly Ala Gln Thr Pro Lys Ser Pro Pro Glu His Tyr
1365 1370 1375

Val Gln Glu Thr Pro Leu Met Phe Ser Arg Cys Thr Ser Val Ser Ser
1380 1385 1390

Leu Asp Ser Phe Glu Ser Arg Ser Ile Ala Ser Ser Val Gln Ser Glu
1395 1400 1405

Pro Cys Ser Gly Met Val Ser Gly Ile Ile Ser Pro Ser Asp Leu Pro
1410 1415 1420

Asp Ser Pro Gly Gln Thr Met Pro Pro Ser Arg Ser Lys Thr Pro Pro
1425 1430 1435 1440

Pro Pro Pro Gln Thr Ala Gln Thr Lys Arg Glu Val Pro Lys Asn Lys
1445 1450 1455

FIG. 3N

Ala Pro Thr Ala Glu Lys Arg Glu Ser Gly Pro Lys Gln Ala Ala Val
1460 1465 1470

Asn Ala Ala Val Gln Arg Val Gln Val Leu Pro Asp Ala Asp Thr Leu
1475 1480 1485

Leu His Phe Ala Thr Glu Ser Thr Pro Asp Gly Phe Ser Cys Ser Ser
1490 1495 1500

Ser Leu Ser Ala Leu Ser Leu Asp Glu Pro Phe Ile Gln Lys Asp Val
1505 1510 1515 1520

Glu Leu Arg Ile Met Pro Pro Val Gln Glu Asn Asp Asn Gly Asn Glu
1525 1530 1535

Thr Glu Ser Glu Gln Pro Lys Glu Ser Asn Glu Asn Gln Glu Lys Glu
1540 1545 1550

Ala Glu Lys Thr Ile Asp Ser Glu Lys Asp Leu Leu Asp Asp Ser Asp
1555 1560 1565

FIG. 3O

Asp Asp Asp Ile Glu Ile Leu Glu Glu Cys Ile Ile Ser Ala Met Pro
1570 1575 1580

Thr Lys Ser Ser Arg Lys Gly Lys Lys Pro Ala Gln Thr Ala Ser Lys
1585 1590 1595 1600

Leu Pro Pro Pro Val Ala Arg Lys Pro Ser Gln Leu Pro Val Tyr Lys
1605 1610 1615

Leu Leu Pro Ser Gln Asn Arg Leu Gln Pro Gln Lys His Val Ser Phe
1620 1625 1630

Thr Pro Gly Asp Asp Met Pro Arg Val Tyr Cys Val Glu Gly Thr Pro
1635 1640 1645

Ile Asn Phe Ser Thr Ala Thr Ser Leu Ser Asp Leu Thr Ile Glu Ser
1650 1655 1660

Pro Pro Asn Glu Leu Ala Ala Gly Glu Gly Val Arg Gly Gly Ala Gln
1665 1670 1675 1680

FIG. 3P

Ser Gly Glu Phe Glu Lys Arg Asp Thr Ile Pro Thr Glu Gly Arg Ser
1685 1690 1695

Thr Asp Glu Ala Gln Gly Gly Lys Thr Ser Ser Val Thr Ile Pro Glu
1700 1705 1710

Leu Asp Asp Asn Lys Ala Glu Glu Gly Asp Ile Leu Ala Glu Cys Ile
1715 1720 1725

Asn Ser Ala Met Pro Lys Gly Lys Ser His Lys Pro Phe Arg Val Lys
1730 1735 1740

Lys Ile Met Asp Gln Val Gln Gln Ala Ser Ala Ser Ser Ser Ala Pro
1745 1750 1755 1760

Asn Lys Asn Gln Leu Asp Gly Lys Lys Lys Lys Pro Thr Ser Pro Val
1765 1770 1775

Lys Pro Ile Pro Gln Asn Thr Glu Tyr Arg Thr Arg Val Arg Lys Asn
1780 1785 1790

FIG. 3Q

Ala Asp Ser Lys Asn Asn Leu Asn Ala Glu Arg Val Phe Ser Asp Asn
1795 1800 1805

Lys Asp Ser Lys Lys Gln Asn Leu Lys Asn Asn Ser Lys Asp Phe Asn
1810 1815 1820

Asp Lys Leu Pro Asn Asn Glu Asp Arg Val Arg Gly Ser Phe Ala Phe
1825 1830 1835 1840

Asp Ser Pro His His Tyr Thr Pro Ile Glu Gly Thr Pro Tyr Cys Phe
1845 1850 1855

Ser Arg Asn Asp Ser Leu Ser Ser Leu Asp Phe Asp Asp Asp Asp Val
1860 1865 1870

Asp Leu Ser Arg Glu Lys Ala Glu Leu Arg Lys Ala Lys Glu Asn Lys
1875 1880 1885

Glu Ser Glu Ala Lys Val Thr Ser His Thr Glu Leu Thr Ser Asn Gln
1890 1895 1900

FIG. 3R

Gln Ser Ala Asn Lys Thr Gln Ala Ile Ala Lys Gln Pro Ile Asn Arg
1905 1910 1915 1920

Gly Gln Pro Lys Pro Ile Leu Gln Lys Gln Ser Thr Phe Pro Gln Ser
1925 1930 1935

Ser Lys Asp Ile Pro Asp Arg Gly Ala Ala Thr Asp Glu Lys Leu Gln
1940 1945 1950

Asn Phe Ala Ile Glu Asn Thr Pro Val Cys Phe Ser His Asn Ser Ser
1955 1960 1965

Leu Ser Ser Leu Ser Asp Ile Asp Gln Glu Asn Asn Asn Lys Glu Asn
1970 1975 1980

Glu Pro Ile Lys Glu Thr Glu Pro Pro Asp Ser Gln Gly Glu Pro Ser
1985 1990 1995 2000

Lys Pro Gln Ala Ser Gly Tyr Ala Pro Lys Ser Phe His Val Glu Asp
2005 2010 2015

FIG. 3S

Thr Pro Val Cys Phe Ser Arg Asn Ser Ser Leu Ser Ser Leu Ser Ile
2020 2025 2030

Asp Ser Glu Asp Asp Leu Leu Gln Glu Cys Ile Ser Ser Ala Met Pro
2035 2040 2045

Lys Lys Lys Lys Pro Ser Arg Leu Lys Gly Asp Asn Glu Lys His Ser
2050 2055 2060

Pro Arg Asn Met Gly Gly Ile Leu Gly Glu Asp Leu Thr Leu Asp Leu
2065 2070 2075 2080

Lys Asp Ile Gln Arg Pro Asp Ser Glu His Gly Leu Ser Pro Asp Ser
2085 2090 2095

Glu Asn Phe Asp Trp Lys Ala Ile Gln Glu Gly Ala Asn Ser Ile Val
2100 2105 2110

Ser Ser Leu His Gln Ala Ala Ala Ala Ala Cys Leu Ser Arg Gln Ala
2115 2120 2125

FIG. 3T

Ser Ser Asp Ser Asp Ser Ile Leu Ser Leu Lys Ser Gly Ile Ser Leu
2130 2135 2140

Gly Ser Pro Phe His Leu Thr Pro Asp Gln Glu Glu Lys Pro Phe Thr
2145 2150 2155 2160

Ser Asn Lys Gly Pro Arg Ile Leu Lys Pro Gly Glu Lys Ser Thr Leu
2165 2170 2175

Glu Thr Lys Lys Ile Glu Ser Glu Ser Lys Gly Ile Lys Gly Gly Lys
2180 2185 2190

Lys Val Tyr Lys Ser Leu Ile Thr Gly Lys Val Arg Ser Asn Ser Glu
2195 2200 2205

Ile Ser Gly Gln Met Lys Gln Pro Leu Gln Ala Asn Met Pro Ser Ile
2210 2215 2220

Ser Arg Gly Arg Thr Met Ile His Ile Pro Gly Val Arg Asn Ser Ser
2225 2230 2235 2240

FIG. 3U

Ser Ser Thr Ser Pro Val Ser Lys Lys Gly Pro Pro Leu Lys Thr Pro
2245 2250 2255

Ala Ser Lys Ser Pro Ser Glu Gly Gln Thr Ala Thr Thr Ser Pro Arg
2260 2265 2270

Gly Ala Lys Pro Ser Val Lys Ser Glu Leu Ser Pro Val Ala Arg Gln
2275 2280 2285

Thr Ser Gln Ile Gly Gly Ser Ser Lys Ala Pro Ser Arg Ser Gly Ser
2290 2295 2300

Arg Asp Ser Thr Pro Ser Arg Pro Ala Gln Gln Pro Leu Ser Arg Pro
2305 2310 2315 2320

Ile Gln Ser Pro Gly Arg Asn Ser Ile Ser Pro Gly Arg Asn Gly Ile
2325 2330 2335

Ser Pro Pro Asn Lys Leu Ser Gln Leu Pro Arg Thr Ser Ser Pro Ser
2340 2345 2350

FIG. 3V

Thr Ala Ser Thr Lys Ser Ser Gly Ser Gly Lys Met Ser Tyr Thr Ser
2355 2360 2365

Pro Gly Arg Gln Met Ser Gln Gln Asn Leu Thr Lys Gln Thr Gly Leu
2370 2375 2380

Ser Lys Asn Ala Ser Ser Ile Pro Arg Ser Glu Ser Ala Ser Lys Gly
2385 2390 2395 2400

Leu Asn Gln Met Asn Asn Gly Asn Gly Ala Asn Lys Lys Val Glu Leu
2405 2410 2415

Ser Arg Met Ser Ser Thr Lys Ser Ser Gly Ser Glu Ser Asp Arg Ser
2420 2425 2430

Glu Arg Pro Val Leu Val Arg Gln Ser Thr Phe Ile Lys Glu Ala Pro
2435 2440 2445

Ser Pro Thr Leu Arg Arg Lys Leu Glu Glu Ser Ala Ser Phe Glu Ser
2450 2455 2460

FIG. 3W

Leu Ser Pro Ser Ser Arg Pro Ala Ser Pro Thr Arg Ser Gln Ala Gln
2465 2470 2475 2480

Thr Pro Val Leu Ser Pro Ser Leu Pro Asp Met Ser Leu Ser Thr His
2485 2490 2495

Ser Ser Val Gln Ala Gly Gly Trp Arg Lys Leu Pro Pro Asn Leu Ser
2500 2505 2510

Pro Thr Ile Glu Tyr Asn Asp Gly Arg Pro Ala Lys Arg His Asp Ile
2515 2520 2525

Ala Arg Ser His Ser Glu Ser Pro Ser Arg Leu Pro Ile Asn Arg Ser
2530 2535 2540

Gly Thr Trp Lys Arg Glu His Ser Lys His Ser Ser Ser Leu Pro Arg
2545 2550 2555 2560

Val Ser Thr Trp Arg Arg Thr Gly Ser Ser Ser Ser Ile Leu Ser Ala
2565 2570 2575

FIG. 3X

Ser Ser Glu Ser Ser Glu Lys Ala Lys Ser Glu Asp Glu Lys His Val
2580 2585 2590

Asn Ser Ile Ser Gly Thr Lys Gln Ser Lys Glu Asn Gln Val Ser Ala
2595 2600 2605

Lys Gly Thr Trp Arg Lys Ile Lys Glu Asn Glu Phe Ser Pro Thr Asn
2610 2615 2620

Ser Thr Ser Gln Thr Val Ser Ser Gly Ala Thr Asn Gly Ala Glu Ser
2625 2630 2635 2640

Lys Thr Leu Ile Tyr Gln Met Ala Pro Ala Val Ser Lys Thr Glu Asp
2645 2650 2655

Val Trp Val Arg Ile Glu Asp Cys Pro Ile Asn Asn Pro Arg Ser Gly
2660 2665 2670

Arg Ser Pro Thr Gly Asn Thr Pro Pro Val Ile Asp Ser Val Ser Glu
2675 2680 2685

FIG. 3Y

Lys Ala Asn Pro Asn Ile Lys Asp Ser Lys Asp Asn Gln Ala Lys Gln
2690 2695 2700

Asn Val Gly Asn Gly Ser Val Pro Met Arg Thr Val Gly Leu Glu Asn
2705 2710 2715 2720

Arg Leu Thr Ser Phe Ile Gln Val Asp Ala Pro Asp Gln Lys Gly Thr
2725 2730 2735

Glu Ile Lys Pro Gly Gln Asn Asn Pro Val Pro Val Ser Glu Thr Asn
2740 2745 2750

Glu Ser Pro Ile Val Glu Arg Thr Pro Phe Ser Ser Ser Ser Ser Ser
2755 2760 2765

Lys His Ser Ser Pro Ser Gly Thr Val Ala Ala Arg Val Thr Pro Phe
2770 2775 2780

Asn Tyr Asn Pro Ser Pro Arg Lys Ser Ser Ala Asp Ser Thr Ser Ala
2785 2790 2795 2800

FIG. 3Z

Arg Pro Ser Gln Ile Pro Thr Pro Val Asn Asn Asn Thr Lys Lys Arg
2805 2810 2815

Asp Ser Lys Thr Asp Ser Thr Glu Ser Ser Gly Thr Gln Ser Pro Lys
2820 2825 2830

Arg His Ser Gly Ser Tyr Leu Val Thr Ser Val
2835 2840

FIG. 4A

```
APC      203  LGTCQDMEKRAQRRIARIQQIEKDILRIRQL  233
              |     :: || |||||||:|    |     |
RAL2     576  LTGAKGLQLRALRRIARIEQGGTAISPTSPL  606
```

FIG. 4B

```
APC      453  MKLSFDEEHRHAMNELGGLQAIAELLQVD  481
              :      |  :   ||:|||| :   : :
M3 MACHR 249  LYWRIYKETEKRTKELAGLQASGTEAETE  277
              ||  :  |  :  ||||||
MCC      220  LYPNLAEERSRWEKELAGLREENESLTAM  248
              :     ||: :   ||:||    | |
APC      453  MKLSFDEEHRHAMNELGGLQAIAELLQVD  481
```

FIG. 6A

```
                                        28                                      55
GCA GTC GCC GCT CCA GTC TAT CCG GCA CTA GGA ACA GCC CCG GGN GGC GAG ACG
Ala Val Ala Ala Pro Val Tyr Pro Ala Leu Gly Thr Ala Pro Gly Gly Glu Thr
                                        82                              109
GTC CCC GCC ATG TCT GCG GCC ATG AGG GAG AGG TTC GAC CGG TTC CTG CAC GAG
Val Pro Ala MET Ser Ala Ala MET Arg Glu Arg Phe Asp Arg Phe Leu His Glu
                                        136                             163
AAG AAC TGC ATG ACT GAC CTT CTG GCC AAG CTC GAG GCC AAA ACC GGC GTG AAC
Lys Asn Cys MET Thr Asp Leu Leu Ala Lys Leu Glu Ala Lys Thr Gly Val Asn
                                        190                             217
AGG AGC TTC ATC GCT CTT GGT GTC ATC GGA CTG GTG GCC TTG TAC CTG GTG TTC
Arg Ser Phe Ile Ala Leu Gly Val Ile Gly Leu Val Ala Leu Tyr Leu Val Phe
                                        244                             271
GGT TAT GGA GCC TCT CTC CTC TGC AAC CTG ATA GGA TTT GGC TAC CCA GCC TAC
Gly Tyr Gly Ala Ser Leu Leu Cys Asn Leu Ile Gly Phe Gly Tyr Pro Ala Tyr
                                        298                             325
ATC TCA ATT AAA GCT ATA GAG AGT CCC AAC AAA GAA GAT GAT ACC CAG TGG CTG
Ile Ser Ile Lys Ala Ile Glu Ser Pro Asn Lys Glu Asp Asp Thr Gln Trp Leu
                                        352                             379
ACC TAC TGG GTA GTG TAT GGT GTG TTC AGC ATT GCT GAA TTC TTC TCT GAT ATC
Thr Tyr Trp Val Val Tyr Gly Val Phe Ser Ile Ala Glu Phe Phe Ser Asp Ile
                                        406                             433
TTC CTG TCA TGG TTC CCC TTC TAC TAC ATG CTG AAG TGT GGC TTC CTG TTG TGG
Phe Leu Ser Trp Phe Pro Phe Tyr Tyr MET Leu Lys Cys Gly Phe Leu Leu Trp
                                        460                             487
TGC ATG GCC CCG AGC CCT TCT AAT GGG GCT GAA CTG CTC TAC AAG CGC ATC ATC
Cys MET Ala Pro Ser Pro Ser Asn Gly Ala Glu Leu Leu Tyr Lys Arg Ile Ile
                                        514                             541
CGT CCT TTC TTC CTG AAG CAC GAG TCC CAG ATG GAC AGT GTG GTC AAG GAC CTT
Arg Pro Phe Phe Leu Lys His Glu Ser Gln MET Asp Ser Val Val Lys Asp Leu
```

FIG. 6B

```
                                    568                                     595
AAA GAC AAG TCC AAA GAG ACT GCA GAT GCC ATC ACT AAA GAA GCG AAG AAA GCT
Lys Asp Lys Ser Lys Glu Thr Ala Asp Ala Ile Thr Lys Glu Ala Lys Lys Ala
                                    622
ACC GTG AAT TTA CTG GGT GAA GAA AAG AAG AGC ACC TAA ACC AGA
Thr Val Asn Leu Leu Gly Glu Glu Lys Lys Ser Thr
        640         650         660         670         680         690         700
 CTAAACCAGA CTGGATGGAA ACTTCCTGCC CTCTCTGTAC CTTCCTACTG GAGCTTGATG TTATATTAGG
        710         720         730         740         750         760         770
 GACTGTGGTA TAATTATTTT AATAATGTTG CCTTGGAAAC ATTTTTGAGA TATTAAAGAT TGGAATGTGT

        780         790         800         810         820         830         840
 TGTAAGTTTC TTTGCTTACT TTTACTGTCT ATATATATAG GGAGCACTTT AAACTTAATG CAGTGGGCAG
        850         860         870         880         890         900         910
 TGTCCACGTT TTTGGAAAAT GTATTTTGCC TCTGGGTAGG AAAAGATGTA TGTTGCTATC CTGCAGGAAA
        920         930         940         950         960         970         980
 TATAAACTTA AAATAAAATT ATATACCCCA CAGGCTGTGT ACTTTACTGG GCTCTCCCTG CACGSATTTT
        990        1000        1010        1020        1030        1040        1050
 CTCTGTAGTT ACATTTAGGR TAATCTTTAT GGTTCTACTT CCTRTAATGT ACAATTTTAT ATAATTCNGR
       1060        1070        1080        1090        1100        1110        1120
 AATGTTTTTA ATGTATTTGT GCACATGTAC ATATGGAAAT GTTACTGTCT GACTACANCA TGCATCATGC
       1130        1140        1150        1160        1170        1180        1190
 TCATGGGGAG GGAGCAGGGG AAGGTTGTAT GTGTCATTTA TAACTTCTGT ACAGTAAGAC CACCTGCCAA
       1200        1210        1220        1230        1240        1250        1260
 AAGCTGGAGG AACCATTGTG CTGGTGTGGT CTACTAAATA ATACTTTAGG AAATACGTGA TTAATATGCA
       1270        1280        1290        1300        1310        1320        1330
 AGTGAACAAA GTGAGAAATG AAATCGAATG GAGATTGGCC TGGTTGTTTC CGTAGTATAT GGCATATGAA
       1340        1350        1360        1370        1380        1390        1400
```

FIG. 6C

```
TACCAGGATA GCTTTATAAA GCAGTTAGTT AGTTAGTTAC TCACTCTAGT GATAAATCGG GAAATTTACA
      1410       1420       1430       1440       1450       1460       1470
CACACACACA CACACACACA CACACACACA CACACACACA CACACACACA GAGTACCCTG TAACTCTCAA
      1480       1490       1500       1510       1520       1530       1540
TTCCCTGAAA AACTAGTAAT ACTGTCTTAT CTGCTATAAA CTTTACATAT TTGTCTATTG TCAAGATGCT
      1550       1560       1570       1580       1590       1600       1610
ACANTGGAMN CCATTTCTGG TTTTATCTTC ANAGSGGAGA NACATGTTGA TTTAGTCTTC TTTCCCAATC
      1620       1630       1640       1650       1660       1670       1680
TTCTTTTTTA AMCCAGTTTN AGGMNCTTCT GRAGATTTGY CCACCTCTGA TTACATGTAT GTTCTYGTTT
      1690       1700       1710       1720       1730       1740       1750
GTATCATKAG CAACAACATG CTAATGRCGA CACCTAGCTC TRAGMGCAAT TCTGGGAGAN TGARAGGNWG
      1760       1770       1780       1790       1800       1810       1820
TATARAGTMN CCCATAATCT GCTTGGCAAT AGTTAAGTCA ATCTATCTTC AGTTTTTCTC TGGCCTTTAA
      1830       1840       1850       1860       1870       1880       1890
GGTCAAACAC AAGAGGCTTC CCTAGTTTAC AAGTCAGAGT CACTTGTAGT CCATTTAAAT GCCCTCATCC
      1900       1910       1920       1930       1940       1950       1960
GTATTCTTTG TGTTGATAAG CTGCACAKGA CTACATAGTA AGTACAGANC AGTAAAGTTA ANNCGGATGT
      1970       1980       1990       2000       2010       2020       2030
CTCCATTGAT CTGCGAANTC GNTATAGAGA GCAATTTGTC TGGACTAGAA AATCTGAGTT TTACACCATA
      2040       2050       2060       2070       2080       2090       2100
CTGTTAAGAG TCCTTTTGAA TTAAACTAGA CTAAAACAAG TGTATAACTA AACTAACAAG ATTAAATATC
      2110       2120       2130       2140       2150       2160       2170
CAGCCAGTAC AGTATTTTTT AAGGCAAATA AAGATGATTA GCTCACCTTG AGNTAACAAT CAGGTAAGAT

      2180       2190       2200       2210       2220       2230       2240
CATNACAATG TCTCATGATG TNAANAATAT TAAAGATATC AATACTAAGT GACAGTATCA CNNCTAATAT
```

FIG. 6D

```
      2250       2260       2270       2280       2290       2300       2310
AATATGGATC AGAGCATTTA TTTTGGGGAG GAAAACAGTG GTGATTACCG GCATTTTATT AAACTTAAAA
      2320       2330       2340       2350       2360       2370       2380
CTTTGTAGAA AGCAAACAAA ATTGTTCTTG GGAGAAAATC AACTTTTAGA TTAAAAAAAT TTTAAGTAWC
      2390       2400       2410       2420       2430       2440       2450
TAGGAGTATT TAAATCCTTT TCCCATAAAT AAAAGTACAG TTTTCTTGGT GGCAGAATGA AAATCAGCAA
      2460       2470       2480       2490       2500       2510       2520
CNTCTAGCAT ATAGACTATA TAATCAGATT GACAGCATAT AGAATATATT ATCAGACAAG ATGAGGAGGT
      2530       2540       2550       2560       2570       2580       2590
ACAAAAGTTA CTATTGCTCA TAATGACTTA CAGGCTAAAA NTAGNTNTAA AATACTATAT TAAATTCTGA
      2600       2610       2620       2630       2640       2650       2660
ATGCAATTTT TTTTTGTTCC CTTGAGACCA AAATTTAAGT TAACTGTTGC TGGCAGTCTA AGTGTAAATG
      2670       2680       2690       2700       2710       2720       2730
TTAACAGCAG GAGAAGTTAA GAATTGAGCA GTTCTGTTGC ATGATTTCCC AAATGAAATA CTGCCTTGGC
      2740       2750       2760       2770       2780       2790       2800
TAGAGTTTGA AAAACTAATT GAGCCTGTGC CTGGCTAGAA AACAAGCGTT TATTTGAATG TGAATAGTGT
      2810       2820       2830       2840       2850       2860       2870
TTCAAAGGTA TGTAGTTACA GAATTCCTAC CAAACAGCTT AAATTCTTCA AGAAAGAATT CCTGCAGCAG
      2880       2890       2900       2910       2920       2930       2940
TTATTCCCTT ACCTGAAGGC TTCAATCATT TGGATCAACA ACTGCTACTC TCGGGAAGAC TCCTCTACTC
      2950       2960       2970       2980       2990       3000       3010
ACAGCTGAAG AAAATGAGCA CACCCTTCAC ACTGTTATCA CCTATCCTGA AGATGTGATA CACTGAATGG
      3020       3030       3040       3050       3060       3070       3080
AAATAAATAG ATGTAAATAA AATTGAGWTC TCATTTAAAA AAAACCATGT GCCCAATGGG AAAATGACCT
      3090       3100       3110       3120       3130       3140       3150
CATGTTGTGG TTTAAACAGC AACTGCACCC ACTAGCACAG CCCATTGAGC TANCCTATAT ATACATCTCT
      3160
GTCAGTGCCC CTC
```

APC ANTIBODIES

Matter enclosed in heavy brackets [ ] appears in the original patent but forms no part of this reissue specification; matter printed in italics indicates the additions made by reissue.

This application is a division, of application Ser. No. 08/289,548, filed Aug. 12, 1994, which is a division of application Ser. No. 07/741,940 filed Aug. 8, 1991 (issued as U.S. Pat. No. 5,352,775).

The U.S. Government has a paid-up license in this invention and the right in limited circumstances to require the patent owner to license others on reasonable terms as provided for by the terms of grants awarded by the National Institutes or Health.

TECHNICAL AREA OF THE INVENTION

The invention relates to the area of cancer diagnostics and therapeutics. More particularly, the invention relates to detection of the germline and somatic alterations of wild-type APC genes. In addition, it relates to therapeutic intervention to restore the function of APC gene product.

BACKGROUND OF THE INVENTION

According to the model of Knudson for tumorigenesis (Cancer Research, Vol. 45, p. 1482, 1985), there are tumor suppressor genes in all normal cells which, when they become non-functional due to mutation, cause neoplastic development. Evidence for this model has been found in the cases of retinoblastoma and colorectal tumors. The implicated suppressor genes in those tumors, RB, p53, DCC and MCC, were found to be deleted or altered in many cases of the tumors studied. (Hansen and Cavenee, Cancer Research, Vol. 47, pp: 5518–5527 (1987); Baker et al., Science, Vol. 244, p. 217 (1989); Fearon et al., Science, Vol. 247, p. 49 (1990); Kinzler et al. Science Vol. 251. p. 1366 (1991).)

In order to fully understand the pathogenesis of tumors, it will be necessary to identify the other suppressor genes that play a role in the tumorigenesis process. Prominent among there is the one(s) presumptively located at 5q21. Cytogenetic (Herrera et al., Am. J. Med. Genet., Vol. 25, p. 473 (1986) and linkage (Leppert et al., Science, Vol. 238, p. 1411 (1987); Bodmer et al., Nature, Vol. 328, p. 614 (1987)) studies have shown that this chromosome region harbors the gene responsible for familial adenomatous polyposis (FAP) and Gardner's Syndrome (GS). FAP is an autosomal-dominant, inherited disease in which affected individuals develop hundreds to thousands of adenomatous polyps, some of which progress to malignancy. GS is a variant of FAP in which desmold tumors, osteomas and other soft tissue tumors occur together with multiple adenomas of the colon and rectum. A less severe form of polyposis has been identified in which only a few (2–40) polyps develop. This condition also is familial and is linked to the same chromosomal markers as FAP and GS (Leppert et al., New England Journal of Medicine, Vol. 322, pp. 904–908, 1990.) Additionally, this chromosomal region is often deleted from the adenomas (Vogelstein et al., N. Engl. J. Med., Vol. 319, p. 525 (1988)) and carcinomas (Vogelstein et al., N. Engl. J. Med., Vol. 319, p. 525 (1988); Solomon et al., Nature, Vol. 328, p. 616 (1987); Sasaki et al., Cancer Research, Vol. 49, p. 4402 (1989); Delattre et al., Lancet, Vol. 2, p. 353 (1989); and Ashton-Rickardt et al., Oncogene, Vol. 4, p. 1169 (1989)) of patients without FAP (sporadic tumors). Thus, a putative suppressor gene on chromosome 5q21 appears to play a role in the early stages of colorectal neoplasia in [beth] *both* sporadic and familial tumors.

Although the MCC gene has been identified on 5q21 as a candidate suppressor gene, it does not appear to be altered in FAP or GS patients. Thus there is a need in the art for investigations of this chromosomal region to identify genes and to determine if any of such genes are associated with FAP and/or GS and the process of tumorigenesis.

SUMMARY OF THE INVENTION

It is an object of the present invention to provide a method for diagnosing and prognosing a neoplastic tissue of a human.

It is another object of the invention to provide a method of detecting genetic predisposition to cancer.

It is another object of the invention to provide a method of supplying wild-type APC gene function to a cell which has lest said gene function.

It is yet another object of the invention to provide a kit for determination of the nucleotide sequence of APC alleles by the polymerase chain reaction.

It is still another object of the invention to provide nucleic acid probes for detection of mutations in the human APC gene.

It is still another object of the invention to provide a cDNA molecule encoding the APC gene product.

It is yet another object of the invention to provide a preparation of the human APC protein.

It is another object of the invention to provide a method of screening for genetic [prodisposition] *predisposition* to cancer.

It is an object of the invention to provide methods of testing therapeutic agents for the ability to suppress neoplasia.

It is still another object of the invention to provide animals carrying mutant APC alleles.

These and other objects of the invention are provided by one or more of the embodiments which are described below. In one embodiment of the present invention a method of diagnosing or prognosing a neoplastic tissue of a human is provided comprising: detecting somatic alteration of wild-type APC genes or their expression products in a sporadic colorectal cancer tissue, said alteration indicating neoplasia of the tissue.

In yet another embodiment a method is provided of detecting genetic predisposition to cancer in a human including familial adenomatous polyposis (FAP) and Gardner's Syndrome (GS), comprising: isolating a human sample selected from the group consisting of blood and fetal tissue; detecting alteration of wild-type APC gene coding sequences or their expression products from the sample, said alteration indicating genetic predisposition to cancer.

In another embodiment of the present invention a method is provided for supplying wild-type APC gene function to a cell which has lost said gene function by virtue of a mutation in the APC gene, comprising: introducing a wild-type APC gene into a cell which has lost said gene function such that said wild-type gene is expressed in the cell.

In another embodiment a method of supplying wild-type APC gene function to a cell is provided comprising: introducing a portion of a wild-type APC gene into a cell which has lost said gene function such that said portion is expressed in the cell, said portion encoding a part of the APC protein which is required for non-neoplastic growth of said cell. APC protein can also be applied to cells or administered to animals to remediate for mutant APC genes. Synthetic peptides or drugs can also be used to mimic APC function in cells which have altered APC expression.

In yet another embodiment a pair of single stranded primers is provide for determination of the nucleotide sequence of the APC gene by polymerase chain reaction. The sequence of said pair of single stranded DNA primers is derived from chromosome 5q band 21, said pair of primers allowing synthesis of APC gene coding sequences.

In still another embodiment of the invention a nucleic acid probe is provided which is complementary to human wild-type APC gene ceding sequences and which can form mismatches with mutant APC genes, thereby allowing their detection by enzymatic or chemical cleavage or by shifts in electrophoretic mobility.

In another embodiment of the invention a method is provided for detecting the presence of a neoplastic tissue in a human. The method comprises isolating a body sample from a human; detecting in said sample alteration of a wild-type APC gene sequence or wild-type APC expression product, said alteration indicating the presence of a neoplastic tissue in the human.

In still another embodiment a cDNA molecule is provided which comprises the coding sequence of the APC gene.

In even another embodiment a preparation of the human APC protein is provided which is substantially free of other human proteins. The amino acid sequence of the protein is shown in [FIG. 3] *FIGS. 3A–3Z* (SEQ ID NOS: 7 and 2).

In yet another embodiment of the invention a method is provided for screening for genetic predisposition to cancer, including familial adenomatous polyposis (FAP) and Gardner's Syndrome (GS), in a human. The method comprises: detecting among kindered persons the presence of a DNA polymorphism which is linked to a mutant APC allele in an individual having a genetic predisposition to cancer, said kindered being genetically related to the individual, the presence of said polymorphism suggesting a predisposition to cancer.

In another embodiment of the invention a method of testing therapeutic agents for the ability to suppress a neoplastically transformed phenotype is provided. The method comprises: applying a test substance to a cultured epithelial cell which carries a mutation in an APC allele; and determining whether said test substance suppresses the neoplastically transformed phenotype of the cell.

In another embodiment of the invention a method of testing therapeutic agents for the ability to suppress a neoplastically transformed phenotype is provided. The method comprises: administering a test substance to an animal which carries a mutant APC allele; and determining whether said test substance prevents or suppresses the growth of tumors.

In still other embodiments of the invention transgenic animals are provided. The animals carry a mutant APC allele from a second animal species or have been genetically engineered to contain an insertion mutatation which disrupts an APC allele.

The present invention provides the art with the information that the APC gene, a heretofore unknown gene is, in fact, a target of mutational alterations on chromosome 5q21 and that these alterations are associated with the process of tumorigenesis. This information allows highly specific assays to be performed to assess the neoplastic status of a particular tissue or the predisposition to cancer of an individual. This invention has applicability to Familial Adenomatous Polyposis, sporadic colorectal cancers, Guardner's Syndrome, as well as the less severe familial polyposis discusses above.

BRIEF DESCRIPTION OF THE DRAWINGS

FIGS. 2A and 2B show the sequence of TB1 (FIG. 2A, *SEQ ID NO:5*) and TB2 (FIG. 2B, *SEQ ID NO:6*) [genes] *proteins*. The cDNA sequence of the TB1 gene was determined from the analysis of 11 cDNA clones derived from normal colon and liver, as described in the text. A total of 2314 bp were contained within the overlapping cDNA clones, defining an ORF of 424 amino acids beginning at nucleotide 1. Only the predicted amino acids from the ORF are shown. The carboxy-terminal end of the ORF has apparently been identified, but the 5' end of the TB1 transcript has not yet been precisely determined.

The cDNA sequence of the TB2 gene was determined from the YS-39 clone derived as described in the text. This clone consisted of 2300 bp and defined an ORF of 185 amino acids beginning at nucleotide 1. Only the predicted amino acids are shown. The carboxy terminal end of the ORF has apparently been identified, but the 5' end of the TB2 transcript has not been precisely determined.

[FIGS. 3A–3F] *FIGS. 3A–3Z* show the sequence of the APC gene product (SEQ ID NO:7). The cDNA sequence was determined through the analysis of 87 cDNA clones derived from normal colon, liver, and brain. A total of 8973 bp were contained within overlapping cDNA clones, defining an ORF of [2842] *2843* amino acids. In frame stop codons surrounded this ORF, as described in the text, suggesting that the entire APC gene product was represented in the ORF illustrated. Only the predicted amino acids are shown.

FIGS. 4A and 4B show the local similarity between human APC (SEQ ID NO:2) and ral2 (SEQ ID NO:8) of yeast. FIG. 4A shows amino acids 203 to 233 of APC, and FIG. 4B shows amino acids 453 to 481 of APC. Local similarity among the APC (SEQ ID NO:2) and MCC genes (SEQ ID NO:10) genes and the m3 muscarinic acetylcholine receptor (SEQ ID NO:9) is shown. The region of the mAChR shown corresponds to that responsible for coupling the receptor to G proteins. The connecting lines indicate identities; dots indicate related amino acids residues.

Figure 5:
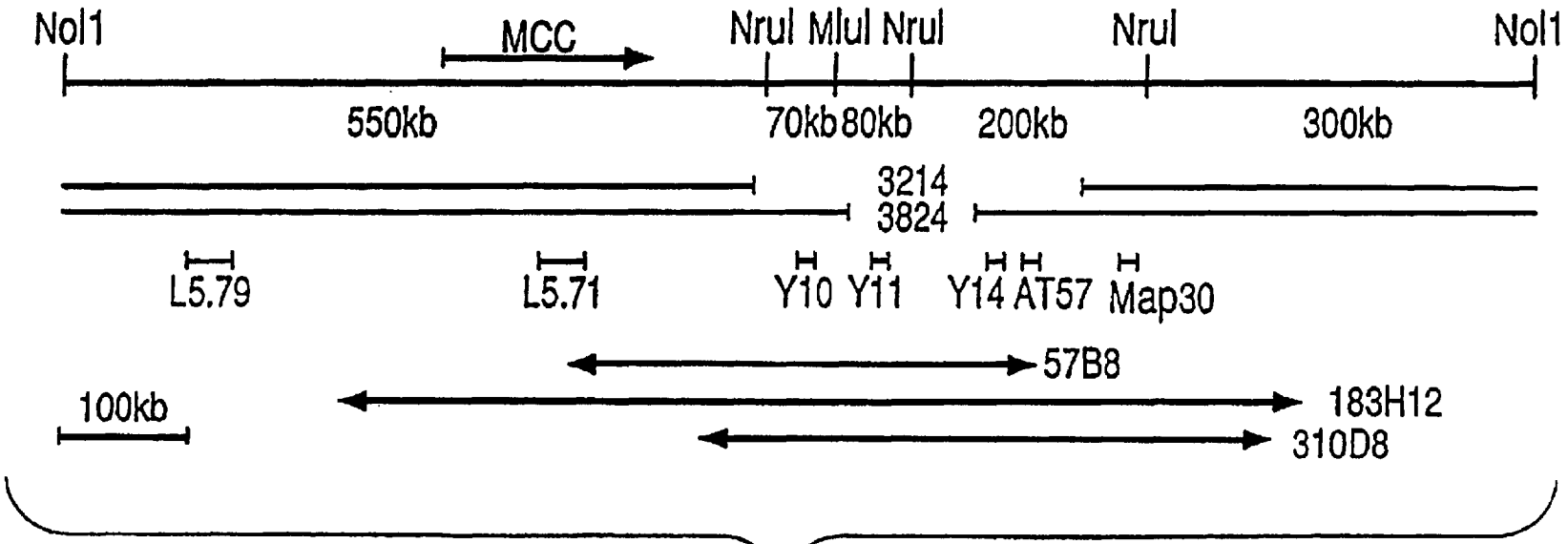

FIG. 5 shows the genomic map of the 1200 kb NotI fragment at the FAP locus. The NotI fragment is shown as a bold line. Relevant parts of the deletion chromosomes from patients 3214 and 3824 are shown as stippled lines. Probes used to characterize the NotI fragment and the deletions, and three YACs from which subclones were obtained, are shown below the restriction map. The chimeric end of YAC 183H12 is indicated by a dotted line. The orientation and approximate position of MCC are identified above the map.

FIG. 6A-6D show the DNA sequence (SEQ ID NO:3) and predicted amino acid sequence of DP1 (TB2) (SEQ ID NO:4). The nucleotide numbering begins at the most 5' nucleoitde isolated. A proposed initiation methionine (base 77) is indicated in bold type. The entire coding sequence is presented.

FIG. 7A, FIG. 7B-1, and FIG. 7B-2 show the arrangement of exons in DP2.5 (APC). (A) Exon 9 corresponds to nucleotides 933–1312; exon 9a corresponds to nucleotides 1236–1312. The stop codon in the cDNA is at nucleotide 8535. (B) Partial intronic sequence surrounding each exon is shown (SEQ ID NO: 11–38). 5' intron sequences of exons 2, 3, 4, 5, 6, 7, 8, 9, 10, 11, 12, 13, 14, and 15 are shown in SEQ ID NOS: 12, 14, 16, 18, 20, 22, 24, 26, 28, 30, 32, 34, 36, 38, respectively. 3' intron sequences of exons 1, 2, 3, 4, 5, 6, 7, 8, 9, 10, 11, 12, 13, and 14 are shown in SEQ ID NOS: 11, 13, 15, 17, 19, 21, 23, 25, 27, 29, 31, 33, 35, 37, respectively.

DETAILED DESCRIPTION

It is a discovery of the present invention that mutational events associated with tumorigenesis occur in a previously unknown gene on chromosome 5q named here the APC (Adenomatous Polyposis Coil) gene. Although it was previously known that deletion of alleles of chromosome 5q were common in certain types of cancers, it was not known that a target gene of these deletions was the APC gene. Further it was not known that other types of mutational events in the APC gene and also associated with cancers. The mutations of the APC gene can involve gross rearrangements, such as insertions and deletions. Point mutations have also been observed.

According to the diagnostic and prognostic method of the present invention, alteration of the wild-type APC gene is detected. "Alteration of a wild-type gene" according to the present invention encompasses all forms of mutations—including deletions. The alteration may be due to either rearrangements such as insertions, inversions, and deletions, or to point mutations. Deletions may be of the entire gene or only a portion of the gene. Somatic mutations are those which occur only in certain tissues, e.g., in the tumor tissue, and are not inherited in the germline. Germline mutations can be found in any of a body's tissues. If only a single allele is somatically mutated, an early neoplastic state is indicated. However, if both alleles are mutated then a late neoplastic state is indicated. The finding of APC mutations thus provides both diagnostic and prognostic information. An APC allele which is not deleted (e.g., that on the sister chromosome to a chromosome carrying an APC deletion) can be screened for other mutations, such as insertions, small deletions, and point mutations. It is believed that many mutations found in tumor tissues will be those leading to decreased expression of the APC gene product. However, mutations leading to non-functional gene products would also lead to a cancerous state. Point mutational events may occur in regulatory regions, such as in the promoter of the gene, leading to loss or diminution of expression of the mRNA. Point mutations may also abolish proper RNA processing, leading to loss of expression of the APC gene product.

In order to detect the alteration of the wild-type APC gene in a tissue, it is helpful to isolate the tissue free from surrounding normal tissues. Means for enriching a tissue preparation for tumor cells are known in the art. For example, the tissue may be isolated from paraffin or cryostat sections. Cancer cells may also be separated from normal cells by flow cytometry. These as well as other techniques for separating tumor from normal cells are well known in the art. If the tumor tissue is highly contaminated with normal cells, detection of mutations is more difficult.

Detection of point mutations may be accomplished by molecular cloning of the APC allele (or alleles) and sequencing that allele(s) using techniques well known in the art. Alternatively, the polymerase chain reaction (PCR) can be used to amplify gene sequences directly from a genomic DAN preparation from the tumor tissue. The DNA sequence of the amplified sequences can then be determined. The polymerase chain reaction itself is well known in the art. See, e.g., Saiki et al., Science, Vol. 239, p. 487, 1988; U.S. Pat. No. 4,683,203; and U.S. Pat. No. 4,683,195. Specific primers which can be used in order to amplify the gene will be discussed in more detail below. The ligase chain reaction, which is known in the art, can also be used to amplify APC sequences. See Wu et al., Genomics, Vol. 4, pp. 560–569 (1989). In addition, a technique known as allele specific PCR can be used. (See Ruano and Kidd, Nucleic Acids Research, Vol. 17, p. 8392, 1989.) According to this technique, primers are used which hybridize at their 3' ends to a particular APC mutation. If the particular APC mutation is not present, an amplification product is not observed. Amplification Refractory Mutation System (ARMS) can also be used as disclosed in European Patent Application Publication No. 0332435 and in Newton et al., Nucleic Acids Research, Vol. 17, p.7, 1989. Insertions and deletions of genes can also be detected by cloning, sequencing and amplification. In addition, restriction fragment length polymorphism (RFLP) probes for the gene or surrounding marker genes can be used to score alteration of an allele or an insertion in a polymorphic fragment. Such a method is particularly useful for screening among kindered persons of an affected individual for the presence of an APC mutation found in that individual. Single stranded conformation polymorphism (SSCP) analysis can also be used to detect base change variants of an allele. (Orita et al., Proc. Natl. Acad. Sci. USA Vol. 86, pp. 2766–2770, 1989, and Genomics, Vol. 5, pp. 874–879, 1989.) Other techniques for detecting insertions and deletions as are known in the art can be used.

Alteration of wild-type genes can also be detected on the basis of the alteration of a wild-type expression product of the gene. Such expression products include both the APC mRNA as well as the APC protein product. The sequences of these products are shown in [FIG. 3] *FIGS. 3A–3Z*. Point mutations may be detected by amplifying and sequencing the mRNA or via molecular cloning of cDNA made from the mRNA. The sequence of the cloned cDNA can be determined using DNA sequencing techniques which are well known in the art. The cDNA can also be sequenced via the polymerase chain reaction (PCR) which will be discussed in more detail below.

Mismatches, according to the present invention are hybridized nucleic acid duplexes which are not 100% homologous. The lack of total homology may be due to deletions, insertions, inversions, substitutions or frameshift mutations. Mismatch detection can be used to detect point mutations in the gene or its mRNA product. While these techniques are less sensitive than sequencing, they are simpler to perform on a large number of tumor samples. An example of a mismatch cleavage technique is the RNase protection method, which is described in detail in Winter et al., Proc. Nat. Acad. Sci. USA, Vol. 82, p. 7575, 1985 and Meyers et al., Science, Vol. 230, p. 1242, 1985. In the practice of the present invention the method involves the use of a labeled riboprobe which is complementary to the human wild-type APC gene coding sequence. The riboprobe and either mRNA or DNA isolated from the tumor tissue are annealed (hybridized) together and subsequently digested with the enzyme RNase A which is able to detect some mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen which is smaller than the full-length duplex RNA for the riboprobe and the mRNA or DNA. The riboprobe need not be the full length of the APC mRNA or gene but can be a segment of either. [II] *If* the riboprobe comprises only a segment of the APC mRNA or gene it will be desirable to use a number of these probes to screen the whole mRNA sequence for mismatches.

In similar fashion, DNA probes can be used to detect mismatches, through enzymatic or chemical cleavage. See, e.g., Crotton et al., Proc. Natl. Acad. Sci. USA, Vol. 85, 4397, 1988; and Shenk et al., Proc. Natl. Acad. Sci. USA, Vol. 72, p. 989; 1975. Alternatively, mismatches can be detected by shifts in the electrophoretic mobility of mismatched duplexes relative to matched duplexes. See, e.g., Cariello, Human Genetics, Vol. 42, p. 726, 1988. With either riboprobes or DNA probes, the cellular mRNA or DNA which might contain a mutation can be amplified using PCR (see below) before hybridization. Changes in DNA of the APC gene can also be detected using Southern hybridization, especially if the changes are gross rearrangements, such as deletions and insertions.

DNA sequences of the APC gene which have been amplified by use of polymerase chain reaction may also be screened using allele-specific probes. These probes are nucleic acid oligomers, each of which contains a region of the APC gene sequence harboring a known mutation. For example, one oligomer may be about 30 nucleotides in length, corresponding to a portion of the A PC gene sequence. By use of a battery of such allele-specific probes, PCR amplification products can be screened to identify the presence of a previously identified mutation in the APC gene. Hybridization of allele-specific probes with amplified APC sequences can be performed, for example, on a nylon filter. Hybridization to a particular probe under stringent hybridization conditions indicates the presence of the same mutation in the tumor tissue as in the allele-specific probe.

Alteration of APC mRNA expression can be detected by any technique known in the art. These include Northern blot analysis, PCR amplification and RNase protection. Diminished mRNA expression indicates an alteration of the wild-type APC gene. Alteration of wild-type APC genes can also be detected by screening for alteration of wild-type APC protein. For example, monoclonal antibodies immunoreactive with APC can be used to screen a tissue. Lack of cognate antigen would indicate an APC mutation. Antibodies specific for products of mutant alleles could also be used to detect mutant APC gene product. Such immunological assays can be done in any convenient format known in the art. These include Western blots, immunohistochemical assays and ELISA assays. Any means for detecting an altered APC protein can be used to detect alteration of wild-type APC genes. Functional assays can be used, such as protein binding determinations. For example, it is believed that APC protein oligomerizes to itself and/or MCC protein or binds to a G protein. Thus, an assay for the ability to bind to wild type APC or MCC protein or that G protein can be employed. In addition, assays can be used which detect APC biochemical function. It is believed that APC is involved in phospholipid metabolism. Thus, assaying the enzymatic products of the involved phospholipid metabolic pathway can be used to determine APC activity. Finding a mutant APC gene product indicates alteration of a wild-type APC gene.

Mutant APC gene or gene products can also be detected in other human body samples, such as, serum, stool, urine and sputum. The same techniques discussed above for detection of mutant APC genes or gene products in tissues can be applied to other body samples. Cancer cells are sloughed off from tumors and appear in such body samples. In addition, the APC gene product itself may be secreted into the extracellular space and found in these body samples even in the absence of cancer cells. By screening such body samples, a simple early diagnosis can be achieved for many types of cancers. In addition, the progress of chemotherapy or radiotherapy can be monitored more easily by testing such body samples for mutant APC genes or gene products.

The methods of diagnosis of the present invention are applicable to any tumor in which APC has a role in tumorigenesis. Deletions of chromosome arm 5q have been observed in tumors of lung, breast, colon, rectum, bladder, liver, sarcomas, stomach and prostate, as well as in leukemias and lymphomas. Thus these are likely to be tumors in which APC has a role. The diagnostic method of the present invention is useful for clinicians so that they can decide upon an appropriate course of treatment. For example, a tumor displaying alteration of both APC alleles might suggest a more aggressive therapeutic regimen than a tumor displaying alteration of only one APC allele.

The primer pairs of the present invention are useful for determination of the nucleotide sequence of a particular APC allele using the polymerase chain reaction. The pairs of single stranded DNA primers can be annealed to sequences within or surrounding the APC gene or chromosome 5q in order to prime amplifying DNA synthesis of the APC gene itself. A complete set of these primers allows synthesis of all of the nucleotides of the APC gene coding sequences, i.e., the exons. The set of primers preferably allows synthesis of both intron and exon sequences. Allele specific primers can also be used. Such primers anneal only to particular APC mutant alleles, and thus will only amplify a product in the presence of the mutant allele as a template.

In order to facilitate subsequent cloning of amplified sequences, primers may have restriction enzyme site sequences appended to their 5' ends. Thus, all nucleotides of the primers are derived from APC sequences or sequences adjacent to APC except the few nucleotides necessary to form a restriction enzyme site. Such enzymes and sites are well known in the art. The primers themselves can be synthesized using techniques which are well known in the art. Generally, the primers can be made using oligonucleotide synthesizing machines which are commercially available. Given the sequence of the APC open reading frame shown in [FIG. 3] *FIGS. 3A–3Z* (SEQ ID NO:1), design of particular primers is well within the skill of the art.

The nucleic acid probes provided by the present invention are useful for a number of purposes. They can be used in Southern hybridization to genomic DNA and in the RNase protection method for detecting point mutation already discussed above. The probes can be used to detect PCR amplification products. They may also be used to detect mismatches with the APC gene or mRNA using other techniques. Mismatches can be detected using either enzymes (e.g., S1 nuclease), chemicals (e.g., hydroxylamine or osmium tetraoxide and piperidine), or changes in electrophoretic mobility of mismatched hybrids as compared to totally matched hybrids. These techniques are known in the art. See, Cotton, supra, Shenk, supra, Myers, supra, Winter, supra, and Novack et al., Proc. Natl. Acad. Sci. USA, Vol. 83, p. 586, 1986. Generally, the probes are complementary to APC gene coding sequences, although probes to certain introns are also contemplated. An entire battery of nucleic acid probes is used to compose a kit for detecting alteration of wild-type APC genes. The kit allows for hybridization to the entire APC gene. The probes may overlap with each other or be contiguous.

If a riboprobe is used to detect mismatches with mRNA, it is complementary to the mRNA of the human wild-type APC gene. The riboprobe thus is an anti-sense probe in that it does not code for the APC protein because it is of the opposite polarity to the sense strand. The riboprobe generally will be labeled with a radioactive, colorimetric, or fluorometric material, which can be accomplished by any means known in the art. If the riboprobe is used to detect mismatches with DNA it can be of either polarity, sense or anti-sense. Similarity, DNA probes also may be used to detect mismatches.

Nucleic acid probes may also be complementary to mutant alleles of the APC gene. These are useful to detect similar mutations in other patients on the basis of hybridization rather than mismatches. These are discussed above and referred to as allele-specific probes. As mentioned above, the A PC probes can also be used in Southern hybridizations to genomic DNA to detect gross chromosomal changes such as deletions and insertions. The probes can also be used to select cDNA clones of APC genes from tumor and normal tissues. In addition, the probes can be used to detect APC mRNA in tissues to determine if expression is diminished as a result of alteration of wild-type APC genes.

According to the present invention a method is also provided of supplying wild-type APC function to a cell which carries mutant APC alleles. Supplying such function should suppress neoplastic growth of the recipient cells. The wile-type APC gene or a part of the gene may be introduced into the cell in a vector such that the gene remains extrachromosomal. In such a situation the gene will be expressed by the cell from the extrachromosomal location. If a gene portion is introduced and expressed in a cell carrying a mutant APC allele, the gene portion should encode a part of the APC protein which is required for non-neoplastic growth of the cell. More preferred is the situation where the wild-type APC gene or a part of it is introduced into the mutant cell in such a way that it recombines with the endogenous mutant APC gene present in the cell. Such recombination requires a double recombination event which results in the correction of the APC gene mutation. Vectors for introduction of genes [beth] *both* for recombination and for extrachromosomal maintenance are known in the art and any suitable vector may be used. Methods for introducing DNA into cells such as electroporation, calcium phosphate co-precipitation and viral transduction are known in the art and the choice of method is within the competence of the routineer. Cells transformed with the wild-type [A PC] *APC* gene can be used as model systems to study cancer remission and drug treatments which promote such remission.

Similarly, cells and animals which carry a mutant APC allele can be used as model systems to study and test for substances which have potential as therapeutic agents. The cells are typically cultured epithelial cells. These may be isolated from individuals with APC mutations, either somatic or germline. Alternatively, the cell line can be engineered to carry the mutation in the APC allele. After a test substance is applied to the cells, the neoplastically transformed [pheno-type] *phenotype* of the cell will be determined. Any trait of neoplastically transformed cells can be assessed, including anchorage-independent growth, tumorigenicity in nude mice, invasiveness of cells, and growth factor dependence. Assays for each of these traits are known in the art.

Animals for testing therapeutic agents can be selected after mutageneis of whole animals or after treatment of germline cells or zygotes. Such treatments include insertion of mutant A PC alleles, usually from a second animal species, as well as insertion of disrupted homologous genes. Alternatively, the endogenous APC gene(s) of the animals may be disrupted by insertion or deletion mutation. After test substances have been administered to the animals, the growth of tumors must be assessed. If the test substance prevents or suppresses the growth of tumors, then the test substance is a candidate therapeutic agent for the treatment of FAP and/or sporadic cancers.

Polypeptides which have APC activity can be supplied to cells which carry mutant or missing APC alleles. The sequence of the APC protein is disclosed in [FIG. 3] *FIGS. 3A–3Z* (SEQ ID NO:7). [These two sequences differ slightly and appear to be indicate the existence of two different forms of the APC protein.] Protein can be produced by expression of the cDNA sequence in bacteria, for example, using known expression vectors. Alternatively, APC can be extracted from APC-producing mammalian cells such as brain cells. In addition, the techniques of synthetic chemistry can be employed to synthesize APC protein. Any of such techniques can provide the preparation of the present invention which comprises the APC protein. The preparation is substantially free of other human proteins. This is most readily accomplished by synthesis in a microorganism or *in vitro*.

Active APC molecules can be introduced into cells by microinjection or by use of liposomes, for example. Alternatively, some such active molecules may be taken up by cells, actively or by diffusion. Extracellular application of APC gene product may be sufficient to affect tumor growth. Supply of molecules with APC activity should lead to a partial reversal of the neoplastic state. Other molecules with APC activity may also be used to effect such a reversal, for example peptides, drugs, or organic compounds.

The present invention also provides a preparation of antibodies immunoreactive with a human APC protein. The antibodies may be polyclonal or monoclonal and may be raised against native APC protein, APC fusion proteins, or mutant APC proteins. The antibodies should be immunoreactive with APC epitopes, preferably epitopes not present on other human proteins. In a preferred embodiment of the invention the antibodies will immunoprecipitate APC proteins from solution as well as react with APC protein on Western or immunoblots of polyacrylamide gels. In another preferred embodiment, the antibodies will detect APC proteins in paraffin or frozen tissue sections, using immunocytochemical techniques. Techniques for raising and purifying antibodies are well known in the art and any such techniques may be chosen to achieve the preparation of the invention.

Predisposition to cancers as in FAP and GS can be ascertained by testing any tissue of a human for mutations of the APC gene. For example, a person who has inherited a germline APC mutation would be prone to develop cancers. This can be determined by testing DNA from any tissue of the persons's body. Most simply, blood can be drawn and DNA extracted from the cells of the blood. In addition, prenatal diagnosis can be accomplished by testing fetal cells, placental cells, or amniotic fluid for mutation of the APC gene. Alteration of a wild-type APC allele, whether for example, by point mutation or by deletion, can be detected by any of the means discussed above.

Molecules of cDNA according to the present invention are intron-free, APC gene ceding molecules. They can be made by reverse transcriptase using the APC mRNA as a template. These molecules can be propagated in vectors and cell lines as is known in the art. Such molecules have the sequence shown in SEQ ID NO:3. The cDNA can also be made using the techniques of synthetic chemistry given the sequence disclosed herein.

A short region of homology has been identified between APC and the human m3 muscarinic acetylcholine receptor (mAChR). This homology was largely confined to 29 residues in which 6 out of 7 amino acids (EL(GorA)GLQA) were identical (See [FIG. 4] *FIG. 4B* (SEQ ID NO: 9)). Initially, it was not known whether this homology was significant, because many other proteins had higher levels of global homology (though few had six out of seven contiguous amino acids in common). However, a study on the sequence elements controlling G protein activation by mAChR subtypes (Lechleiter et al., EMBO J., p. 4381 (1990)) has shown that a 21 amino acid region from the m3 mAChR completely mediated G protein specificity when substituted for the 21 amino acids of m2 mA ChR at the analogous protein position. These 21 residues overlap the 19 amino acid homology between APC and m3 mA ChR.

This connection between APC and the G protein activating region of the mAChR is intriguing in light of previous investigations relating G proteins to cancer. For example, the RAS oncogenes, which are often mutated in colorectal cancers (Vogelstein, et al., N. Engl. J. Med., Vol. 319, p. 525 (1988); Bos et al., Nature Vol. 327, p. 293 (1987)), are members of the (1 protein family (Bourne, et al, Nature, Vol. 348, p. 125 (1990)) as is an in vitro transformation suppressor (Noda et al., Proc. Natl. Acad. Sci. USA, Vol. 86, p. 162 (1989)) and genes mutated in hormone producing tumors (Candis et al., Nature, vol. 340, p. 692 (1989); Lyons et al., Science, Vol. 249, p. 655 (1990)). Additionally, the gene responsible for neurofibromatosis (presumably a tumor suppressor gene) has been shown to activate the GTPase activity of RAS (Xu et al., Cell, Vol. 63, p. 835 (1990); Martin et al., Cell, Vol. 63, p. 843 (1990); Ballester et al., Cell, Vol. 63, p. 851 (1990)). Another interesting link between G proteins and colon cancer involves the drug sulindac. This agent has been shown to inhibit the growth of benign colon tumors in patients with FAP, presumably by virtue of its activity as a cyclooxygenase inhibitor (Waddell et al., J. Surg. Oncolong 24(1), 83 (1983); Wadell et al., Am. J. Surg., 157(1), 175 (1989); Charneau et al., Gastroenterologie Clinique at Biologique 14(2), 153 (1990)). Cyclooxygenase is required to convert arachidonic acid to prostaglandis and other biologically active molecules. G proteins are known to regulate phospholipase A2 activity, which generates arachidonic acid from phospholipids (Role et al., Proc. Natl. Acad. Sci. USA, Vol. 84, p. 3623 (1987); Kurachi et al., Nature, Vol. 337, 12 555 (1989)). Therefore we propose that wild-type APC protein functions by interacting with a G protein and is involved in phospholipid metabolism.

The following are provided for exemplification purposes only and are not intended to limit the scope of the invention which has been described in broad terms above.

EXAMPLE 1

This example demonstrates the isolation of a 5.5 Mb region of human DNA linked to the FAP locus. Six genes are identified in this region, all of which are expressed in normal colon cells and in colorectal, lung, [ad] *and* bladder tumors.

Figure 1A:
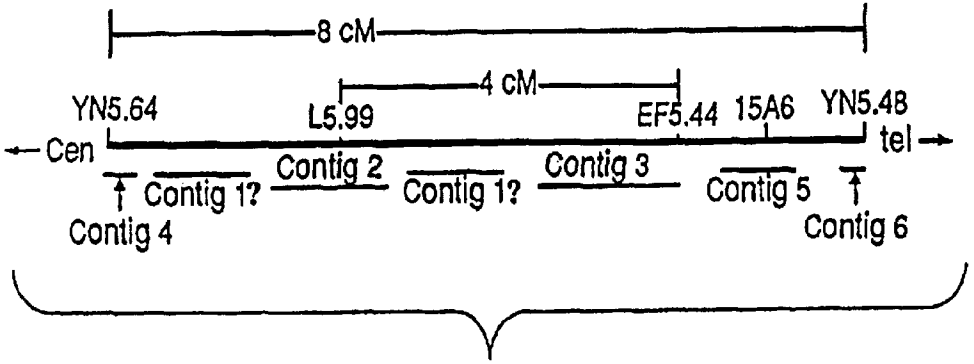
FIG. 1A shows an overview of yeast artificial chromosome (YAC) contigs. Genetic distances between selected RFLP markers from within the contigs are shown in centi-Morgans.

The cosmid markers YN5.64 and YN5.48 have previously been shown to delimit an 8 cM region containing the locus for FAP (Nakamura et al., Am. J. Hum. Genet. Vol. 43, p. 638 (1988)). Further linkage and pulse-field gel electrophoresis (PFGE) analysis with additional markers has shown that the FAP locus is contained within a 4 cM region bordered by cosmids EF5.44 and L5.99. In order to isolate clones representing a significant portion of this locus, a yeast artificial chromosome (YAC) library was screened with various 5q21 markers. Twenty-one YAC clones, distributed within six contigs and including 5.5 Mb from the region between YN5.64 and YN5.48, were obtained (FIG. 1A).

Figures 1, 1B:
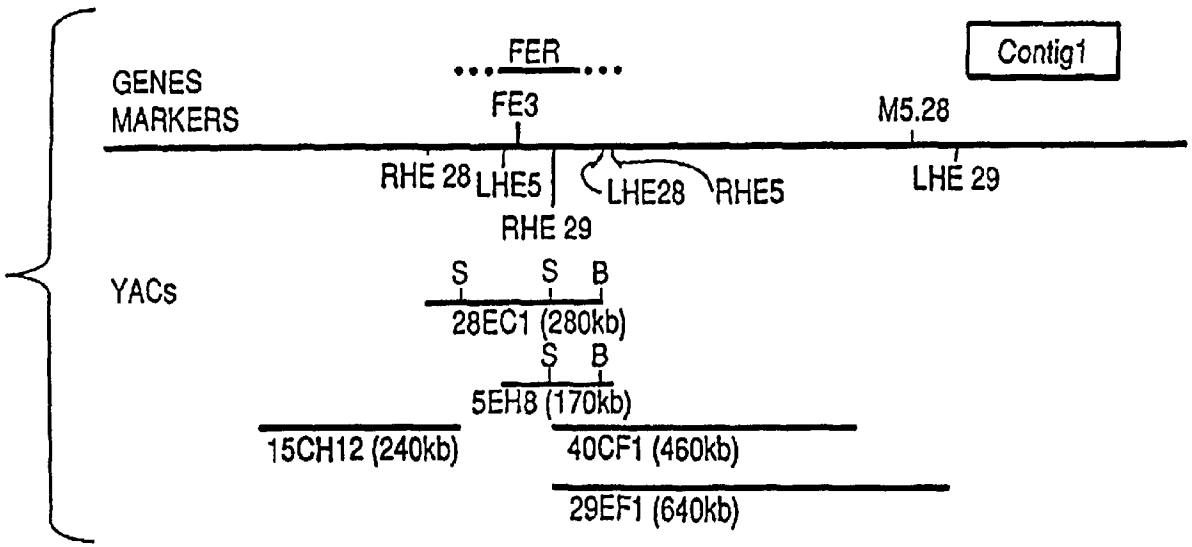
FIGS. 1B-1, 1B-2 and 1B-3 show a detailed map of the three central contigs. The position of the six identified genes from within the FAP region is shown: the 5' and 3' ends of the transcripts from these genes have in general not yet been isolated, as indicated by the string of dots surrounding the bars denoting the genes' positions. Selected restriction endonuclease recognition sites are indicated. B, BssH2; S, SstII; M, MluI; N, NruI.
Figures 1, 1B, 2:
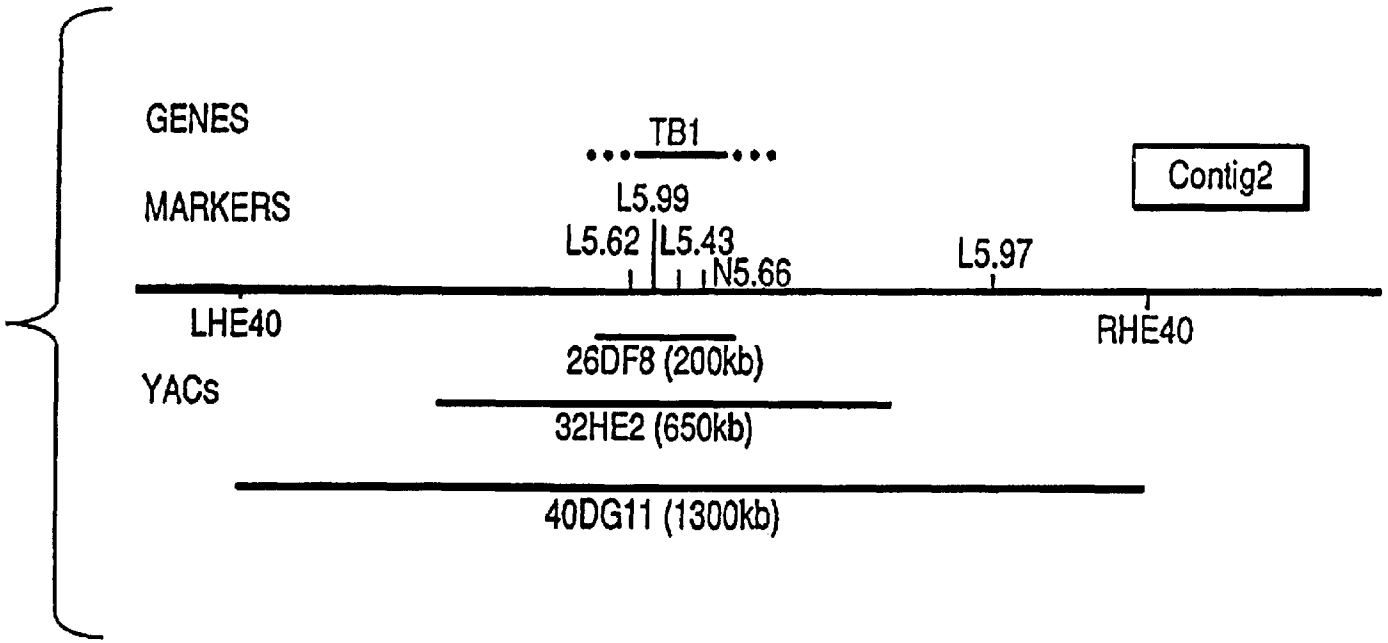
Figures 1, 1B, 2, 3:
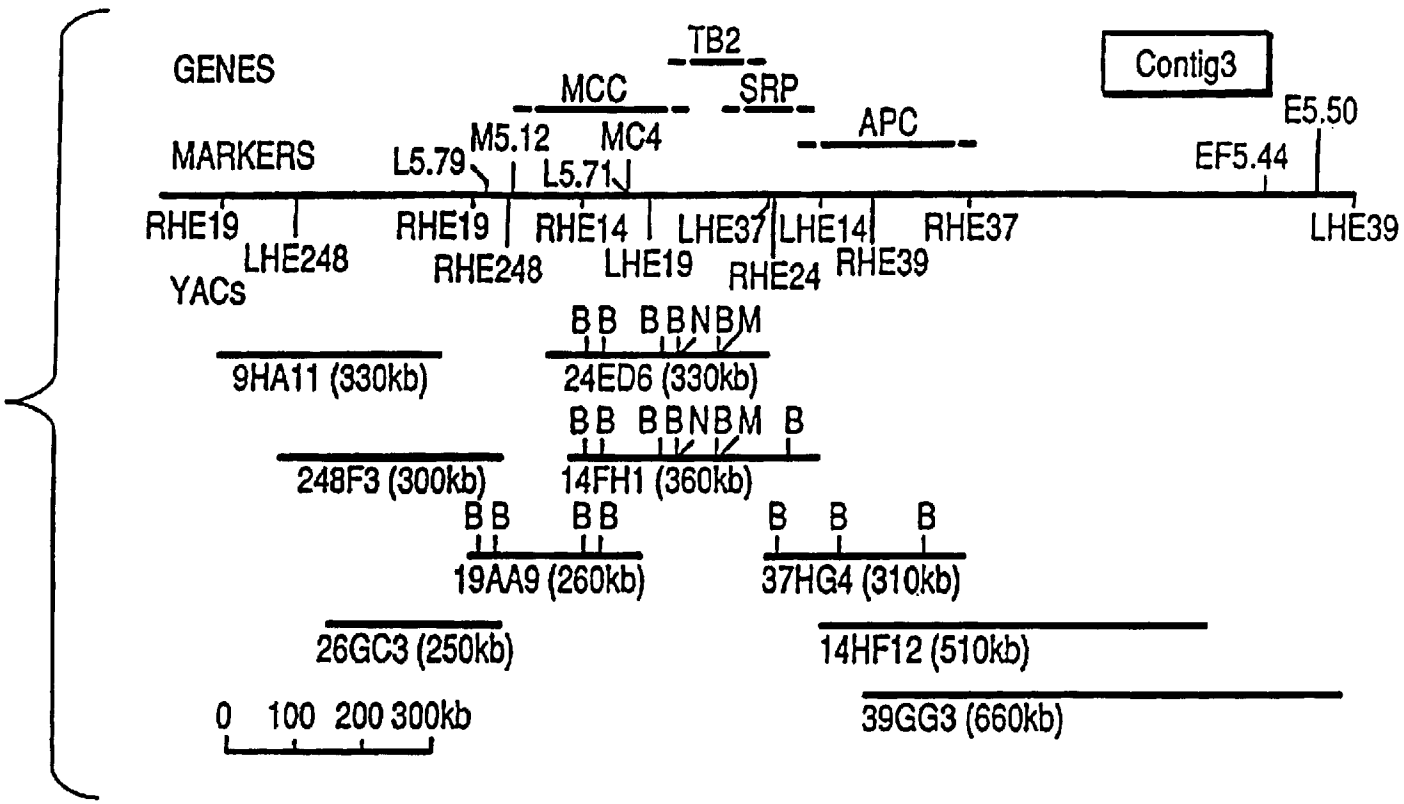

Three contigs encompassing approximately 4 Mb were contained within the central portion of this region. The [YAC's] *YACs* constituting these contigs, together with the markers used for their isolation and orientations, are shown in FIG. 1. These YAC contigs were obtained in the following way. To initiate each contig, the sequence of a genomic marker cloned from chromosome 5q21 was determined and used to design primers for PCR. PCR was then carried out on pools of YAC clones distributed in microtiter trays as previously described (Anand et al., Nucleic Acids Research, Vol. 18, p. 1951 (1980)). Individual YAC clones from the positive pools were identified by further PCR or hybridization based assays, and the YAC sizes were determined by PFGE.

To extend the areas covered by the original YAC clones, "chromosomal walking" was performed. For this purpose, YAC termini were isolated by a PCR based method and sequenced (Riley et al., Nucleic Acids Research, Vol. 18, p. 2887 (1990)). PCR primers based on these sequences were then used to rescreen the YAC library. For example, the sequence from an intron of the FER gene (Hao et al., Mol. Cell. Biol., Vol. 9, p. 1587 (1989)) was used to design PCR primers for isolation of the 28EC1 and 5EH8 YACs. The termini of the 28EC1 YAC were sequenced to derive markers RHE28 and LHE28, respectively. The sequences of these two markers were then used to isolate YAC clones 15CH12 (from RHE28) and 40CF1 and 29EF1 (from LHE28). These five [YAC's] *YACs* formed a contig encompassing 1200 kb (contig 1, FIG. 1B).

Similarly, contig 2 was initiated using cosmid N5.66 sequences, and contig 3 was initiated using sequences both from the MCC gene and from cosmid EF5.44. A walk in the telomeric direction from YAC 14FH1 and a walk in the opposite direction from YAC39GG3 allowed connection of the initial contig 3 clones through YAG 37HG4 (FIG. 1B). YAC37HG4 was deposited at the National Collection of Industrial and Marine Bacteria (NCIMB), P.O. Box 31, 23 St. Machar Drive, Aberdeen AB2 1RY, Scotland, under Accession No. 40353 on Dec. 17, 1990.

Multipoint linkage analysis with the various markers used to define the contigs, combined with PPGE analysis, showed that contigs 1 and 2 were centromeric to contig 3. These contigs were used as tools to orient and/or identify genes which might be responsible for FAP. Six genes were found to lie within this cluster of [YAC's]*YACs*, as follows:

Contig #1: FER—The FER gene was discovered through its homology to the viral oncogene. ABL (Hao et al., supra). It has an intrinsic tyrosine kinase activity, and in situ hybridization with an FER probe showed that the gene was located at 5q11-23 (Morris et al., Cytogenet. Cell. Genet., Vol. 53, p. 4, (1990)). Because of the potential role of this oncogene-related gene in neoplasia, we decided to evaluate it further with regards to the FAP locus. A human genomic clone from FER was isolated (MF 2.3) and used to define a restriction fragment length polymorphism (RFLP), and the RFLP in turn used to map FER by linkage analysis using a panel of three generation families. This showed that FER was very tightly linked to previously defined polymorphic markers for the FAP locus. The genetic mapping of FER was complemented by physical mapping using the YAC clones derived from FER sequences (FIG. 1B). Analysis of YAC contig 1 showed that FER was within 600 kb of cosmid marker M5.28, which maps to within 1.5 Mb of cosmid L5.99 by PFGE of human genomic DNA. Thus, the YAC mapping results were consistent with the FER linkage data and PFGE analyses.

Contig 2: TB1—TB1 was identified through a cross-hybridization approach. Exons of genes are often evolutionarily conserved while introns and [intergenie] *intergenic* regions are much less conserved. Thus, it a human probe cross-hybridizes strongly to the DNA from the non-primate species, there is a reasonable chance that it contains exon sequences. Subclones of the cosmids shown in FIG. 1 were used to screen Southern blots containing rodent DNA samples. A subclones of cosmid N5.66 (p 5.66-4) was shown to strongly hybridize to rodent DNA, and this clone was used to screen cDNA libraries derived from normal adult colon and fetal liver. The ends of the initial cDNA clones obtained in this screen were then used to extend the cDNA sequence. Eventually, 11 cDNA clones were isolated, covering 2314 bp. The gene detected by these clones was named TB1. Sequence analysis of the overlapping clones revealed an open reading frame (ORF) that extended for 1302 bp starting from the most 5' sequence data obtained (FIG. 2A). If this entire open reading frame were translated, it would encode 434 amino acids (SEQ ID NO:5). The product of this gene was not globally homologous to any other sequence in the current database but showed two significant local similarities to a family of ADP,ATP carrier/translocator proteins and mitochondrial brown fat uncoupling proteins which are widely distributed from yeast to mammals. These conserved regions of TB1 (underlined in FIG. 2A) may define a predictve motif for this sequence family. In addition, TB1 appeared to contain a signal peptide (or mitochondrial targeting sequence) as well as at least 7 transmembrane domains.

Contig 3: MCC, TB2, SRP and APC—The MCC gene was also discovered through a cross-hydridization approach, as described previously (Kinzler et al., Science Vol. 251, p. 1366 (1991)). The MCC gene was considered a candidate for causing FAP by virtue of its tight genetic linkage to FAP susceptibility and its somatic mutation in sporadic colorectal carcinomas. However, mapping experiments suggested that the ceding region of MCC was approximately 50 kb to proximal to the centromeric end of a 200 kb deletion found in an FAP patient. MCC cDNA probes detected a 10 mb mRNA transcript on Northern blot analysis of which 4151 bp, including the entire open reading frame, have been cloned. Although the 3' non-translated portion or an alternatively spliced form of MCC might have extended into this deletion, it was possible that the deletion did not affect the MCC gene product. We therefore used MCC sequences to initiate a YAC contig, and subsequently used the YAC clones to identify genes 50 to 250 kb distal to MCC that might be contained within the deletion.

In a first approach, the insert from YAC24ED6 (FIG. 1B) was radiolabelled and hybridized to a cDNA library from normal colon. One of the cDNA clones (YS39) identified in this manner detected a 3.1 kb mRNA transcript when used as a probe for Northern blot hybridization. Sequence analysis of the YS39 clone revealed that it encompassed 2283 nucleotides and contained an ORF that extended for 555 bp from the most 5' sequence data obtained. If all of this ORF were translated, it would encode 185 amino acids (SEQ ID NO:6) (FIG. 2B). The gene detected by YS39 was named TB2. Searches of nucleotide and protein database revealed that the TB2 gene was not identical to any previously reported sequences nor were there any striking similarities.

Another clone (YS11) identified through the YAC 24ED6 screen appeared to contain portions of two distinct genes. Sequences from one end of YS11 were identical to at least 180 bp of the signal recognition particle protein SRP19 (Lingelbach et al. Nucleic Acids Research, Vol. 16, p. 9431 (1988). A second ORF, from the opposite end of clone YS11, proved to be identical to 78 bp of a novel gene which was independently identified through a second YAC-based approach. For the latter, DNA from yeast cells containing YAC 14FH1 (FIG. 1B) was digested with EcoRI and subcloned into a plasmid vector. Plasmids that contained human DNA fragments were selected by colony hybridization using total human DNA as a probe. These clones were then used to search for cross-hybridizing sequences as described above for TB1, and the cross-hybridizing clones were subsequently used to screen cDNA libraries. One of the cDNA clones discovered in this way (FH38) contained a long ORF (2496 bp), 78 bp of which were identical to the above-noted sequences in YS11. The ends of the FH38 cDNA clone were then used to initiate cDNA walking to extend the sequence. Eventually, 85 cDNA clones were isolated from normal colon, brain and liver cDNA libraries and found to encompass 8973 nucleotides of contiguous transcript. The gene corresponding to their transcript was named APC. When used as probes for Northern blot analysis, APC cDNA clones hybridized to a single transcript of approximately 9.5 kb, suggesting that the great majority of the gene product was represented in the cDNA clones obtained. Sequences from the 5' end of the APC gene were found in YAC 37HG4 but not in YAC 14H1. However, the 3' end of the APC gene was found in 14FH1 as well as 37HG4. Analogously, the 5' end of the MCC ceding region was found in YAC clones 19AA9 and 266C3 but not 24ED6 or 14FH1, while the 3' end displayed the opposite pattern. Thus, MCC and APC transcription units pointed in opposite directions, with the direction of transcription going from centromeric to telometric in the case of MCC, and telomeric to centromeric in the case of APC. PFGE analysis of YAC DNA digested with various restriction endonucleases showed that TB2 and SRP were between MCC and APC, and that the 3' ends of the ceding regions of MCC and APC were separated by approximately 150 kb (FIG. 1B).

Sequence analysis of the APC cDNA clones revealed an open reading frame of 8,535 nucleotides. The 5' end of the ORF contained a methionine codon (codon 1) that was preceded by an in-frame stop codon 9 bp upstream, and the 3' end was followed by several in-frame stop codons. The protein produced by initiation at codon 1 would contain [2,842] *2843* amino acids (SEQ ID NO:7) [(FIG. 3)] *FIG. 3A-3Z*. The results of database searching with the APC gene product were quite complex due to the presence of large segments with locally biased amino acid compositions. In spite of this, APC could be roughly divided into two domains. The N-terminal 25% of the protein had a high content of leucine residue (12%) and showed local sequence similarities to myosins, various intermediate filament proteins (e.g., desmin, vimentin, neuroflilaments) and Drospophila armadillo/human plakeoglobin. The latter protein is a component of adhesive junctions (desmosomes) joining epithelial cells (Franke et al., Proc. Natl. Acad. Sci. U.S.A., Vol. 86, p. 4027 (1989); Perfer et al., Cell, Vol. 63, p. 1167 (1990)) The C-terminal 75% of APC (residues 731–2832) is 17% serine by composition with serine residues more or less uniformly distributed. This large domain also contains local concentrations of charged (mostly acidic) and proline residues. There was no indication of potential signal peptide, transmembrane regions, or nuclear targeting signals in APC, suggesting a cytoplasmic localization.

To detect short similarities to APC, a database search was performed using the PAM-40 matrix (Altschul. J. Mol. Biol., Vol. 219, p. 555 (1991). Potentially interesting matches to several proteins were found. The most suggestive of these involved the ral2 gene product of yeast, which is implicated in the regulation of ras activity (Fukul et al., Mol. Cell. Biol., Vol. 9, p. 5617 (1989)). Little is known about how ral2 might interact with rts but it is interesting to note the positively-charged character of this region in the context of the negatively-charged GAP interaction region of ras. A specific electrostatic interaction between ras and GAP-related proteins has been proposed.

Because of the proximity of the MCC and APC genes, and the fact that both [am] *are* implicated in colorectal tumorigenesis, we searched for similarities between the two predicted proteins. Bourne has previously noted that MCC has the potential to form alpha helical coiled coils (Nature, Vol. 351, p. 188 (1991). Lupas and colleagues have recently developed a program for predicting coiled coil potential from primary sequence data (Science, Vol. 252, p. 1162 (1991) and we have used their program to analyze both MCC and APC. Analysis of MCC indicated a discontinuous pattern of coiled-coil domains separated by putative "hinge" or "sparcer" regions similar to those seen in laminin and other intermediate filament proteins. Analysis of the APC sequence revealed two regions in the N-terminal domain which had strong coiled coil-forming potential, and these regions corresponded to those that showed local similarities with myosin and IF proteins on database searching. In addition, one other putative coiled coil region was identified in the central region of the APC. The potential for both APC and MCC to form coiled coils is interesting in that such structures often mediate homo- and [hetero-oligomerization] *heterooligomerization.*

Finally, it had previously been noted that MCC shared a short similarity with the region of the m3 muscarinic acetylcholine receptor (mAChR) known to regulate specificity of G-protein coupling. The APC gene also contained a local similarity to the region of the m3 mAChR (SEQ ID NO:9) that overlapped with the MCC similarity (SEQ ID NO:10) (FIG. 4B). Although the similarities to ral2 (SEQ ID NO:8) (FIG. 4A) and m3 mACHR (SEQ ID NO:9) (FIG. 4B) were not statistically significant, they were intriguing in light of previous observations resulting G-proteins to neoplasia.

Each of the six genes described above was expressed in normal colon mucosa, as indicated by their representation in colon cDNA libraries. To study expression of the genes in neoplastic colorectal epithelium, we employed reverse transcription-polymerase chain reaction (PCR) assays. Primers based on the sequences of FER, TB1, TB2, MCC, and APC were each used to design primers for PCR performed with cDNA templates. Each of these genes was found to be expressed in normal colon, in each of ten cell lines derived from colorectal cancers, and in tumor cell lines derived from lung and bladder tumors. The ten colorectal cancer cell lines included eight from patients with sporadic CRC and two from patients with FAP.

EXAMPLE 2

This example demonstrates a genetic analysis of the role of the FER gene in FAP and sporadic colorectal cancers.

We considered FER as a candidate because of its proximity to the FAP locus as judged by physical and genetic criteria (see Example 1), and its homology to known tyrosine kinases with oncogenic potential. Primers were designed to PCR-amplify the complete coding sequence of FER from the RNA of two colorectal cancer cell lines derived from FAP patients. cDNA was generated from RNA and used as a template for PCR. The primers used were 5'-AGAAGGATCCCTTGTGCAGTGTGGA-3' (SEQ ID NO:95) and 5'-GACAGGATCCTGAAGCTGAGTTTG-3' (SEQ ID NO:96). The underlined nucleotides were altered from the true FER sequence to create BamHI sites. The cell lines used were JW and Difi, both derived from colorectal cancers of FAP patients. (C. Parkaskeva, B. G. Buckle, D. Sheer, C. B. Wigley, Int. J. Cancer 34, 49 (1984); M. E. Gross et al., Cancer Res. 51, 1452 (1991). The resultant 2554 basepair fragments were cloned and sequences in their entirety. The PCR products were cloned in the BamHI site of Bluescript SK (Stratagene) and pools of at least 50 clones were sequenced en masse using T7 polymerase, as described in Nigro et al., Nature 342, 705 (1989).

Only a single conservative amino acid change (GTG→CTG, creating a val to leu substitution at codon 439) was observed. The region surrounding this codon was then amplified from the DNA of individuals without FAP and this substitution was found to be a common polymorphism, not specifically associated with FAP. Based on these results, we considered it unlikely (though still possible) the FER gene was responsible for FAP. To amplify the regions surrounding codon 439, the following primers were used: 5'-TCAGAAAGTGCTGAAGAG-3' (SEQ ID NO:97) and 5'-GGAATAATTAGGTCTCCAA-3' (SEQ ID NO:98). PCR products were digested with PstI, which yields a 50 bp fragment if codon 439 is leucine, but 26 and 24 bp fragments if it is valine. The primers used for sequencing were chosen from the FER cDNA sequence in Hao et al., supra.

EXAMPLE 3

This example demonstrates the genetic analysis of MCC, TB2, SRP and ACP in FAP and sporadic colorectal tumors. Each of these genes is linked and encompassed by contig 3 (see FIG. 1).

Several lines of evidence suggested that this contig was of particular interest. First, at least three of the four genes in this contig were within the deleted region identified in two FAP patients. (See Example 5 infra.) Second, allelic deletions of chromosome 5q21 in sporadic cancers appeared to be centered in this region. (Ashton-Rickardt et al., Oncogene, in press; and Miki et al., Japn. J. Cancer Res., in press.) Some tumors exhibited loss of proximal RFLP markers (up to and potentially including the 5' end of MCC), but no loss of markers distal to MCC. Other tumors exhibited loss of markers distal to and perhaps including the 3' end of MCC, but no loss of sequences proximal to MCC. This suggested either that different ends of MCC were affected by loss in all such cases, or alternatively, that two genes (one proximal to and perhaps including MCC, the other distal to MCC) were separate targets of deletion. Third, clones from each of the six FAP region genes were used as probes on Southern blots containing tumor DNA from patients with Sporadic CRC. Only two examples of somatic changes were observed in over 200 tumors studied; a rearrangement/deletion whose centromeric end was located within the MCC gene (Kinzler et al., supra) and an 800 bp insertion within the APC gene between nucleotides 4424 and 5584. Fourth, point mutations of MCC were observed in two tumors (Kinzler et al.) supra strongly suggesting that MCC was a target of mutation in at least some sporadic colorectal cancers.

Based on these results, we attempted to search for subtle alterations of contig 3 genes in patients with FAP. We chose to examine MCC and APC, rather than TB2 or SRP, because of the somatic mutations in MCC and APC noted above. To facilitate the identification of subtle alteration, the genomic sequences of MCC and APC exons were determined (see Table I, SEQ ID NO:24–38).

TABLE I

APC EXONS

| EXON NUCLEOTIDES[1] | EXON BOUNDARY SEQUENCE[2] |
|---|---|
| 822 to 930 | catgatgttatctgtatttacctatagtctaaattataccatctataatgtgcttaatttttag/GGTTAA . . . (SEQ ID NO:24) |
| | . . . ACCAAG/gtaacagaagattacaaaccctggtcactaatgccatgactactttgctaag (SEQ ID NO:25) |
| 931 to 1309 | ggatattaagtcgtaattttgtttctaaactcatttggcccacag/GTGGAA . . . (SEQ ID NO:26) |
| | . . . ATCCAA/gtatgttctctatagtgtacattcgtagtgcatg (SEQ ID NO:27) |
| 1310 to 1405 | catcattgctcttcaaataacaaagcattatggtttatgttgatttatttttcag/TGCCAG . . . (SEQ ID NO:28) |
| | . . . AACTAG/gtaagacaaaaatgtttttaatgacatagacaattactggtg (SEQ ID NO:29) |
| 1406 to 1545 | tagatgattgtctttttcctcttgccctttttaaattag/GGGGAC . . . (SEQ ID NO:30) |
| | . . . AACAAG/gtatgtttttataacatgtatttcttaaggatagctcaggtatga (SEQ ID NO:31) |
| 1546 to 1623 | gcttggcttcaagttgtctttttaatgatcctctattctgtatttaatttacag/GCTACG . . . (SEQ ID NO:32) |
| | . . . CAGCAG/gtactatttagaatttcacctgtttttctttttctcttttctttgaggcagggtctcactctg (SEQ ID NO:33) |
| 1624 to 1740 | gcaactagtatgattttatgtataaattaatctaaaattgatttgacag/GTTATT . . . (SEQ ID NO:34) |
| | . . . AAAAAG/gtacctttgaaaacatttagtactataatatgaatttcatgt (SEQ ID NO:35) |
| 1741 to 1955 | caactctaattagatgacccatattcagaaacttactag/GAATCA . . . (SEQ ID NO:36) |
| | . . . CCACAG/gtatatatagagttttatattacttttaaagtacagaattcatactctcaaaaa (SEQ ID NO:37) |
| 1956 to 8973 | tcttgatttttatttcag/GCAAAT . . . (SEQ ID NO:38) |
| | . . . GGTATTTATGCAAAAAAAAATGTTTTTGT (SEQ ID NO:1) |

[1]Relative to predicted translation initiation site

[2]Small case letters represent introns, large case letters represent exons

The entire 5' end of the cloned APC cDNA (at 1956–8973) appeared to be encoded in this exon, as indicated by restriction endonuclease mapping and sequencing of the cloned genomic DNA. The ORF ended at nt 8535. The extreme 3' end of the APC transcript has not yet been identified.

These sequences were used to design primers for PCR analysis of constitutional DNA from FAP patients.

We first amplified eight exons and surrounding introns of the MCC gene in affected individuals from 90 different FAP kindreds. The PCR products were analyzed by a ribonuclease (RNase) protein assay. In brief, the PCR products were hybridized to in vitro transcribed RNA probes representing the normal genomic sequences. The hybrids were digested with RNase A, which can cleave at single base pair mismatches within DNA-RNA hybrids, and the cleavage products were visualized following denaturing gel electrophoresis. Two separate RNase protection analyses were performed for each exon, one with the sense and one with the antisense strand. Under these conditions, approximately 40% of all mismatches are detectable. Although some amino acid variants of MCC were observed in FAP patients, all such variants were found in a small percentage of normal individuals. These variants were thus unlikely to be responsible for the inheritance of FAP.

We next examined three exons of the [A PC] *APC* gene. The three exons examined included those containing nt 822–930, 931–1309, and the first 300 nt of the most distal exon (nt 1956–2256). PCR and RNase protection analysis were performed as described in Kinzler et al. supra, using the primers underlined in Table I (SEQ ID NO:24–38). The primers for nt 1956–2256 were 5'-GCAAATCCTAAGAGAGAACAA-3' (SEQ ID NO:99) and 5'-GATGGCAAGCTTGAGCCAG-3' (SEQ ID NO:100).

In 90 kindreds, the RNase protection method was used to screen for mutations and in an additional 13 kindreds, the PCR products were cloned and sequenced to search for mutations not detectable by RNase protection. PCR products were cloned into a Bluescript vector modified as described in T. A. Holton and M. W. Graham, Nucleic Acid Res. 19, 1156 (1991). A minimum of 100 clones were pooled and sequenced. Five variants were detected among the 103 kindreds analyzed. Cloning and subsequent DNA sequencing of the PCR product of patient P21 indicated a C to T transition in codon 413 that resulted in a change from arginine to cysteine. This amino acid variant was not observed in any of 200 DNA samples from individuals without FAP. Cloning and sequencing of the PCR product from patients P24 and P34, who demonstrated the same abnormal RNase protection pattern indicated that both had a C to T transition at codon 801 that resulted in a change from arginine (CGA) to a stop codon (TGA). This change was not present in 200 individuals without FAP. As this point mutation resulted in the predicted loss of the recognition site for the enzyme Taq I, appropriate PCR products could be digested with Taq I to detect the mutation. This allowed us to determine that the stop codon [co-segregated] *cosegregated* with disease phenotype in members of the family of P24. The inheritance of this change in affected members of the pedigree provides additional evidence for the importance of the mutation.

Cloning and sequencing of the PCR product from FAP patient P93 indicated a C to G transversion of codon 279, also resulting in a stop codon (change from TCA to TGA). This mutation was not present in 200 individuals without FAP. Finally, one additional mutation resulting in a serine (TCA) to stop codon (TGA) at codon 712 was detected in a single patient with FAP (patient P60).

The five germline mutations identified are summarized in Table IIA, as well as four others discussed in Example 9.

TABLE IIA

Germline mutations of the APC gene in FAP and GS Patients

| EXTRA-COLONIC PATIENT DISEASE | CODON | NUCLEOTIDE CHANGE | AMINO ACID CHANGE | AGE | |
|---|---|---|---|---|---|
| 93 | 279 | TCA->TGA | Ser->Stop | 39 | Mandibular |
| Osteoma | | | | | |
| 24 | 301 | CGA->TGA | Arg->Stop | 46 | None |

TABLE IIA-continued

Germline mutations of the APC gene in FAP and GS Patients

| EXTRA-COLO-NIC PATIENT DISEASE | CODON | NUCLEO-TIDE CHANGE | AMINO ACID CHANGE | AGE | |
|---|---|---|---|---|---|
| 34 | 301 | CGA->TGA | Arg->Stop | 27 | Des-moid |
| Tumor | | | | | |
| 21 | 413 | CGC->TGC | Arg->Cys | 24 | Mandi-bular |
| Osteoma | | | | | |
| 60 | 712 | TCA->TGA | Ser->Stop | 37 | Mandi-bular |
| Osteoma | | | | | |
| 3746 | 243 | CAGAG->CAG | splice-junction | | |
| 3460 | 301 | CGA->TGA | Arg->Stop | | |
| 3827 | 456 | CTTTCA->CTTCA | frameshift | | |
| 3712 | 500 | T->G | Tyr->Stop | | |

*The mutated nucleotides are underlined.

In addition to these germline mutations, we identified several somatic mutations of MCC and APC in sporadic [CRC's S] CRC'*CRCs*. Seventeen MCC exons were examined in 90 sporadic colorectal cancers by RNAse protection analysis. In each case where an abnormal RNAse protection pattern was observed, the corresponding PCR products were cloned and sequenced. This led to the identification of six point mutations (two described previously) (Kinzler et al., supra), each of which was not found in the germline of these patients (Table IIB).

TABLE IIB

Somatic Mutations in Sporadic CRC Patients

| PATIENT | CODON[1] | NUCLEOTIDE CHANGE | AMINO ACID CHANGE |
|---|---|---|---|
| T35 | MCC 12 | GAG/gtaaga->GAG/gtaaaa | (Splice Donor |
| T16 | MCC 145 | ctcag/GGA->atcag/GGA | (Splice Acceptor |
| T47 | MCC 267 | CGG->CTG | Arg->Leg |
| T81 | MCC 490 | TCG->TTG | Ser->Leu |
| T35 | MCC 506 | CGG->CAG | Arg->Gln |
| T91 | MCC 698 | GCT->GTT | Ala->Val |
| T34 | APC 288 | CCAGT->CCCAGCCAGT | (Insertion) |
| T27 | APC 331 | CGA->TGA | Arg->Stop |
| T135 | APC 437 | CAA/gtaa->CAA/gcaa | (Splice Donor) |
| T20I | APC 1338 | CAG->TAG | Gln->Stop |

For splice site mutations, the codon nearest to the mutation is listed
The underlined nucleotide were mutated; small case letters represent introns, large case letters represent exons Four of the mutations resulted in amino acid substitutions and two resulted in the alteration of splice site consensus elements. Mutations at analogous splice site positions in other genes have been shown to alter RNA processing in vivo and in vitro.

Three exons of APC were also evaluated in sporadic tumors. Sixty tumors were screened by RNase protection, and an additional 98 tumors were evaluated by sequencing. The exons examined included nt 822–930, 931–1309, and 1406–1545 (Table I). A total of three mutations were identified, each of which proved to be somatic. Tumor T27 contained a somatic mutation of CGA (arginine) to TGA (stop codon) at codon 33. Tumor T135 contained a GT to GC change at a splice donor site. Tumor T34 contained a 5 bp insertion (CAGCC between codons 288 and 289) resulting in a stop at codon 291 due to a frameshift.

We serendipitously discovered one additional somatic mutation in a colorectal cancer. During our attempt to define the sequences and splice patterns of the MCC and APC gene products in colorectal epithelial cells, we cloned cDNA from the colorectal cancer cell line SW480. The amino acid sequence of the MCC gene from SW480 was identical to that previously found in clones from human brain. The sequence of APC in SW480 cells, however, differed significantly, in that a transition at codon 1338 resulted in a change from glutamine (CAG) to a stop codes (TAG). To determine if this mutation was somatic, we recovered DNA from archival paraffin blocks of the original surgical specimen (T201) from which the tumor cell line was derived 28 years ago.

DNA was purified from paraffin sections as described in S. E. Goelz, S. R. Hamilton, and B. Vogelstein. Biochem. Biophys. Res. Comm. 130, 118 (1985). PCR was performed as described in reference 24, using the primers 5'-GTTCCAGCAGTGTCACAG-3' (SEQ ID NO:101) and 5'-GGGAGATTTCGCTCCTGA-3' (SEQ ID NO:102). A PCR product containing codon 1338 was amplified from the archival DNA and used to show that the stop codon represented a somatic mutation present in the original primary tumor and in cell lines derived from the primary and metastic tumor sites, but not from normal tissue of the patient.

The ten point mutation in the MCC and APC genes so far discovered in sporadic. CRCs are summarized in Table IIB. Analysis of the number of mutant and wild-type PCR clones obtained from each of these tumors showed that in eight of the ten cases, the wild-type sequence was present in approximately equal proportions to the mutant. This was confirmed by RFLP analysis using flanking markers from chromosome 5q was demonstrated that only two of the ten tumors (T135 and T201) exhibited an allelic deletion on chromosome 5q. These results are consistent with previous observations showing that 20–40% of sporadic colorectal tumors had allelic deletions of chromosome 5q. Moreover, these data suggest that mutations of 5q21 genes are not limited to those colorectal tumors which contain allelic deletions of this chromosome.

EXAMPLE 4

This example characterizes small, nested deletions in DNA from two unrelated FAP patients.

DNA from 40 FAP patients was screened with cosmids that has been mapped into a region near the APC locus to identify small deletions or rearrangements. Two of these cosmids, L5.71=nd L5.79, hybridized with a 1200 kb NotI fragment in DNAs from most of the FAP patients screened.

The DNA of one FAP patient, 3214 showed only a 940 kb NotI fragment instead of the expected 1200 kb fragment. DNA was analyzed from four other members of the patient's immediate family; the 940 kb fragment was present in her affected mother (4711), but not in the other, unaffected family members. The mother also carried a normal 1200 kb Not1 fragment that was transmitted to her two unaffected offspring. These observations indicated that the mutant polyposis allele is on the same chromosome as the 940 kb Not1 fragment. A simple interpretation is that APC patients 3214 and 4711 each carry a 260 kb deletion within the APC locus.

If a deletion were present, then other enzymes might also be expected to produce fragments with altered mobilities. Hybridization of L5.79 to NruI-digested DNAs from both affected members of the family revealed a novel NruI fragment of 1300 kb, in addition to the normal 1200 kb NruI fragment. Furthermore, M1u1 fragments in patients 3214 and 4711 also showed an increase in size consistent with the deletion of an M1uI site. The two chromosome 5 homologs of patient 3214 were segregated in somatic cell hybrid lines; HHW1155 (deletion hybrid) carried the abnormal homolog and HHW1159 (normal hybrid) carried the normal homolog.

Because patient 8214 showed [bray] *only* a 940 kb NotI fragment, she had not inherited the 1200 kb fragment present in the unaffected father's DNA. This observation suggests that he must be heterozygous for, and have transmitted, either a decision of the L5.79 probe region or a variant NotI fragment too large to resolve on the gel system. As expected, the hybrid cell line HHW1159, which carries the paternal homolog, revealed no resolved Not fragment when probed with L5.79. However, probing of HHW1159 DNA with L5.79 following digestion with other enzymes did reveal restriction fragments, demonstrating the presence of DNA homologous to the probe. The father is, therefore, interpreted as heterozygous for a polymorphism at the NotI site, with one chromosome 5 having a 1200 kb NotI fragment and the other having a fragment too large to resolve consistently on the gel. The latter was transmitted to patient 3214.

When double digests were used to order restriction sites within the 1200 kb NotI fragment, L5.71 and L5.79 were [beth] *both* found to lie on a 550 kb NotI-NruI fragment and, therefore, on the same side of an NruI site in the 1200 kb NotI fragment. To obtain genomic representation of sequences present over the entire 1200 kb NotI fragment, we constructed a library of small-fragment inserts enriched for sequences from this fragment. DNA from the somatic cell hybrid HHW141, which contains about 40% of chromosome 5, was digested with NotI and electrophoresed under pulsed-field gel (PPG) conditions; EcoRI fragments from the 1200 kb region of this gel were cloned into a phage vector. Probe Map30 was isolated from this library. In normal individuals probe Map30 hybridizes to the 1200 kb NotI fragment and to a 200 kb NruI fragment. This latter hybridization places Map30 distal, with respect to the locations of L5.71 and L5.79, to the NruI site of the 550 kb NotI-NruI fragment.

Because Map30 hybridized to the abnormal, 1300 kb Nru1 fragment of patient 3214, the locus defined by Map30 lies outside the hypothesized deletion. Furthermore, in normal chromosomes Map30 identified a 200 kb NruI fragment and L5.79 identified a 1200 kb NruI fragment; the hypothesized deletion must, therefore, be removing an NruI site, or sites, lying between Map30 and L5.79, and these two probes must flank the hypothesized deletion. A restriction map of the genomic region, showing placement of these probes, is shown in FIG. 5.

A NotI digest of DNA from another FAP patient, 3824, was probed with L5.79. In addition to the 1200 kb normal NotI fragment, a fragment of approximately 1100 kb was observed, consistent with the presence of a 100 kb deletion in one chromosome 5. In this case, however, digestion with NruI and M1uI did not reveal abnormal bands, indicating that if a deletion were present, its boundaries must lie distal to the NruI and M1uI sites of the fragments identified by L5.79. Consistent with this expectation, hybridization of Map30 to DNA from patient 3824 identified a 760 kb M1uI fragment in addition to the expected 860 kb fragment, supporting the interpretation of a 100 kb deletion in this patient. The two chromosome 5 homologs of patient 3824 were segregated in somatic cell hybrid lines; HHW1291 was found to carry only the abnormal homolog and HHW1290 only the normal homolog.

That the 860 kb M1u1 fragment identified by Map30 is distinct from the 830 kb M1uI fragment identified previously by L5.79 was demonstrated by hybridization of Map30 and L5.79 to a NotI-M1uI double digest of DNA from the hybrid cell (HHWW1159) containing the nondeleted chromosome 5 homolog of patient 3214. As previously indicated, this hybrid is interpreted as missing one of the NotI sites that define the 1200 kb fragment. A 620 kb NotI-M1uI fragment was seen with probe L5.79, and an 860 kb fragment was seen with Map30. Therefore, the 830 kb M1uI fragment recognized by probe L5.79 must contain a NotI site in HHW1159 DNA; because the 800 kb M1uI fragment remains intact, it does not carry this NotI site and must be distinct from the 830 kb M1u1 fragment.

EXAMPLE 5

This example demonstrates the isolation of human sequences which span the region deleted in the two unrelated FAP patients characterized in Example 4.

A strong prediction of the hybridization that patients 8214 and 3824 carry deletions is that some sequences present on normal chromosome 5 homologs would be missing from the hypothesized deletion homologs. Therefore, to develop genomic probes that might confirm the deletions, as well as to identify genes from the region, YAC clones from a contig seeded by cosmid L5.79 were localized from a library containing seven haploid human genome equivalents (Albertsen et al., Proc. Natl. Acad. Sci. U.S.A., Vol. 87, pp. 4256–4260 (1990)) with respect to the hypothesized deletions. Three clones, YACs 57B8, 310D8, and 183H12, were found to overlap the deleted regions.

Importantly, one end of YAC 57B8 (clone AT57) was found to lie within the patient 3214 deletion. Inverse polymerase chain reaction (PCR) defined the end sequences of the insert of YAC 57b8. PCR primers based on one of these end sequences repeatedly failed to amplify DNA from the somatic cell hybrid (HHW1155) carrying the deleted homolog of patient 3214, but did amplify a product of the expected size from the somatic cell hybrid (HHWW1159) carrying the normal chromosome 5 homolog. This result support the interpretation that the abnormal restriction fragments found in the DNA of patient 3214 result from a deletion.

Additional support for the hypothesis of deletions in DNA from patient 3214 came from subcloned fragments of YAC 183H12, which spans the region in question. Y11, an EcoRI fragment cloned from YAC 183H12, hybridized to the normal, 1200 kb NotI fragment of patient 4711, but failed to hybridize to the abnormal, 940 kb NotI fragment of 4711 or to DNA from deletion cell line HHW1155. This result confirmed the deletion in patient 3214.

Two additional EcoR1 fragments from YAC 183H12. Y10 and Y14, were localized within the patient 3214 deletion by their failure to hybridize to DNA from HHW1155. Probe Y10 hybridizes to a 150 kb NruI fragment in normal chromosome 5 homologs. Because the 3214 deletion creates the 1300 kb NruI fragment seen with the probes L5.79 and Map30 that flank the deletion, these NruI sites and the 150 kb NruI fragment lying between must be deleted in patient 3214. Furthermore, probe Y10 hybridizes to the same 620 kb NotI-M1uI fragment seen with probe L5.79 in normal DNA, indicating its location as L5.79-proximal to the deleted M1uI site and placing it between the M1uI site and the L5.79-proximal NruI site. The M1uI site must, therefore, lie between the NruI sites that define the 150 kb NruI fragment (see FIG. 5).

Probe Y11 also hybridized to the 150 kb NruI fragment in the normal chromosome 5 homolog, but failed to hybridize to the 620 Kb Not1-M1uI fragment, placing it L5.79-distal to the M1uI site, but proximal to the second NruI site. Hybridization to the same (860 kb) M1uI fragment as Map30 confirmed the localization of probe Y11 L5.79-distal to the M1uI site.

Probe Y14 was shown to be L5.79-distal to both deleted NruI sites by virtue of its hybridization to the same 200 kb NruI fragment of the normal chromosome 5 seen with Map30. Therefore, the order of these EcoRI fragments derived from YAC 183H12 and deleted in patient 3214, with respect to L5.79 and Map30, is L5.79-Y10-Y11-Y14-Map30.

The 100 kb deletion of patient 3284 was confirmed by the failure of aberrant restriction fragments in this DNA to hybridize with probe Y11, combined with positive hybridizations to probes Y10 and/or Y14. Y10 and Y14 each hybridized to the 1100 kb NotI fragment of patient 3824 as well as to the normal 1200 kb NotI fragment, but Y11 hybridized to the 1200 kb fragment only. In the M1u1 digest, probe Y14 hybridized to the 860 kb and 760 kb fragments of patient 3824 DNA, but probe Y11 hybridized only to the 860 k13 fragment. We conclude that the basis for the alteration in fragment size in DNA from patient 3824 is, indeed, a deletion. Furthermore, because probes Y10 and Y14 are missing from the deleted 3214 chromosome, but present on the deleted 3824 chromosome, and they have been shown to flank probe Y11, the deletion in patient 3824 must be nested within the patient 3214 deletion.

Probes Y10, Y11, Y14 and Map30 each hybridized to YAC 310D8, indicating that this YAC spanned the patient 3824 deletion and at a minimum, most of the 3214 deletion. The YAC characterizations, therefore, confirmed the presence of deletions in the patients and provided physical representation of the deleted region.

EXAMPLE 6

This example demonstrates that the MCC coding sequence maps outside of the region deleted in the two FAP patients characterized in Example 4.

An intriguing FAP candidate gene, MCC, recently was ascertained with cosmid L5.71 and was shown to have undergone mutation in colon carcinomas (Kinzler et al., supra). It was therefore of interest to map this gene with respect to the deletions in APC patients. Hybridization of MCC probes with an overlapping series of YAC clones extending in either direction from L5.71 showed that the 3' end of MCC must be oriented toward the region of the two APC deletions.

Therefore, two 3' cDNA clones from MCC were mapped with respect, to the deletions: clone 1CI (bp 2378–4181) and clone 7 (bp 2890–3560). Clone 1CI contains sequences from the C-terminal end of the open reading frame, which stops at nucleotide 2708, as well as 3' untranslated sequence. Clone 7 contains sequence that is entirely 3' to the open reading frame. Importantly, the entire 3' untranslated sequence contained in the cDNA clones consists of a single 2.5 kb exon. These two clones were hybridized to DNAs from the YACs spanning the FAP region. Clone 7 fails to hybridize to YAC 310D8, although it does hybridize to YACs 183H12 and 57B8; the same result was obtained with the cDNA 1CI. Furthermore, these probes did show hybridization to DNAs from both hybrid cell lines (HWW1159 and HWW1155) and the lymphoblastoid cell line from patient 3214, confirming their locations outside the deleted region. Additional mapping experiments suggested that the 3' end of the MCC cDNA clone coding is likely to be located more than 45 kb from the deletion of patient 3214 and, therefore, more than 100 kb from the deletion of patient 3824.

EXAMPLE 7

This example identifies three genes within the deleted region of chromosome 5 in two unrelated FAP patients characterized in Example 4.

Genomic clones were used to screen cDNA libraries in three separate experiments. One screening was done with a phage clone derived from YAC 310D8 known to span the 260 kb deletion of patient 3214. A large-insert phage library was constructed from this YAC; screening with Y11 identified λ205, which mapped within both deletions. When clone λ205 was used to probe a random-, plus oligo(dT)-, primed fetal brain cDNA library (approximately 300,000 phage), six cDNA clones were isolated and each of them mapped entirely within both deletions. Sequence analysis of these six clones formed a single cDNA contig, but did not reveal an extended open reading frame. One of the six cDNAs was used to isolate more cDNA clones, some of which crossed the L5.71-proximal breakpoint of the 3824 deletion, as indicated by hybridization to both chromosome of this patient. These clones also contained an open reading frame, indicating a transcriptional orientation proximal to distal with respect to L5.71. This gene was named DP1 (deleted in polyposis 1). This gene is identical to TB2 described above.

cDNA walks yielded a cDNA contig of 3.0–3.5 kb, and included two clones containing terminal poly(A) sequences. This size corresponds to the 3.5 kb band seen by Northern analysis. Sequencing of the first 3163 bp of the cDNA contig revealed an open reading frame extending from the first base to nucleotide 631, followed by a 2.5 kb 3' untranslated region. The sequence surrounding the methionine codon at base 77 conforms to the Kozak consensus of an initiation methionine (Kozak, 1984). Failed attempts to walk farther, coupled with the similarity of the lengths of isolated cDNA and mRNA, suggested that the NH2-terminus of the DP1 protein had been reached. Hybridization to a combination of genomic and YAC DNAs cut with various enzymes indicated the genomic coverage of DP1 to be approximately 30 kb.

Two additional probes for the locus, YS-11 and YS-39, which had been ascertained by screening of a cDNA library with an independent YAC probe identified with MCC sequences adjacent to L5.71, were mapped into the deletion region. YS-39 was shown to be a cDNA identical in sequence to DP1. Partial characterization of YS-11 had shown that 200 bp of DNA sequence at one end was identical to sequence coding for the 19 kd protein of the ribosomal signal recognition particle. SRP19 (Lingelbach et al., supra). Hybridization experiments mapped YS-11 within [beth] *both* deletions. The sequence of this clone, however, was found to be complex. Although 454 bp of the 1032 bp sequence of YS-11 were identical to the GenBank entry for the SRP19 gene, another 578 bp appended 5' to the SRP19 sequence was found to consist of previously unreported sequence containing no extended open reading frames. This suggested that YS-11 was either a chemeric clone containing two independent inserts or a clone of an incompletely processed or aberrant message. If YS-11 were a conventional chimeric clone, the independent segments would not be expected to map to the same physical region. The segments resulting from anomalous processing of a continuous transcript, however, would map to a single chromosomal region.

Inverse PCR with primers specific to the two ends of YS-11, the SRP19, end and the unidentified region, verified that both sequences map within the YAC 310D8; therefore, YS-11 is most likely a clone of an immature or anomalous mRNA species. Subsequently, both ends were shown to lie with the deleted region of patient 3824, and YS-11 was used to screen for additional cDNA clones.

Of the 14 cDNA clones selected from the fetal brain library, one clone, V5, was of particular interest in that it contained an open reading frame throughout, although it included only a short identity to the first 78 5' bases of the YS-11 sequence. Following the 78 bp of identical sequence, the two cDNA sequences diverged at an AG. Furthermore, divergence from genomic sequence was also seen after these 78 bp, suggesting the presence of a splice junction, and supporting the view that YS-11 represents an irregular message.

Starting with V5, successive 5' and 3' walks were performed; the resulting cDNA coding consisted of more than 100 clones, which defined a new transcript, DP2. Clones walking in the 5' direction crossed the 3824 deletion breakpoint farthest from L5.71; since its 3' end is closer to this cosmid than its 5' end, the transcriptional orientation of DP2 is opposite to that of MCC and DP1.

The third screening approach relied on hybridization with a 120 kb M1uI fragment with YAC 57B8. This fragment hybridizes with probe Y11 and completely spans the 100 kb deletion in patient 3824, the fragment was purified on two preparative PFGs labeled, and used to screen a fetal brain cDNA library. A number of cDNA clones previously identified in the development of the DP1 and DP2 contigs were reascertained. However, 19 new cDNA clones mapped into the patient 3824 deletion. Analysis indicated that these 19 formed a new contig, DP3, containing a large open reading frame.

A clone from the 5' end of this new cDNA contig hybridized to the same EcoRI fragment as the 3' end of DP2. Subsequently, the DP2 and DP3 contigs were connected by a single 5' walking step from DP3, to form the single contig DP2.5. The complete nucleotide sequence of DP2.5 is shown in FIG. 9.

The consensus cDNA sequence of DP2.5 suggests that the entire coding sequence of DP2.5 has been obtained and is 8532 bp long. The most 5' ATG codon occurs two codons from an in-frame stop and comforms to the Kozak initiation consensus (Kozak, Nucl. Acids. Res., Vol. 12, p. 857–872 1984). The 3' open reading frame breaks down over the final 1.8 kb, giving multiple stops in all frames. A poly(A) sequence was found in one clone approximately 1 kb into the 3' untranslated region, associated with a polyadenylation signal 33 bp upstream (position 9530). The open reading frame is almost identical to the identified as APC above.

An alternatively spliced exon at nucleotide 934 of the DP2.5 transcript of potential interest, it was first discovered by noting that two classes of cDNA had been isolated. The more abundant cDNA class contains a 303 bp exon not included in the other. The presence in vivo of the two transcripts was verified by an exon connection experiment. Primers flanking the alternatively spliced exon were used to amplify, by PCR, cDNA prepared from various adult tissues. Two PCR products that differed in size by approximately 300 bases were amplified from all the tissues tested; the larger product was always more abundant than the smaller.

EXAMPLE 8

This example demonstrates the primers used to identify subtle mutations in DP1, SRP19, and DP25.

To obtain DNA sequence adjacent to the exons of the genes DP1, DP2.5, and SRP19, sequencing substrate was obtained by inverse PCR amplification of DNAs from two YACs 310D8 and 183H12, that span the deletions. Ligation at low concentration cyclized the restriction enzyme-digested YAC DNAs. Oligonucleotides with sequencing tails, designed in inverse orientation at intervals along the cDNAs, primed PCR amplification form the cyclized templates. Comparison of these DNA sequences with the cDNA sequences placed exon boundaries at the divergence points. SRP19 and DP1 were each shown to have five exons. DP2.5 consisted of 15 exons. The sequences of the oligonucleotides synthesized to provide PCR amplification primers for the exons of each of these genes are listed in Table III [SEQ ID NO:39–94].

TABLE III

Sequence of Primers Used for SSCP Analyses

| Exon Primer 1 | | Primer 2 | |
|---|---|---|---|
| | | DP1 | |
| UP-TCCCCGCCTGCCGCTCTC | (SEQ ID NO:39) | RP-GCAGCGGCGGCTCCCGTG | (SEQ ID NO:40) |
| UP-GTGAACGGCTCTCATGCTGC | (SEQ ID NO:41) | RP-ACGTGCGGGGAGGAATGGA | (SEQ ID NO:42) |
| UP-ATGATATCTTACCAAATGATATAC | (SEQ ID NO:43) | RP-TTATTCCTACTTCTTCTATACAG | (SEQ ID NO:44) |
| UP-TACCCATGCTGGCTCTTTTTC | (SEQ ID NO:45) | RP-TGGGGCCATCTTGTTCCTGA | (SEQ ID NO:46) |
| UP-ACATTAGGCACAAAGCTTGCAA | (SEQ ID NO:47) | RP-ATCAAGCTCCAGTAAGAAGGTA | (SEQ ID NO:48) |
| | | SRP19 | |
| UP-TGCGGCTCCTGGGTTGTTG | (SEQ ID NO:49) | RP-GCCCCTTCCTTTCTGAGGAC | (SEQ ID NO:50) |
| UP-TTTTCTCCTGCCTCTTACTGC | (SEQ ID NO:51) | RP-ATGACACCCCCCATTCCCTC | (SEQ ID NO:52) |
| UP-CCACTTAAAGCACATATATTTAGT | (SEQ ID NO:53) | RP-GTATGGAAAATAGTGAAGAACC | (SEQ ID NO:54) |
| UP-TTCTTAAGTCCTGTTTTTCTTTTG | (SEQ ID NO:55) | RP-TTTAGAACCTTTTTTGTGTTGTG | (SEQ ID NO:56) |
| UP-CTCAGATTATACACTAAGCCTAAC | (SEQ ID NO:57) | RP-CATGTCTCTTACAGTAGTACCA | (SEQ ID NO:58) |
| | | DP2.5 | |
| UP-AGGTCCAAGGGTAGCCAAGG* | (SEQ ID NO:59) | RP-TAAAAATGGATAAACTACAATTAAAAG | (SEQ ID NO:60) |
| UP-AAATACAGAATCATGTCTTGAAGT | (SEQ ID NO:61) | RP-ACACCTAAAGATGACAATTTGAG | (SEQ ID NO:62) |
| UP-TAACTTAGATAGCAGTAATTTCCC* | (SEQ ID NO:63) | RP-ACAATAAACTGGAGTACACAAGG | (SEQ ID NO:64) |
| UP-ATAGGTCATTGCTTCTTGCTGAT* | (SEQ ID NO:65) | RP-TGAATTTTAATGGATTACCTAGGT | (SEQ ID NO:66) |
| UP-CTTTTTTTGCTTTTACTGATTAACG | (SEQ ID NO:67) | RP-TGTAATTCATTTTATTCCTAATACCTC | (SEQ ID NO:68) |
| UP-GGTAGCCATAGTATGATTATTTCT | (SEQ ID NO:69) | RP-CTACCTATTTTTATACCCACAAAC | (SEQ ID NO:70) |
| UP-AAGAAAGCCTACACCATTTTTGC | (SEQ ID NO:71) | RP-GATCATTCTTAGAACCATCTTGC | (SEQ ID NO:72) |
| UP-ACCTATAGTCTAAATTATACCATC | (SEQ ID NO:73) | RP-GTCATGGCATTACTGACCAG | (SEQ ID NO:74) |
| UP-AGTCGTAATTTTGTTTCTAAACTC | (SEQ ID NO:75) | RP-TGAAGGACTCCGATTTCACCC* | (SEQ ID NO:76) |
| UP-TCATTCACTCACAGCCTGATGAC* | (SEQ ID NO:77) | RP-GCTTTGAAACATGCACTACGAT | (SEQ ID NO:78) |
| UP-AAACATCATTGCTCTTCAAATAAC | (SEQ ID NO:79) | RP-TACCATGATTTAAAAATCCACCAG | (SEQ ID NO:80) |
| UP-GATGATTGTCTTTTTCCTCTTTGC | (SEQ ID NO:81) | RP-CTGAGCTATCTTAAGAAATACATG | (SEQ ID NO:82) |
| UP-TTTTAAATGATCCTCTATTCTGTAT | (SEQ ID NO:83) | RP-ACAGAGTCAGACCCTCCCTCAAAG | (SEQ ID NO:84) |
| UP-TTTCATATTCTTACTGCTAGCATT | (SEQ ID NO:85) | RP-ATACACAGGTAAGAAATTAGGA | (SEQ ID NO:86) |

TABLE III-continued

Sequence of Primers Used for SSCP Analyses

| Exon | Primer 1 | | Primer 2 | |
|---|---|---|---|---|
| | UP-TAGATGACCCATATTCTCTTTC | (SEQ ID NO:87) | RP-CAATTAGGTCTTTTTGAGAGTA | (SEQ ID NO:88) |
| 3-A | UP-GTTACTGCATACACATTGTGAC | (SEQ ID NO.89) | RP-GCTTTTTGTTTCGTAACATGAAG* | (SEQ ID NO:90) |
| B | UP-AGTACAAGGATGCCAATATTATG* | (SEQ ID NO:103) | RP-ACTTCTATCTTTTTCAGAACGAG* | (SEQ ID NO:104) |
| C | UP-ATTTGAATACTACAGTGTTACCC* | (SEQ ID NO:105) | RP-CTTGTATTCTAATTTGGCATAAGG* | (SEQ ID NO:106) |
| D | UP-CTGCCCATACACATTCAAACAC* | (SEQ ID NO:107) | RP-TGTTTGCGTCTTGCCCATCTT* | (SEQ ID NO:108) |
| E | UP-AGTCTTAAATATTCAGATGAGCAG* | (SEQ ID NO:109) | RP-GTTTCTCTTCATTATATTTTATGCTA* | (SEQ ID NO:110) |
| F | UP-AAGCCTACCAATTATAGTGAACG* | (SEQ ID NO:111) | RP-AGCTGATGACAAAGATGATAATC* | (SEQ ID NO:112) |
| G | UP-AAGAAACAATACAGACTTATTGTG* | (SEQ ID NO:113) | RP-ATGAGTGGGGTCTCCTGAAC* | (SEQ ID NO:114) |
| H | UPATCTCCCTCCAAAAGTGGTGC* | (SEQ ID NO:115) | RP-TCCATCTGGAGTACTTTCTGTG* | (SEQ ID NO:116) |
| I | UP-AGTAAATGCTGCAGTTCAGAGG* | (SEQ ID NO:117) | RP-CCGTGGCATATCATCCCCC* | (SEQ ID NO:118) |
| J | UP-CCCAGACTGCTTCAAAATTACC* | (SEQ ID NO:119) | RP-GAGCCTCATCTGTACTTCTGC* | (SEQ ID NO:120) |
| K | UP-CCCTCCAAATGAGTTAGCTGC* | (SEQ ID NO:121) | RP-TTGTGGTATAGGTTTTACTGGTG* | (SEQ ID NO:122) |
| L | UP-ACCCAACAAAAATCAGTTAGATG* | (SEQ ID NO:123) | RP-GTGGCTGGTAACTTTAGCCTC* | (SEQ ID NO:124) |
| N | UP-ATGATGTTGACCTTTCCAGGG* | (SEQ ID NO:125) | RP-ATTGTGTAACTTTTCATCAGTTGC* | (SEQ ID NO:126) |
| M | UP-AAAGACATACCAGACAGAGGG* | (SEQ ID NO:127) | RP-CTTTTTTGGCATTGCGGAGCT* | (SEQ ID NO:128) |
| O | UP-AAGATGACCTGTTGCAGGAATG* | (SEQ ID NO:129) | RP-GAATCAGACCAAGCTTGTCTAGAT* | (SEQ ID NO:130) |
| P | UP-CAATAGTAAGTAGTTTACATCAAG* | (SEQ ID NO:131) | RP-AAACAGGACTTGTACTGTAGGA* | (SEQ ID NQ:132) |
| Q | UP-CAGCCCCTTCAAGCAAACATC* | (SEQ ID NO:133) | RP-GAGGACTTATTCCATTTCTACC* | (SEQ ID NO:134) |
| R | UP-CAGTCTCCTGGCCGAAACTC* | (SEQ ID NO:135) | RP-GTTGACTGGCGTACTAATACAG* | (SEQ ID NO:136) |
| S | UP-TGGTAATGGAGCCAATAAAAAGG* | (SEQ ID NO:137) | RP-TGGGACTTTTCGCCATCCAC* | (SEQ ID NO:138) |
| T | UP-TGTCTCTATCCACACATTCGTC* | (SEQ ID NO:139) | RP-ATGTTTTTCATCCTCACTTTTGC* | (SEQ ID NO:140) |
| U | UP-GGAGAAGAACTGGAAGTTCATC* | (SEQ ID NO:141) | RP-TTGAATCTTTAATGTTTGGATTTGC* | (SEQ ID NO:142) |
| V | UP-TCTCCCACAGGTAATACTCCC | (SEQ ID NO:143) | RP-GCTACAACTGAATGGGGTACG | (SEQ ID NO:144) |
| W | UP-CAGGACAAAATAATCCTGTCCC | (SEQ ID NO:145) | RP-ATTTTCTTACTTTCATTCTTCCTC | (SEQ ID NO:146) |

All primers are read in the 5' to 3' direction, the first primer in each pair lies 5' of the exon it amplifies: the second primer lies 3' of the exon it amplifies. Primers that lie within the exon are identified by an asterisk. UP represents the 21M13 universal primer sequence[:]. RP represents the M13 reverse primer sequence.

With the exception of exons 1, 3, 4, 9, and 15 of DP2.5 (see below), the primer sequences were located in intron sequences flanking the exons. The 5' primer of exon 1 is complementary to the cDNA sequence, but extends just into the 5' Kozak consensus sequence for the initiator methionine, allowing a survey of the translated sequences. The 5' primer of exon 3 is actually in the 5' coding sequences of this exon, as three separate intronic primers simply would not amplify. The 5' primer of exon 4 just overlaps the 5' end of this exon, and we thus fail to survey the 19 most 5' bases of this exon. For exon 9, two overlapping primer sets were used, such that each had one end within the exon. For exon 15, the large 3' exon of DP2.5, overlapping primer pairs were placed along the length of the exon; each pair amplified a product of 250–400 bases.

EXAMPLE 9

This example demonstrates the use of single stranded conformation polymorphism (SSCP) analysis as described by Orita et al. Proc. Natl. Acad. Sci. U.S.A., Vol. 86, pp. 2766–70 (1989) and Genomics, Vol. 5, pp. 874–879 (1989) as applied to DP1, SRP19 and DP2.5.

SSCP analysis identifies most single- or multiple-base changes in DNA fragments up to 400 bases in length. Sequence alterations are detected as shifts in electrophoretic mobility of single-stranded DNA on nondenaturing acrylamide gels; the two complementary strands of DNA segment usually resolve as two SSCP conformers of distinct mobilities. However, if the sample is from an individual heterozygous for a base-pair variant within the amplified segment, often three or more bands are seen. In some cases, even the sample from a homozygous individual will show multiple bands. Base-pair-change variants are identified by differences in pattern among the DNAs of the sample set.

Exons of the candidate genes were amplified by PCR from the DNAs of 61 unrelated FAP patients and a control set of 12 normal individuals. The five exons from DP1 revealed no unique conformers in the FAP patients, although common conformers were observed with exons 2 and 3 in some individuals of both affected and control sets, indicating the presence of DNA sequence polymorphisms. Likewise, none of the five exons of SRP19 revealed unique conformers in DNA from FAP patients in the test panel.

Testing of exons 1 through 14 and primer sets A through N of exon 15, of the DP2.5 gene, however, revealed variant conformers specific to FAP patients in exons 7, 8, 10, 11, and 15. These variants were in the unrelated patients 3746, 3460, 3827, 3712, and 3751, respectively. The PCR-SSCP procedure was repeated for each of these exons in the five affected individuals and in an expanded set of 48 normal controls. The variant bands were reproducible in the FAP patients but were not observed in any of the control DNA samples. Additional variant conformers in exons 11 and 15 of the DP2.5 gene were seen; however, each of these was found in both the affected and control DNA sets. The five sets of conformers unique to the FAP patients were sequenced to determine the nucleotide changes responsible for their altered mobilities. The normal conformers from the host individuals were sequenced also. Bands were cut from the dried acrylamide gels, and the DNA was eluted. PCR amplification of these DNAs provided template for sequencing.

Figure 7A:
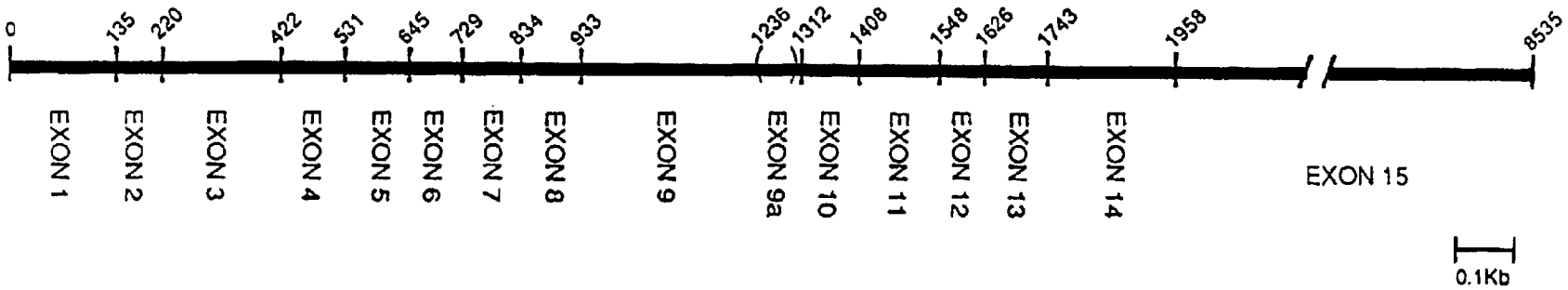
Figures 1, 7B:
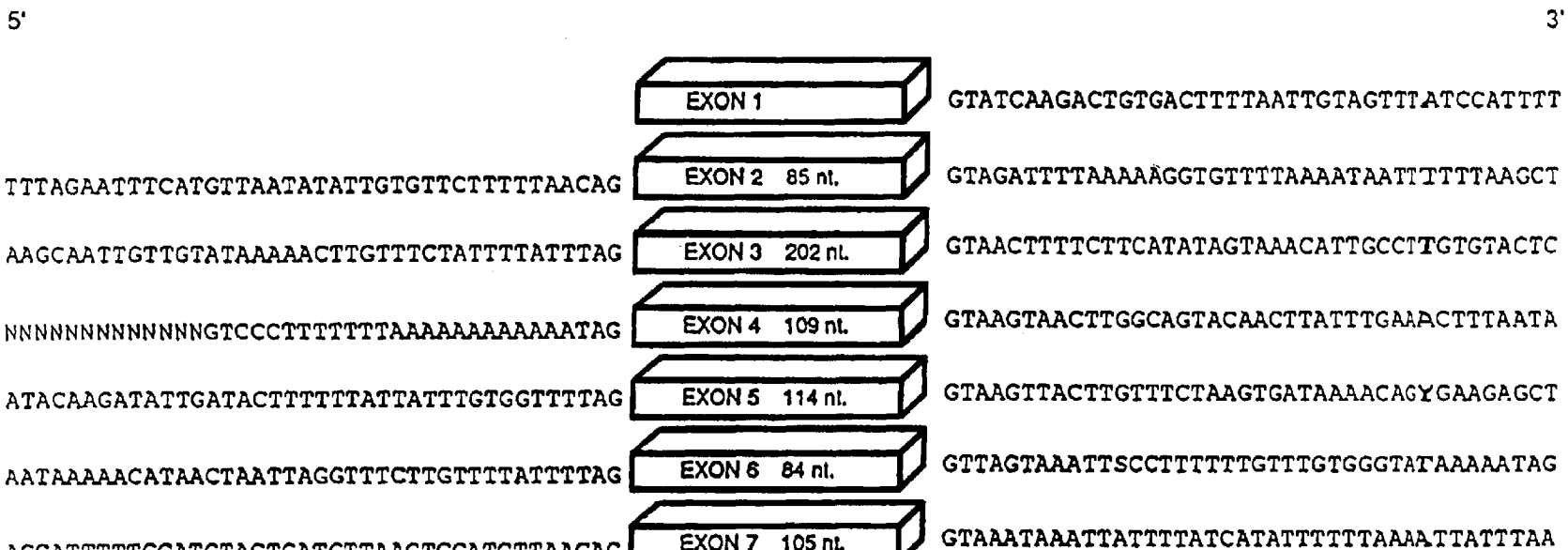
Figures 2, 7B:
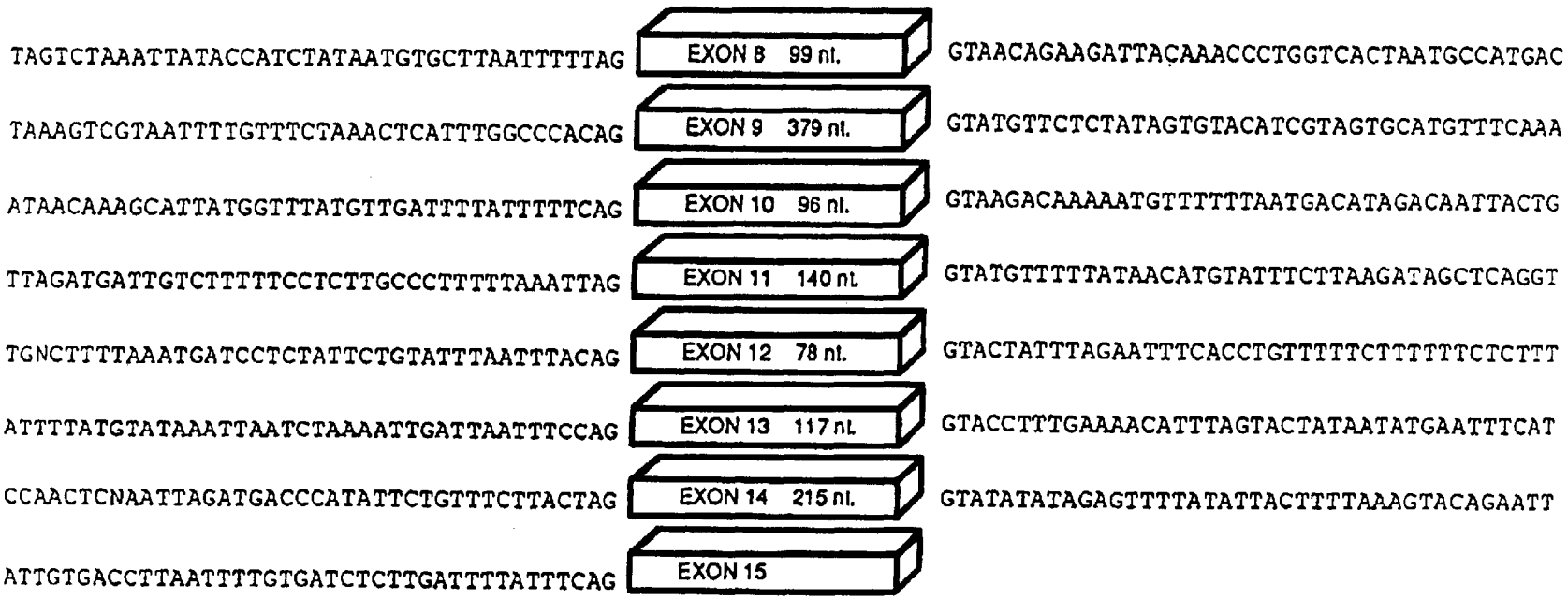

The sequences of the unique conformers from exons 7, 8, 10, and 11 of DP2.5 revealed dramatic mutations in the DP2.5 gene. The sequence of the new mutation creating the exon 7 conformer in patient 3746 was shown to contain deletion of two adjacent nucleotides, at positions 730 and 731 in the cDNA sequence ([FIG. 7,] SEQ ID NO:1). The normal sequence at this splice junction is CAGGGTCA (intronic sequence underlined), with the intron-exon boundary between the two repetitions of AG. The mutant allele in this patient has the sequence CAGGTCA. Although this change is at the 5' splice site, comparison with known consensus sequences of splice junctions would suggest that a functional splice junction is maintained. If this new splice junction were functional, the mutation would introduce a frameshift that creates a stop codon 15 nucleotides downstream. If the new splice junction were not functional, messenger processing would be significantly altered.

To confirm the 2-base deletion, the PCR product from FAP patient 3746 and a control DNA were electrophoresed on an acrylamide-urea denaturing gel, along with the products of a sequencing reaction. The sample from patient 3746 showed two bands differing in size by 2 nucleotides, with the larger band identical in mobility to the control sample; this result was independent confirmation that patient, 3746 is heterozygous for a 2 bp deletion.

The unique conformer found in exon 8 of patient 3460 was found to carry a C-T transition, at position 904 in the cDNA sequence of DP2.5 [(shown in FIG. 7)], which replaced the normal sequence of CGA with TGA. This point mutation, when read in frame, results in a stop codon replacing the normal arginine codon. This single-base change had occurred within the context of a CG dimer, a potential hot spot for mutation (Barker et al., 1984).

The conformer unique to FAP patient 3827 in exon 10 was found to contain a deletion of one nucleoside (1367, 1368, or 1369) when compared to the normal sequence found in the other bands on the SSCP gel. This deletion, occurring within a set of three T's, changed the sequence from CTTTCA to CTTCA; this 1 base frameshift creates a downstream stop within 30 bases. The PCR product amplified from this patient's DNA also was electrophoresed on an acrylamide-urea denaturing gel, along with the PCR product from a control DNA and products from a sequencing reaction. The patient's PCR product showed two bands differing by 1 bp in length, with the larger identical in mobility to the PCR product from the normal DNA; this result confirmed the presence of a 1 bp deletion in patient 3827.

Sequence analysis of the variant conformer of exon 11 from patient 3712 revealed the substitution of a T by a G at position changing the normal tyrosine codon to a stop codon.

The pair of conformers observed in exon 15 of the DP2.5 gene for FAP patient 3751 also was sequenced. These conformers were found to carry a nucleotide substitution of C to G at position 5253, the third base of a valine codon. No amino acid change resulted from this substitution, suggesting that this conformer reflects a genetically silent polymorphism.

The observation of distinct inactivating mutations in the DP2.5 gene in four unrelated patients strongly suggested that DP2.5 is the gene involved in FAP. These mutations are summarized in Table IIA.

EXAMPLE 10

This example demonstrates that the mutations identified in the DP2.5 (APC) gene segregate with the FAP phenotype.

Patient 3746, described above as carrying an APC allele with a frameshift mutation, is an affected offspring of two normal parents. Colonoscopy revealed no polyps in either parent nor among the patient's three siblings.

DNA samples from both parents, from the patient's wife, and from their three children were examined. SSCP analysis of DNA from both of the [patients's] *patient's* parents displayed the normal pattern of conformers for exon 7, as did DNA from the patient's wife and one of this off-spring. The two other children, however, displayed the same new conformers as their affected father. Testing of the patient and his parents with highly polymorphic VNTR (variable number of tandem repeat) markers showed a 99.98% likelihood that they are his biological parents.

These obserations confirmed that this novel conformer, known to reflect a 2 bp deletion mutation in the DP2.5 gene, appeared spontaneously with FAP in this pedigree and was transmitted to two of the children of the affected individual.

EXAMPLE 11

This example demonstrates polymorphisms in the APC gene which appear to be unrelated to disease (FAP).

Sequencing of variant conformers found among controls as well as individuals with APC has revealed the following polymorphisms in the APC gene; first, in exon 11, at position 1458, a substitution of T to C creating an RsaI restriction site but no amino acid change; and second, in exon 15, at positions 5037 and 5271, substitutions of A To G and G to T, respectively, neither resulting in amino acid substitutions. These nucleotide polymorphisms in the APC gene sequence may be useful for diagnostic purposes.

EXAMPLE 12

This example shows the structure of the APC gene.

The structure of the APC gene is schematically shown in FIG. 8, with flanking intron sequences indicated (SEQ ID NO:11–38).

The continuity of the very large (6.5 kb), most 3' exon in DP2.5 was shown in two ways. First, inverse PCR with primers spanning the entire length of this exon revealed no divergence of the cDNA sequence from the genomic sequence. Second, PCR amplification with converging primers placed at intervals along the exon generated products of the same size whether amplified from the originally isolated cDNA, cDNA from various tissues, or genomic template. Two forms of exon 9 were found in DP2.5; one is the complete exon; and the other, labeled exon 9A, is the result of a splice into the interior of the exon that deletes bases 934 to 1236 in the mRNA and removes 101 amino acids from the predicted protein (see [FIG. 3] *FIGS. 3A–3Z*, SEQ ID NO:1 and 2).

EXAMPLE 13

This example demonstrates the mapping of the FAP deletions with respect to the APC exons.

Somatic cell hybrids carrying the segregated chromosomes 5 from the 100 kb (HHW1291) and 260 kb (HHW1155) deletion patients were used to determine the distribution of the APC genes exons across the deletions. DNAs from these cell lines were used as template, along with genomic DNA from a normal control, for PCR-based amplification of the APC exons.

PCR analysis of the hybrids from the 260 kb deletion of patient 3214 showed that all but one (exon 1) of the APC exons are removed by this deletion. PCR analysis of the somatic cell hybrid HHW1291, carrying the chromosome 5 homolog with the 100 kb deletion from patient 3824, revealed that exons 1 through 9 are present but exons 10 through 15 are missing. This result placed the deletion breakpoint either between exons 9 and 10 or within exon 10.

EXAMPLE 14

This example demonstrates the expression of alternately spliced APC messenger in normal tissues and in cancer cell lines.

Tissues that express the APC gene were identified by PCR amplification of cDNA made to mRNA with primers located within adjacent APC exons. In addition, PCR primers that flank the alternatively spliced exon 9 were chosen so that the expression pattern of both splice forms could be asserted. All tissue types tested (brain, lung, aorta, spleen, heart, kidney, liver, stomach, placenta, and colonic mucosa) and cultured cell lines (lymphoblasts, HL60, and choriocarcinoma)

expressed both splice forms of the APC gene. We note, however, that expression by lymphocytes normally residing in some tissues, including colon, prevents unequivocal assessment of expression. The large mRNA, containing the complete exon 9 rather than only exon 9A, appears to be the more abundant message.

Northern analysis of poly(A)-selected RNA from lymphoblasts revealed a single band of approximately 10 kb, consistently with the size of the sequenced cDNA.

EXAMPLE 15

This example discusses structural features of the APC protein predicted from the sequence.

The cDNA consensus sequence of APC predicts that the longer, more abundant form of the message codes for a [2842 or 2844 ] *2843* amino acid peptide with a mass of 311.8 kd. This predicted APC peptide was compared with the current data bases of protein and DNA sequences using both Intelligenetics and GCG software packages. No genes with a high degree of amino acid sequence similarity were found. Although many short (approximately 20 amino arid) regions of sequence similarity were uncovered, none was sufficiently strong to reveal which, if any, might represent functional homology. Interestingly, multiple similarities to myosins and keratins did appear. The APC gene also was scanned for sequence motifs of known function; although multiple glycosylation, phosphorylation, and myristoylation sites were seen, their significance is uncertain.

Analysis of the APC peptide sequence did identify features important in considering potential protein structure. Hydropathy plots (Kyte and Doolittle, J. Mol. Biol. Vol. 157, pp. 105–132(1982)) indicate that the APC protein is notably hydrophilic. No hydrophobic domains suggesting a signal peptide or a membrane-spanning domain were found. Analysis of the first 1000 residues indicates that α-helical rods may form (Cohen and Parry, Trends Biochem, Sci. Vol. 77, pp. 245–248 (1986); there is a scarcity of proline residues and, there are a number of regions containing heptad repeats (apolar-X-X-apolar-X-X-X). Interestingly, in exon 9A, the deleted form of exon 9, two heptad repeat regions are reconnected in the proper heptad repeat frame, deleting the intervening peptide region. After the first 1000 residues, the high proline content of the remainder of the peptide suggests a compact rather than a rod-like structure.

The most prominent feature of the second 1000 residues is a 20 amino acid repeat that is iterated seven times with semiregular spacing (Table 4). The intervening sequences between the seven repeat regions contained 114, 116, 151, 205, 107, and 58 amino acids, respectively. Finally, residues 2200–24000 contain a 200 amino acid basic domain.

TABLE IV

Seven Different Versions of the 20-Amino Acid Repeat

| | | | | | | | | | | | | | | | | | | | | |
|---|---|---|---|---|---|---|---|---|---|---|---|---|---|---|---|---|---|---|---|---|
| Consensus: | F | * | V | E | * | T | P | * | C | F | S | R | * | S | S | L | S | S | L | S | (SEQ ID NO:147) |
| 1262: | Y | C | V | E | D | T | P | I | C | F | S | R | C | S | S | L | S | S | L | S | (SEQ ID NO:148) |
| 1376: | H | T | V | Q | E | T | P | L | M | F | S | R | C | T | S | V | S | S | L | D | (SEQ ID NO:149) |
| 1492: | F | A | T | E | S | T | P | D | G | F | S | C | S | S | S | L | S | A | L | S | (SEQ ID NO:150) |
| 1643: | Y | C | V | E | G | T | P | I | N | F | S | T | A | T | S | L | S | D | L | T | (SEQ ID NO:151) |
| 1848: | T | P | I | E | G | T | P | Y | C | F | S | R | N | D | S | L | S | S | L | D | (SEQ ID NO:152) |
| 1953: | F | A | I | E | N | T | P | V | C | P | S | H | N | S | S | L | S | S | L | S | (SEQ ID NO:153) |
| 2013: | R | H | V | E | D | T | P | V | C | F | S | R | N | S | S | L | S | S | L | S | (SEQ ID NO:154) |

Numbers denote the first amino acid of each repeat. The consensus sequence at the top reflects a majority amino acid at a given position. In the consensus sequence. "*" indicates "Xaa"

SEQUENCE LISTING (1) GENERAL INFORMATION:

(iii) NUMBER OF SEQUENCES: 154

(2) INFORMATION FOR SEQ ID NO: 1:

(i) SEQUENCE CHARACTERISTICS:
(A) LENGTH: 9606 base pairs
(B) TYPE: nucleic acid
(C) STRANDEDNESS: double
(D) TOPOLOGY: linear (ii) MOLECULE TYPE: cDNA (vi) ORIGINAL SOURCE:
(A) ORGANISM: Homo sapiens (vii) IMMEDIATE SOURCE:
(B) CLONE: DP2.5(APC)

(ix) FEATURE:
(A) NAME/KEY: CDS
(B) LOCATION: 34..8562

-continued (xi) SEQUENCE DESCRIPTION: SEQ ID NO: 1:

```
GGACTCGGAA ATGAGGTCCA AGGGTAGCCA AGG ATG GCT GCA GCT TCA TAT GAT      54
                                     Met Ala Ala Ala Ser Tyr Asp
                                       1               5

CAG TTG TTA AAG CAA GTT GAG GCA CTG AAG ATG GAG AAC TCA AAT CTT      102
Gln Leu Leu Lys Gln Val Glu Ala Leu Lys Met Glu Asn Ser Asn Leu
         10                  15                  20

CGA CAA GAG CTA GAA GAT AAT TCC AAT CAT CTT ACA AAA CTG GAA ACT      150
Arg Gln Glu Leu Glu Asp Asn Ser Asn His Leu Thr Lys Leu Glu Thr
     25                  30                  35

GAG GCA TCT AAT ATG AAG GAA GTA CTT AAA CAA CTA CAA GGA AGT ATT      198
Glu Ala Ser Asn Met Lys Glu Val Leu Lys Gln Leu Gln Gly Ser Ile
 40                  45                  50                  55

GAA GAT GAA GCT ATG GCT TCT TCT GGA CAG ATT GAT TTA TTA GAG CGT      246
Glu Asp Glu Ala Met Ala Ser Ser Gly Gln Ile Asp Leu Leu Glu Arg
                 60                  65                  70

CTT AAA GAG CTT AAC TTA GAT AGC AGT AAT TTC CCT GGA GTA AAA CTG      294
Leu Lys Glu Leu Asn Leu Asp Ser Ser Asn Phe Pro Gly Val Lys Leu
             75                  80                  85

CGG TCA AAA ATG TCC CTC CGT TCT TAT GGA AGC CGG GAA GGA TCT GTA      342
Arg Ser Lys Met Ser Leu Arg Ser Tyr Gly Ser Arg Glu Gly Ser Val
         90                  95                 100

TCA AGC CGT TCT GGA GAG TGC AGT CCT GTT CCT ATG GGT TCA TTT CCA      390
Ser Ser Arg Ser Gly Glu Cys Ser Pro Val Pro Met Gly Ser Phe Pro
    105                 110                 115

AGA AGA GGG TTT GTA AAT GGA AGC AGA GAA AGT ACT GGA TAT TTA GAA      438
Arg Arg Gly Phe Val Asn Gly Ser Arg Glu Ser Thr Gly Tyr Leu Glu
120                 125                 130                 135

GAA CTT GAG AAA GAG AGG TCA TTG CTT CTT GCT GAT CTT GAC AAA GAA      486
Glu Leu Glu Lys Glu Arg Ser Leu Leu Leu Ala Asp Leu Asp Lys Glu
                140                 145                 150

GAA AAG GAA AAA GAC TGG TAT TAC GCT CAA CTT CAG AAT CTC ACT AAA      534
Glu Lys Glu Lys Asp Trp Tyr Tyr Ala Gln Leu Gln Asn Leu Thr Lys
            155                 160                 165

AGA ATA GAT AGT CTT CCT TTA ACT GAA AAT TTT TCC TTA CAA ACA GAT      582
Arg Ile Asp Ser Leu Pro Leu Thr Glu Asn Phe Ser Leu Gln Thr Asp
        170                 175                 180

TTG ACC AGA AGG CAA TTG GAA TAT GAA GCA AGG CAA ATC AGA GTT GCG      630
Leu Thr Arg Arg Gln Leu Glu Tyr Glu Ala Arg Gln Ile Arg Val Ala
    185                 190                 195

ATG GAA GAA CAA CTA GGT ACC TGC CAG GAT ATG GAA AAA CGA GCA CAG      678
Met Glu Glu Gln Leu Gly Thr Cys Gln Asp Met Glu Lys Arg Ala Gln
200                 205                 210                 215

CGA AGA ATA GCC AGA ATT CAG CAA ATC GAA AAG GAC ATA CTT CGT ATA      726
Arg Arg Ile Ala Arg Ile Gln Gln Ile Glu Lys Asp Ile Leu Arg Ile
                220                 225                 230

CGA CAG CTT TTA CAG TCC CAA GCA ACA GAA GCA GAG AGG TCA TCT CAG      774
Arg Gln Leu Leu Gln Ser Gln Ala Thr Glu Ala Glu Arg Ser Ser Gln
            235                 240                 245

AAC AAG CAT GAA ACC GGC TCA CAT GAT GCT GAG CGG CAG AAT GAA GGT      822
Asn Lys His Glu Thr Gly Ser His Asp Ala Glu Arg Gln Asn Glu Gly
        250                 255                 260

CAA GGA GTG GGA GAA ATC AAC ATG GCA ACT TCT GGT AAT GGT CAG GGT      870
Gln Gly Val Gly Glu Ile Asn Met Ala Thr Ser Gly Asn Gly Gln Gly
    265                 270                 275

TCA ACT ACA CGA ATG GAC CAT GAA ACA GCC AGT GTT TTG AGT TCT AGT      918
Ser Thr Thr Arg Met Asp His Glu Thr Ala Ser Val Leu Ser Ser Ser
280                 285                 290                 295

AGC ACA CAC TCT GCA CCT CGA AGG CTG ACA AGT CAT CTG GGA ACC AAG      966
```

-continued

```
Ser Thr His Ser Ala Pro Arg Arg Leu Thr Ser His Leu Gly Thr Lys
                300                 305                 310

GTG GAA ATG GTG TAT TCA TTG TTG TCA ATG CTT GGT ACT CAT GAT AAG1     014
Val Glu Met Val Tyr Ser Leu Leu Ser Met Leu Gly Thr His Asp Lys
            315                 320                 325

GAT GAT ATG TCG CGA ACT TTG CTA GCT ATG TCT AGC TCC CAA GAC AGC     1062
Asp Asp Met Ser Arg Thr Leu Leu Ala Met Ser Ser Ser Gln Asp Ser
        330                 335                 340

TGT ATA TCC ATG CGA CAG TCT GGA TGT CTT CCT CTC CTC ATC CAG CTT     1110
Cys Ile Ser Met Arg Gln Ser Gly Cys Leu Pro Leu Leu Ile Gln Leu
    345                 350                 355

TTA CAT GGC AAT GAC AAA GAC TCT GTA TTG TTG GGA AAT TCC CGG GGC     1158
Leu His Gly Asn Asp Lys Asp Ser Val Leu Leu Gly Asn Ser Arg Gly
360                 365                 370                 375

AGT AAA GAG GCT CGG GCC AGG GCC AGT GCA GCA CTC CAC AAC ATC ATT     1206
Ser Lys Glu Ala Arg Ala Arg Ala Ser Ala Ala Leu His Asn Ile Ile
                380                 385                 390

CAC TCA CAG CCT GAT GAC AAG AGA GGC AGG CGT GAA ATC CGA GTC CTT     1254
His Ser Gln Pro Asp Asp Lys Arg Gly Arg Arg Glu Ile Arg Val Leu
            395                 400                 405

CAT CTT TTG GAA CAG ATA CGC GCT TAC TGT GAA ACC TGT TGG GAG TGG     1302
His Leu Leu Glu Gln Ile Arg Ala Tyr Cys Glu Thr Cys Trp Glu Trp
        410                 415                 420

CAG GAA GCT CAT GAA CCA GGC ATG GAC CAG GAC AAA AAT CCA ATG CCA     1350
Gln Glu Ala His Glu Pro Gly Met Asp Gln Asp Lys Asn Pro Met Pro
    425                 430                 435

GCT CCT GTT GAA CAT CAG ATC TGT CCT GCT GTG TGT GTT CTA ATG AAA     1398
Ala Pro Val Glu His Gln Ile Cys Pro Ala Val Cys Val Leu Met Lys
440                 445                 450                 455

CTT TCA TTT GAT GAA GAG CAT AGA CAT GCA ATG AAT GAA CTA GGG GGA     1446
Leu Ser Phe Asp Glu Glu His Arg His Ala Met Asn Glu Leu Gly Gly
                460                 465                 470

CTA CAG GCC ATT GCA GAA TTA TTG CAA GTG GAC TGT GAA ATG TAT GGG     1494
Leu Gln Ala Ile Ala Glu Leu Leu Gln Val Asp Cys Glu Met Tyr Gly
            475                 480                 485

CTT ACT AAT GAC CAC TAC AGT ATT ACA CTA AGA CGA TAT GCT GGA ATG     1542
Leu Thr Asn Asp His Tyr Ser Ile Thr Leu Arg Arg Tyr Ala Gly Met
        490                 495                 500

GCT TTG ACA AAC TTG ACT TTT GGA GAT GTA GCC AAC AAG GCT ACG CTA     1590
Ala Leu Thr Asn Leu Thr Phe Gly Asp Val Ala Asn Lys Ala Thr Leu
    505                 510                 515

TGC TCT ATG AAA GGC TGC ATG AGA GCA CTT GTG GCC CAA CTA AAA TCT     1638
Cys Ser Met Lys Gly Cys Met Arg Ala Leu Val Ala Gln Leu Lys Ser
520                 525                 530                 535

GAA AGT GAA GAC TTA CAG CAG GTT ATT GCA AGT GTT TTG AGG AAT TTG     1686
Glu Ser Glu Asp Leu Gln Gln Val Ile Ala Ser Val Leu Arg Asn Leu
                540                 545                 550

TCT TGG CGA GCA GAT GTA AAT AGT AAA AAG ACG TTG CGA GAA GTT GGA     1734
Ser Trp Arg Ala Asp Val Asn Ser Lys Lys Thr Leu Arg Glu Val Gly
            555                 560                 565

AGT GTG AAA GCA TTG ATG GAA TGT GCT TTA GAA GTT AAA AAG GAA TCA     1782
Ser Val Lys Ala Leu Met Glu Cys Ala Leu Glu Val Lys Lys Glu Ser
        570                 575                 580

ACC CTC AAA AGC GTA TTG AGT GCC TTA TGG AAT TTG TCA GCA CAT TGC     1830
Thr Leu Lys Ser Val Leu Ser Ala Leu Trp Asn Leu Ser Ala His Cys
    585                 590                 595

ACT GAG AAT AAA GCT GAT ATA TGT GCT GTA GAT GGT GCA CTT GCA TTT     1878
Thr Glu Asn Lys Ala Asp Ile Cys Ala Val Asp Gly Ala Leu Ala Phe
600                 605                 610                 615
```

-continued

```
TTG GTT GGC ACT CTT ACT TAC CGG AGC CAG ACA AAC ACT TTA GCC ATT     1926
Leu Val Gly Thr Leu Thr Tyr Arg Ser Gln Thr Asn Thr Leu Ala Ile
                620                 625                 630

ATT GAA AGT GGA GGT GGG ATA TTA CGG AAT GTG TCC AGC TTG ATA GCT     1974
Ile Glu Ser Gly Gly Gly Ile Leu Arg Asn Val Ser Ser Leu Ile Ala
            635                 640                 645

ACA AAT GAG GAC CAC AGG CAA ATC CTA AGA GAG AAC AAC TGT CTA CAA     2022
Thr Asn Glu Asp His Arg Gln Ile Leu Arg Glu Asn Asn Cys Leu Gln
        650                 655                 660

ACT TTA TTA CAA CAC TTA AAA TCT CAT AGT TTG ACA ATA GTC AGT AAT     2070
Thr Leu Leu Gln His Leu Lys Ser His Ser Leu Thr Ile Val Ser Asn
    665                 670                 675

GCA TGT GGA ACT TTG TGG AAT CTC TCA GCA AGA AAT CCT AAA GAC CAG     2118
Ala Cys Gly Thr Leu Trp Asn Leu Ser Ala Arg Asn Pro Lys Asp Gln
680                 685                 690                 695

GAA GCA TTA TGG GAC ATG GGG GCA GTT AGC ATG CTC AAG AAC CTC ATT     2166
Glu Ala Leu Trp Asp Met Gly Ala Val Ser Met Leu Lys Asn Leu Ile
                700                 705                 710

CAT TCA AAG CAC AAA ATG ATT GCT ATG GGA AGT GCT GCA GCT TTA AGG     2214
His Ser Lys His Lys Met Ile Ala Met Gly Ser Ala Ala Ala Leu Arg
            715                 720                 725

AAT CTC ATG GCA AAT AGG CCT GCG AAG TAC AAG GAT GCC AAT ATT ATG     2262
Asn Leu Met Ala Asn Arg Pro Ala Lys Tyr Lys Asp Ala Asn Ile Met
        730                 735                 740

TCT CCT GGC TCA AGC TTG CCA TCT CTT CAT GTT AGG AAA CAA AAA GCC     2310
Ser Pro Gly Ser Ser Leu Pro Ser Leu His Val Arg Lys Gln Lys Ala
    745                 750                 755

CTA GAA GCA GAA TTA GAT GCT CAG CAC TTA TCA GAA ACT TTT GAC AAT     2358
Leu Glu Ala Glu Leu Asp Ala Gln His Leu Ser Glu Thr Phe Asp Asn
760                 765                 770                 775

ATA GAC AAT TTA AGT CCC AAG GCA TCT CAT CGT AGT AAG CAG AGA CAC     2406
Ile Asp Asn Leu Ser Pro Lys Ala Ser His Arg Ser Lys Gln Arg His
                780                 785                 790

AAG CAA AGT CTC TAT GGT GAT TAT GTT TTT GAC ACC AAT CGA CAT GAT     2454
Lys Gln Ser Leu Tyr Gly Asp Tyr Val Phe Asp Thr Asn Arg His Asp
            795                 800                 805

GAT AAT AGG TCA GAC AAT TTT AAT ACT GGC AAC ATG ACT GTC CTT TCA     2502
Asp Asn Arg Ser Asp Asn Phe Asn Thr Gly Asn Met Thr Val Leu Ser
        810                 815                 820

CCA TAT TTG AAT ACT ACA GTG TTA CCC AGC TCC TCT TCA TCA AGA GGA     2550
Pro Tyr Leu Asn Thr Thr Val Leu Pro Ser Ser Ser Ser Ser Arg Gly
    825                 830                 835

AGC TTA GAT AGT TCT CGT TCT GAA AAA GAT AGA AGT TTG GAG AGA GAA     2598
Ser Leu Asp Ser Ser Arg Ser Glu Lys Asp Arg Ser Leu Glu Arg Glu
840                 845                 850                 855

CGC GGA ATT GGT CTA GGC AAC TAC CAT CCA GCA ACA GAA AAT CCA GGA     2646
Arg Gly Ile Gly Leu Gly Asn Tyr His Pro Ala Thr Glu Asn Pro Gly
                860                 865                 870

ACT TCT TCA AAG CGA GGT TTG CAG ATC TCC ACC ACT GCA GCC CAG ATT     2694
Thr Ser Ser Lys Arg Gly Leu Gln Ile Ser Thr Thr Ala Ala Gln Ile
            875                 880                 885

GCC AAA GTC ATG GAA GAA GTG TCA GCC ATT CAT ACC TCT CAG GAA GAC     2742
Ala Lys Val Met Glu Glu Val Ser Ala Ile His Thr Ser Gln Glu Asp
        890                 895                 900

AGA AGT TCT GGG TCT ACC ACT GAA TTA CAT TGT GTG ACA GAT GAG AGA     2790
Arg Ser Ser Gly Ser Thr Thr Glu Leu His Cys Val Thr Asp Glu Arg
    905                 910                 915

AAT GCA CTT AGA AGA AGC TCT GCT GCC CAT ACA CAT TCA AAC ACT TAC     2838
Asn Ala Leu Arg Arg Ser Ser Ala Ala His Thr His Ser Asn Thr Tyr
920                 925                 930                 935
```

-continued

```
AAT TTC ACT AAG TCG GAA AAT TCA AAT AGG ACA TGT TCT ATG CCT TAT     2886
Asn Phe Thr Lys Ser Glu Asn Ser Asn Arg Thr Cys Ser Met Pro Tyr
                940                 945                 950

GCC AAA TTA GAA TAC AAG AGA TCT TCA AAT GAT AGT TTA AAT AGT GTC     2934
Ala Lys Leu Glu Tyr Lys Arg Ser Ser Asn Asp Ser Leu Asn Ser Val
            955                 960                 965

AGT AGT AAT GAT GGT TAT GGT AAA AGA GGT CAA ATG AAA CCC TCG ATT     2982
Ser Ser Asn Asp Gly Tyr Gly Lys Arg Gly Gln Met Lys Pro Ser Ile
        970                 975                 980

GAA TCC TAT TCT GAA GAT GAT GAA AGT AAG TTT TGC AGT TAT GGT CAA     3030
Glu Ser Tyr Ser Glu Asp Asp Glu Ser Lys Phe Cys Ser Tyr Gly Gln
    985                 990                 995

TAC CCA GCC GAC CTA GCC CAT AAA ATA CAT AGT GCA AAT CAT ATG GAT     3078
Tyr Pro Ala Asp Leu Ala His Lys Ile His Ser Ala Asn His Met Asp
1000                1005                1010                1015

GAT AAT GAT GGA GAA CTA GAT ACA CCA ATA AAT TAT AGT CTT AAA TAT     3126
Asp Asn Asp Gly Glu Leu Asp Thr Pro Ile Asn Tyr Ser Leu Lys Tyr
                1020                1025                1030

TCA GAT GAG CAG TTG AAC TCT GGA AGG CAA AGT CCT TCA CAG AAT GAA     3174
Ser Asp Glu Gln Leu Asn Ser Gly Arg Gln Ser Pro Ser Gln Asn Glu
            1035                1040                1045

AGA TGG GCA AGA CCC AAA CAC ATA ATA GAA GAT GAA ATA AAA CAA AGT     3222
Arg Trp Ala Arg Pro Lys His Ile Ile Glu Asp Glu Ile Lys Gln Ser
        1050                1055                1060

GAG CAA AGA CAA TCA AGG AAT CAA AGT ACA ACT TAT CCT GTT TAT ACT     3270
Glu Gln Arg Gln Ser Arg Asn Gln Ser Thr Thr Tyr Pro Val Tyr Thr
    1065                1070                1075

GAG AGC ACT GAT GAT AAA CAC CTC AAG TTC CAA CCA CAT TTT GGA CAG     3318
Glu Ser Thr Asp Asp Lys His Leu Lys Phe Gln Pro His Phe Gly Gln
1080                1085                1090                1095

CAG GAA TGT GTT TCT CCA TAC AGG TCA CGG GGA GCC AAT GGT TCA GAA     3366
Gln Glu Cys Val Ser Pro Tyr Arg Ser Arg Gly Ala Asn Gly Ser Glu
                1100                1105                1110

ACA AAT CGA GTG GGT TCT AAT CAT GGA ATT AAT CAA AAT GTA AGC CAG     3414
Thr Asn Arg Val Gly Ser Asn His Gly Ile Asn Gln Asn Val Ser Gln
            1115                1120                1125

TCT TTG TGT CAA GAA GAT GAC TAT GAA GAT GAT AAG CCT ACC AAT TAT     3462
Ser Leu Cys Gln Glu Asp Asp Tyr Glu Asp Asp Lys Pro Thr Asn Tyr
        1130                1135                1140

AGT GAA CGT TAC TCT GAA GAA GAA CAG CAT GAA GAA GAA GAG AGA CCA     3510
Ser Glu Arg Tyr Ser Glu Glu Glu Gln His Glu Glu Glu Glu Arg Pro
    1145                1150                1155

ACA AAT TAT AGC ATA AAA TAT AAT GAA GAG AAA CGT CAT GTG GAT CAG     3558
Thr Asn Tyr Ser Ile Lys Tyr Asn Glu Glu Lys Arg His Val Asp Gln
1160                1165                1170                1175

CCT ATT GAT TAT AGT TTA AAA TAT GCC ACA GAT ATT CCT TCA TCA CAG     3606
Pro Ile Asp Tyr Ser Leu Lys Tyr Ala Thr Asp Ile Pro Ser Ser Gln
                1180                1185                1190

AAA CAG TCA TTT TCA TTC TCA AAG AGT TCA TCT GGA CAA AGC AGT AAA     3654
Lys Gln Ser Phe Ser Phe Ser Lys Ser Ser Ser Gly Gln Ser Ser Lys
            1195                1200                1205

ACC GAA CAT ATG TCT TCA AGC AGT GAG AAT ACG TCC ACA CCT TCA TCT     3702
Thr Glu His Met Ser Ser Ser Ser Glu Asn Thr Ser Thr Pro Ser Ser
        1210                1215                1220

AAT GCC AAG AGG CAG AAT CAG CTC CAT CCA AGT TCT GCA CAG AGT AGA     3750
Asn Ala Lys Arg Gln Asn Gln Leu His Pro Ser Ser Ala Gln Ser Arg
    1225                1230                1235

AGT GGT CAG CCT CAA AAG GCT GCC ACT TGC AAA GTT TCT TCT ATT AAC     3798
Ser Gly Gln Pro Gln Lys Ala Ala Thr Cys Lys Val Ser Ser Ile Asn
```

-continued

```
1240                1245                1250                1255

CAA GAA ACA ATA CAG ACT TAT TGT GTA GAA GAT ACT CCA ATA TGT TTT     3846
Gln Glu Thr Ile Gln Thr Tyr Cys Val Glu Asp Thr Pro Ile Cys Phe
                1260                1265                1270

TCA AGA TGT AGT TCA TTA TCA TCT TTG TCA TCA GCT GAA GAT GAA ATA     3894
Ser Arg Cys Ser Ser Leu Ser Ser Leu Ser Ser Ala Glu Asp Glu Ile
            1275                1280                1285

GGA TGT AAT CAG ACG ACA CAG GAA GCA GAT TCT GCT AAT ACC CTG CAA     3942
Gly Cys Asn Gln Thr Thr Gln Glu Ala Asp Ser Ala Asn Thr Leu Gln
        1290                1295                1300

ATA GCA GAA ATA AAA GGA AAG ATT GGA ACT AGG TCA GCT GAA GAT CCT     3990
Ile Ala Glu Ile Lys Gly Lys Ile Gly Thr Arg Ser Ala Glu Asp Pro
    1305                1310                1315

GTG AGC GAA GTT CCA GCA GTG TCA CAG CAC CCT AGA ACC AAA TCC AGC     4038
Val Ser Glu Val Pro Ala Val Ser Gln His Pro Arg Thr Lys Ser Ser
1320                1325                1330                1335

AGA CTG CAG GGT TCT AGT TTA TCT TCA GAA TCA GCC AGG CAC AAA GCT     4086
Arg Leu Gln Gly Ser Ser Leu Ser Ser Glu Ser Ala Arg His Lys Ala
                1340                1345                1350

GTT GAA TTT CCT TCA GGA GCG AAA TCT CCC TCC AAA AGT GGT GCT CAG     4134
Val Glu Phe Pro Ser Gly Ala Lys Ser Pro Ser Lys Ser Gly Ala Gln
            1355                1360                1365

ACA CCC AAA AGT CCA CCT GAA CAC TAT GTT CAG GAG ACC CCA CTC ATG     4182
Thr Pro Lys Ser Pro Pro Glu His Tyr Val Gln Glu Thr Pro Leu Met
        1370                1375                1380

TTT AGC AGA TGT ACT TCT GTC AGT TCA CTT GAT AGT TTT GAG AGT CGT     4230
Phe Ser Arg Cys Thr Ser Val Ser Ser Leu Asp Ser Phe Glu Ser Arg
    1385                1390                1395

TCG ATT GCC AGC TCC GTT CAG AGT GAA CCA TGC AGT GGA ATG GTA AGT     4278
Ser Ile Ala Ser Ser Val Gln Ser Glu Pro Cys Ser Gly Met Val Ser
1400                1405                1410                1415

GGC ATT ATA AGC CCC AGT GAT CTT CCA GAT AGC CCT GGA CAA ACC ATG     4326
Gly Ile Ile Ser Pro Ser Asp Leu Pro Asp Ser Pro Gly Gln Thr Met
                1420                1425                1430

CCA CCA AGC AGA AGT AAA ACA CCT CCA CCA CCT CCT CAA ACA GCT CAA     4374
Pro Pro Ser Arg Ser Lys Thr Pro Pro Pro Pro Pro Gln Thr Ala Gln
            1435                1440                1445

ACC AAG CGA GAA GTA CCT AAA AAT AAA GCA CCT ACT GCT GAA AAG AGA     4422
Thr Lys Arg Glu Val Pro Lys Asn Lys Ala Pro Thr Ala Glu Lys Arg
        1450                1455                1460

GAG AGT GGA CCT AAG CAA GCT GCA GTA AAT GCT GCA GTT CAG AGG GTC     4470
Glu Ser Gly Pro Lys Gln Ala Ala Val Asn Ala Ala Val Gln Arg Val
    1465                1470                1475

CAG GTT CTT CCA GAT GCT GAT ACT TTA TTA CAT TTT GCC ACA GAA AGT     4518
Gln Val Leu Pro Asp Ala Asp Thr Leu Leu His Phe Ala Thr Glu Ser
1480                1485                1490                1495

ACT CCA GAT GGA TTT TCT TGT TCA TCC AGC CTG AGT GCT CTG AGC CTC     4566
Thr Pro Asp Gly Phe Ser Cys Ser Ser Ser Leu Ser Ala Leu Ser Leu
                1500                1505                1510

GAT GAG CCA TTT ATA CAG AAA GAT GTG GAA TTA AGA ATA ATG CCT CCA     4614
Asp Glu Pro Phe Ile Gln Lys Asp Val Glu Leu Arg Ile Met Pro Pro
            1515                1520                1525

GTT CAG GAA AAT GAC AAT GGG AAT GAA ACA GAA TCA GAG CAG CCT AAA     4662
Val Gln Glu Asn Asp Asn Gly Asn Glu Thr Glu Ser Glu Gln Pro Lys
        1530                1535                1540

GAA TCA AAT GAA AAC CAA GAG AAA GAG GCA GAA AAA ACT ATT GAT TCT     4710
Glu Ser Asn Glu Asn Gln Glu Lys Glu Ala Glu Lys Thr Ile Asp Ser
    1545                1550                1555

GAA AAG GAC CTA TTA GAT GAT TCA GAT GAT GAT GAT ATT GAA ATA CTA     4758
```

-continued

```
Glu Lys Asp Leu Leu Asp Asp Ser Asp Asp Asp Asp Ile Glu Ile Leu
1560                1565                1570                1575

GAA GAA TGT ATT ATT TCT GCC ATG CCA ACA AAG TCA TCA CGT AAA GGC     4806
Glu Glu Cys Ile Ile Ser Ala Met Pro Thr Lys Ser Ser Arg Lys Gly
                1580                1585                1590

AAA AAG CCA GCC CAG ACT GCT TCA AAA TTA CCT CCA CCT GTG GCA AGG     4854
Lys Lys Pro Ala Gln Thr Ala Ser Lys Leu Pro Pro Pro Val Ala Arg
            1595                1600                1605

AAA CCA AGT CAG CTG CCT GTG TAC AAA CTT CTA CCA TCA CAA AAC AGG     4902
Lys Pro Ser Gln Leu Pro Val Tyr Lys Leu Leu Pro Ser Gln Asn Arg
        1610                1615                1620

TTG CAA CCC CAA AAG CAT GTT AGT TTT ACA CCG GGG GAT GAT ATG CCA     4950
Leu Gln Pro Gln Lys His Val Ser Phe Thr Pro Gly Asp Asp Met Pro
    1625                1630                1635

CGG GTG TAT TGT GTT GAA GGG ACA CCT ATA AAC TTT TCC ACA GCT ACA     4998
Arg Val Tyr Cys Val Glu Gly Thr Pro Ile Asn Phe Ser Thr Ala Thr
1640                1645                1650                1655

TCT CTA AGT GAT CTA ACA ATC GAA TCC CCT CCA AAT GAG TTA GCT GCT     5046
Ser Leu Ser Asp Leu Thr Ile Glu Ser Pro Pro Asn Glu Leu Ala Ala
                1660                1665                1670

GGA GAA GGA GTT AGA GGA GGA GCA CAG TCA GGT GAA TTT GAA AAA CGA     5094
Gly Glu Gly Val Arg Gly Gly Ala Gln Ser Gly Glu Phe Glu Lys Arg
            1675                1680                1685

GAT ACC ATT CCT ACA GAA GGC AGA AGT ACA GAT GAG GCT CAA GGA GGA     5142
Asp Thr Ile Pro Thr Glu Gly Arg Ser Thr Asp Glu Ala Gln Gly Gly
        1690                1695                1700

AAA ACC TCA TCT GTA ACC ATA CCT GAA TTG GAT GAC AAT AAA GCA GAG     5190
Lys Thr Ser Ser Val Thr Ile Pro Glu Leu Asp Asp Asn Lys Ala Glu
    1705                1710                1715

GAA GGT GAT ATT CTT GCA GAA TGC ATT AAT TCT GCT ATG CCC AAA GGG     5238
Glu Gly Asp Ile Leu Ala Glu Cys Ile Asn Ser Ala Met Pro Lys Gly
1720                1725                1730                1735

AAA AGT CAC AAG CCT TTC CGT GTG AAA AAG ATA ATG GAC CAG GTC CAG     5286
Lys Ser His Lys Pro Phe Arg Val Lys Lys Ile Met Asp Gln Val Gln
                1740                1745                1750

CAA GCA TCT GCG TCG TCT TCT GCA CCC AAC AAA AAT CAG TTA GAT GGT     5334
Gln Ala Ser Ala Ser Ser Ser Ala Pro Asn Lys Asn Gln Leu Asp Gly
            1755                1760                1765

AAG AAA AAG AAA CCA ACT TCA CCA GTA AAA CCT ATA CCA CAA AAT ACT     5382
Lys Lys Lys Lys Pro Thr Ser Pro Val Lys Pro Ile Pro Gln Asn Thr
        1770                1775                1780

GAA TAT AGG ACA CGT GTA AGA AAA AAT GCA GAC TCA AAA AAT AAT TTA     5430
Glu Tyr Arg Thr Arg Val Arg Lys Asn Ala Asp Ser Lys Asn Asn Leu
    1785                1790                1795

AAT GCT GAG AGA GTT TTC TCA GAC AAC AAA GAT TCA AAG AAA CAG AAT     5478
Asn Ala Glu Arg Val Phe Ser Asp Asn Lys Asp Ser Lys Lys Gln Asn
1800                1805                1810                1815

TTG AAA AAT AAT TCC AAG GAC TTC AAT GAT AAG CTC CCA AAT AAT GAA     5526
Leu Lys Asn Asn Ser Lys Asp Phe Asn Asp Lys Leu Pro Asn Asn Glu
                1820                1825                1830

GAT AGA GTC AGA GGA AGT TTT GCT TTT GAT TCA CCT CAT CAT TAC ACG     5574
Asp Arg Val Arg Gly Ser Phe Ala Phe Asp Ser Pro His His Tyr Thr
            1835                1840                1845

CCT ATT GAA GGA ACT CCT TAC TGT TTT TCA CGA AAT GAT TCT TTG AGT     5622
Pro Ile Glu Gly Thr Pro Tyr Cys Phe Ser Arg Asn Asp Ser Leu Ser
        1850                1855                1860

TCT CTA GAT TTT GAT GAT GAT GAT GTT GAC CTT TCC AGG GAA AAG GCT     5670
Ser Leu Asp Phe Asp Asp Asp Asp Val Asp Leu Ser Arg Glu Lys Ala
    1865                1870                1875
```

-continued

```
GAA TTA AGA AAG GCA AAA GAA AAT AAG GAA TCA GAG GCT AAA GTT ACC     5718
Glu Leu Arg Lys Ala Lys Glu Asn Lys Glu Ser Glu Ala Lys Val Thr
1880                1885                1890                1895

AGC CAC ACA GAA CTA ACC TCC AAC CAA CAA TCA GCT AAT AAG ACA CAA     5766
Ser His Thr Glu Leu Thr Ser Asn Gln Gln Ser Ala Asn Lys Thr Gln
                1900                1905                1910

GCT ATT GCA AAG CAG CCA ATA AAT CGA GGT CAG CCT AAA CCC ATA CTT     5814
Ala Ile Ala Lys Gln Pro Ile Asn Arg Gly Gln Pro Lys Pro Ile Leu
            1915                1920                1925

CAG AAA CAA TCC ACT TTT CCC CAG TCA TCC AAA GAC ATA CCA GAC AGA     5862
Gln Lys Gln Ser Thr Phe Pro Gln Ser Ser Lys Asp Ile Pro Asp Arg
        1930                1935                1940

GGG GCA GCA ACT GAT GAA AAG TTA CAG AAT TTT GCT ATT GAA AAT ACT     5910
Gly Ala Ala Thr Asp Glu Lys Leu Gln Asn Phe Ala Ile Glu Asn Thr
    1945                1950                1955

CCA GTT TGC TTT TCT CAT AAT TCC TCT CTG AGT TCT CTC AGT GAC ATT     5958
Pro Val Cys Phe Ser His Asn Ser Ser Leu Ser Ser Leu Ser Asp Ile
1960                1965                1970                1975

GAC CAA GAA AAC AAC AAT AAA GAA AAT GAA CCT ATC AAA GAG ACT GAG     6006
Asp Gln Glu Asn Asn Asn Lys Glu Asn Glu Pro Ile Lys Glu Thr Glu
                1980                1985                1990

CCC CCT GAC TCA CAG GGA GAA CCA AGT AAA CCT CAA GCA TCA GGC TAT     6054
Pro Pro Asp Ser Gln Gly Glu Pro Ser Lys Pro Gln Ala Ser Gly Tyr
            1995                2000                2005

GCT CCT AAA TCA TTT CAT GTT GAA GAT ACC CCA GTT TGT TTC TCA AGA     6102
Ala Pro Lys Ser Phe His Val Glu Asp Thr Pro Val Cys Phe Ser Arg
        2010                2015                2020

AAC AGT TCT CTC AGT TCT CTT AGT ATT GAC TCT GAA GAT GAC CTG TTG     6150
Asn Ser Ser Leu Ser Ser Leu Ser Ile Asp Ser Glu Asp Asp Leu Leu
    2025                2030                2035

CAG GAA TGT ATA AGC TCC GCA ATG CCA AAA AAG AAA AAG CCT TCA AGA     6198
Gln Glu Cys Ile Ser Ser Ala Met Pro Lys Lys Lys Lys Pro Ser Arg
2040                2045                2050                2055

CTC AAG GGT GAT AAT GAA AAA CAT AGT CCC AGA AAT ATG GGT GGC ATA     6246
Leu Lys Gly Asp Asn Glu Lys His Ser Pro Arg Asn Met Gly Gly Ile
                2060                2065                2070

TTA GGT GAA GAT CTG ACA CTT GAT TTG AAA GAT ATA CAG AGA CCA GAT     6294
Leu Gly Glu Asp Leu Thr Leu Asp Leu Lys Asp Ile Gln Arg Pro Asp
            2075                2080                2085

TCA GAA CAT GGT CTA TCC CCT GAT TCA GAA AAT TTT GAT TGG AAA GCT     6342
Ser Glu His Gly Leu Ser Pro Asp Ser Glu Asn Phe Asp Trp Lys Ala
        2090                2095                2100

ATT CAG GAA GGT GCA AAT TCC ATA GTA AGT AGT TTA CAT CAA GCT GCT     6390
Ile Gln Glu Gly Ala Asn Ser Ile Val Ser Ser Leu His Gln Ala Ala
    2105                2110                2115

GCT GCT GCA TGT TTA TCT AGA CAA GCT TCG TCT GAT TCA GAT TCC ATC     6438
Ala Ala Ala Cys Leu Ser Arg Gln Ala Ser Ser Asp Ser Asp Ser Ile
2120                2125                2130                2135

CTT TCC CTG AAA TCA GGA ATC TCT CTG GGA TCA CCA TTT CAT CTT ACA     6486
Leu Ser Leu Lys Ser Gly Ile Ser Leu Gly Ser Pro Phe His Leu Thr
                2140                2145                2150

CCT GAT CAA GAA GAA AAA CCC TTT ACA AGT AAT AAA GGC CCA CGA ATT     6534
Pro Asp Gln Glu Glu Lys Pro Phe Thr Ser Asn Lys Gly Pro Arg Ile
            2155                2160                2165

CTA AAA CCA GGG GAG AAA AGT ACA TTG GAA ACT AAA AAG ATA GAA TCT     6582
Leu Lys Pro Gly Glu Lys Ser Thr Leu Glu Thr Lys Lys Ile Glu Ser
        2170                2175                2180

GAA AGT AAA GGA ATC AAA GGA GGA AAA AAA GTT TAT AAA AGT TTG ATT     6630
Glu Ser Lys Gly Ile Lys Gly Gly Lys Lys Val Tyr Lys Ser Leu Ile
    2185                2190                2195
```

-continued

```
ACT GGA AAA GTT CGA TCT AAT TCA GAA ATT TCA GGC CAA ATG AAA CAG     6678
Thr Gly Lys Val Arg Ser Asn Ser Glu Ile Ser Gly Gln Met Lys Gln
2200                2205                2210                2215

CCC CTT CAA GCA AAC ATG CCT TCA ATC TCT CGA GGC AGG ACA ATG ATT     6726
Pro Leu Gln Ala Asn Met Pro Ser Ile Ser Arg Gly Arg Thr Met Ile
                2220                2225                2230

CAT ATT CCA GGA GTT CGA AAT AGC TCC TCA AGT ACA AGT CCT GTT TCT     6774
His Ile Pro Gly Val Arg Asn Ser Ser Ser Ser Thr Ser Pro Val Ser
            2235                2240                2245

AAA AAA GGC CCA CCC CTT AAG ACT CCA GCC TCC AAA AGC CCT AGT GAA     6822
Lys Lys Gly Pro Pro Leu Lys Thr Pro Ala Ser Lys Ser Pro Ser Glu
        2250                2255                2260

GGT CAA ACA GCC ACC ACT TCT CCT AGA GGA GCC AAG CCA TCT GTG AAA     6870
Gly Gln Thr Ala Thr Thr Ser Pro Arg Gly Ala Lys Pro Ser Val Lys
    2265                2270                2275

TCA GAA TTA AGC CCT GTT GCC AGG CAG ACA TCC CAA ATA GGT GGG TCA     6918
Ser Glu Leu Ser Pro Val Ala Arg Gln Thr Ser Gln Ile Gly Gly Ser
2280                2285                2290                2295

AGT AAA GCA CCT TCT AGA TCA GGA TCT AGA GAT TCG ACC CCT TCA AGA     6966
Ser Lys Ala Pro Ser Arg Ser Gly Ser Arg Asp Ser Thr Pro Ser Arg
                2300                2305                2310

CCT GCC CAG CAA CCA TTA AGT AGA CCT ATA CAG TCT CCT GGC CGA AAC     7014
Pro Ala Gln Gln Pro Leu Ser Arg Pro Ile Gln Ser Pro Gly Arg Asn
            2315                2320                2325

TCA ATT TCC CCT GGT AGA AAT GGA ATA AGT CCT CCT AAC AAA TTA TCT     7062
Ser Ile Ser Pro Gly Arg Asn Gly Ile Ser Pro Pro Asn Lys Leu Ser
        2330                2335                2340

CAA CTT CCA AGG ACA TCA TCC CCT AGT ACT GCT TCA ACT AAG TCC TCA     7110
Gln Leu Pro Arg Thr Ser Ser Pro Ser Thr Ala Ser Thr Lys Ser Ser
    2345                2350                2355

GGT TCT GGA AAA ATG TCA TAT ACA TCT CCA GGT AGA CAG ATG AGC CAA     7158
Gly Ser Gly Lys Met Ser Tyr Thr Ser Pro Gly Arg Gln Met Ser Gln
2360                2365                2370                2375

CAG AAC CTT ACC AAA CAA ACA GGT TTA TCC AAG AAT GCC AGT AGT ATT     7206
Gln Asn Leu Thr Lys Gln Thr Gly Leu Ser Lys Asn Ala Ser Ser Ile
                2380                2385                2390

CCA AGA AGT GAG TCT GCC TCC AAA GGA CTA AAT CAG ATG AAT AAT GGT     7254
Pro Arg Ser Glu Ser Ala Ser Lys Gly Leu Asn Gln Met Asn Asn Gly
            2395                2400                2405

AAT GGA GCC AAT AAA AAG GTA GAA CTT TCT AGA ATG TCT TCA ACT AAA     7302
Asn Gly Ala Asn Lys Lys Val Glu Leu Ser Arg Met Ser Ser Thr Lys
        2410                2415                2420

TCA AGT GGA AGT GAA TCT GAT AGA TCA GAA AGA CCT GTA TTA GTA CGC     7350
Ser Ser Gly Ser Glu Ser Asp Arg Ser Glu Arg Pro Val Leu Val Arg
    2425                2430                2435

CAG TCA ACT TTC ATC AAA GAA GCT CCA AGC CCA ACC TTA AGA AGA AAA     7398
Gln Ser Thr Phe Ile Lys Glu Ala Pro Ser Pro Thr Leu Arg Arg Lys
2440                2445                2450                2455

TTG GAG GAA TCT GCT TCA TTT GAA TCT CTT TCT CCA TCA TCT AGA CCA     7446
Leu Glu Glu Ser Ala Ser Phe Glu Ser Leu Ser Pro Ser Ser Arg Pro
                2460                2465                2470

GCT TCT CCC ACT AGG TCC CAG GCA CAA ACT CCA GTT TTA AGT CCT TCC     7494
Ala Ser Pro Thr Arg Ser Gln Ala Gln Thr Pro Val Leu Ser Pro Ser
            2475                2480                2485

CTT CCT GAT ATG TCT CTA TCC ACA CAT TCG TCT GTT CAG GCT GGT GGA     7542
Leu Pro Asp Met Ser Leu Ser Thr His Ser Ser Val Gln Ala Gly Gly
        2490                2495                2500

TGG CGA AAA CTC CCA CCT AAT CTC AGT CCC ACT ATA GAG TAT AAT GAT     7590
Trp Arg Lys Leu Pro Pro Asn Leu Ser Pro Thr Ile Glu Tyr Asn Asp
```

-continued

```
    2505                2510                2515

GGA AGA CCA GCA AAG CGC CAT GAT ATT GCA CGG TCT CAT TCT GAA AGT     7638
Gly Arg Pro Ala Lys Arg His Asp Ile Ala Arg Ser His Ser Glu Ser
2520                2525                2530                2535

CCT TCT AGA CTT CCA ATC AAT AGG TCA GGA ACC TGG AAA CGT GAG CAC     7686
Pro Ser Arg Leu Pro Ile Asn Arg Ser Gly Thr Trp Lys Arg Glu His
                2540                2545                2550

AGC AAA CAT TCA TCA TCC CTT CCT CGA GTA AGC ACT TGG AGA AGA ACT     7734
Ser Lys His Ser Ser Ser Leu Pro Arg Val Ser Thr Trp Arg Arg Thr
            2555                2560                2565

GGA AGT TCA TCT TCA ATT CTT TCT GCT TCA TCA GAA TCC AGT GAA AAA     7782
Gly Ser Ser Ser Ser Ile Leu Ser Ala Ser Ser Glu Ser Ser Glu Lys
        2570                2575                2580

GCA AAA AGT GAG GAT GAA AAA CAT GTG AAC TCT ATT TCA GGA ACC AAA     7830
Ala Lys Ser Glu Asp Glu Lys His Val Asn Ser Ile Ser Gly Thr Lys
    2585                2590                2595

CAA AGT AAA GAA AAC CAA GTA TCC GCA AAA GGA ACA TGG AGA AAA ATA     7878
Gln Ser Lys Glu Asn Gln Val Ser Ala Lys Gly Thr Trp Arg Lys Ile
2600                2605                2610                2615

AAA GAA AAT GAA TTT TCT CCC ACA AAT AGT ACT TCT CAG ACC GTT TCC     7926
Lys Glu Asn Glu Phe Ser Pro Thr Asn Ser Thr Ser Gln Thr Val Ser
                2620                2625                2630

TCA GGT GCT ACA AAT GGT GCT GAA TCA AAG ACT CTA ATT TAT CAA ATG     7974
Ser Gly Ala Thr Asn Gly Ala Glu Ser Lys Thr Leu Ile Tyr Gln Met
            2635                2640                2645

GCA CCT GCT GTT TCT AAA ACA GAG GAT GTT TGG GTG AGA ATT GAG GAC     8022
Ala Pro Ala Val Ser Lys Thr Glu Asp Val Trp Val Arg Ile Glu Asp
        2650                2655                2660

TGT CCC ATT AAC AAT CCT AGA TCT GGA AGA TCT CCC ACA GGT AAT ACT     8070
Cys Pro Ile Asn Asn Pro Arg Ser Gly Arg Ser Pro Thr Gly Asn Thr
    2665                2670                2675

CCC CCG GTG ATT GAC AGT GTT TCA GAA AAG GCA AAT CCA AAC ATT AAA     8118
Pro Pro Val Ile Asp Ser Val Ser Glu Lys Ala Asn Pro Asn Ile Lys
2680                2685                2690                2695

GAT TCA AAA GAT AAT CAG GCA AAA CAA AAT GTG GGT AAT GGC AGT GTT     8166
Asp Ser Lys Asp Asn Gln Ala Lys Gln Asn Val Gly Asn Gly Ser Val
                2700                2705                2710

CCC ATG CGT ACC GTG GGT TTG GAA AAT CGC CTG ACC TCC TTT ATT CAG     8214
Pro Met Arg Thr Val Gly Leu Glu Asn Arg Leu Thr Ser Phe Ile Gln
            2715                2720                2725

GTG GAT GCC CCT GAC CAA AAA GGA ACT GAG ATA AAA CCA GGA CAA AAT     8262
Val Asp Ala Pro Asp Gln Lys Gly Thr Glu Ile Lys Pro Gly Gln Asn
        2730                2735                2740

AAT CCT GTC CCT GTA TCA GAG ACT AAT GAA AGT CCT ATA GTG GAA CGT     8310
Asn Pro Val Pro Val Ser Glu Thr Asn Glu Ser Pro Ile Val Glu Arg
    2745                2750                2755

ACC CCA TTC AGT TCT AGC AGC TCA AGC AAA CAC AGT TCA CCT AGT GGG     8358
Thr Pro Phe Ser Ser Ser Ser Ser Ser Lys His Ser Ser Pro Ser Gly
2760                2765                2770                2775

ACT GTT GCT GCC AGA GTG ACT CCT TTT AAT TAC AAC CCA AGC CCT AGG     8406
Thr Val Ala Ala Arg Val Thr Pro Phe Asn Tyr Asn Pro Ser Pro Arg
                2780                2785                2790

AAA AGC AGC GCA GAT AGC ACT TCA GCT CGG CCA TCT CAG ATC CCA ACT     8454
Lys Ser Ser Ala Asp Ser Thr Ser Ala Arg Pro Ser Gln Ile Pro Thr
            2795                2800                2805

CCA GTG AAT AAC AAC ACA AAG AAG CGA GAT TCC AAA ACT GAC AGC ACA     8502
Pro Val Asn Asn Asn Thr Lys Lys Arg Asp Ser Lys Thr Asp Ser Thr
        2810                2815                2820

GAA TCC AGT GGA ACC CAA AGT CCT AAG CGC CAT TCT GGG TCT TAC CTT     8550
```

-continued

```
Glu Ser Ser Gly Thr Gln Ser Pro Lys Arg His Ser Gly Ser Tyr Leu
    2825                2830                2835

GTG ACA TCT GTT TAAAAGAGAG GAAGAATGAA ACTAAGAAAA TTCTATGTTA         8602
Val Thr Ser Val
2840

ATTACAACTG CTATATAGAC ATTTTGTTTC AAATGAAACT TTAAAAGACT GAAAAATTTT   8662

GTAAATAGGT TTGATTCTTG TTAGAGGGTT TTTGTTCTGG AAGCCATATT TGATAGTATA   8722

CTTTGTCTTC ACTGGTCTTA TTTTGGGAGG CACTCTTGAT GGTTAGGAAA AAATAGAAAG   8782

CCAAGTATGT TTGTACAGTA TGTTTTACAT GTATTTAAAG TAGCATCCCA TCCCAACTTC   8842

CTTAATTATT GCTTGTCTAA AATAATGAAC ACTACAGATA GGAAATATGA TATATTGCTG   8902

TTATCAATCA TTTCTAGATT ATAAACTGAC TAAACTTACA TCAGGGGAAA ATTGGTATTT   8962

ATGCAAAAAA AAAATGTTTT TGTCCTTGTG AGTCCATCTA ACATCATAAT TAATCATGTG   9022

GCTGTGAAAT TCACAGTAAT ATGGTTCCCG ATGAACAAGT TTACCCAGCC TGCTTTGCTT   9082

ACTGCATGAA TGAAACTGAT GGTTCAATTT CAGAAGTAAT GATTAACAGT TATGTGGTCA   9142

CATGATGTGC ATAGAGATAG CTACAGTGTA ATAATTTACA CTATTTTGTG CTCCAAACAA   9202

AACAAAAATC TGTGTAACTG TAAAACATTG AATGAAACTA TTTTACCTGA ACTAGATTTT   9262

ATCTGAAAGT AGGTAGAATT TTTGCTATGC TGTAATTTGT TGTATATTCT GGTATTTGAG   9322

GTGAGATGGC TGCTCTTTAT TAATGAGACA TGAATTGTGT CTCAACAGAA ACTAAATGAA   9382

CATTTCAGAA TAAATTATTG CTGTATGTAA ACTGTTACTG AAATTGGTAT TTGTTTGAAG   9442

GGTTTGTTTC ACATTTGTAT TAATTAATTG TTTAAAATGC CTCTTTTAAA AGCTTATATA   9502

AATTTTTTCT TCAGCTTCTA TGCATTAAGA GTAAAATTCC TCTTACTGTA ATAAAAACAT   9562

TGAAGAAGAC TGTTGCCACT TAACCATTCC ATGCGTTGGC ACTT                    9606
```

(2) INFORMATION FOR SEQ ID NO: 2:

(i) SEQUENCE CHARACTERISTICS:
(A) LENGTH: 2843 amino acids
(B) TYPE: amino acid
(D) TOPOLOGY: linear (ii) MOLECULE TYPE: protein (xi) SEQUENCE DESCRIPTION: SEQ ID NO: 2:

```
Met Ala Ala Ala Ser Tyr Asp Gln Leu Leu Lys Gln Val Glu Ala Leu
  1               5                  10                  15

Lys Met Glu Asn Ser Asn Leu Arg Gln Glu Leu Glu Asp Asn Ser Asn
             20                  25                  30

His Leu Thr Lys Leu Glu Thr Glu Ala Ser Asn Met Lys Glu Val Leu
         35                  40                  45

Lys Gln Leu Gln Gly Ser Ile Glu Asp Glu Ala Met Ala Ser Ser Gly
     50                  55                  60

Gln Ile Asp Leu Leu Glu Arg Leu Lys Glu Leu Asn Leu Asp Ser Ser
 65                  70                  75                  80

Asn Phe Pro Gly Val Lys Leu Arg Ser Lys Met Ser Leu Arg Ser Tyr
                 85                  90                  95

Gly Ser Arg Glu Gly Ser Val Ser Ser Arg Ser Gly Glu Cys Ser Pro
            100                 105                 110

Val Pro Met Gly Ser Phe Pro Arg Arg Gly Phe Val Asn Gly Ser Arg
        115                 120                 125

Glu Ser Thr Gly Tyr Leu Glu Glu Leu Glu Lys Glu Arg Ser Leu Leu
    130                 135                 140
```

-continued

```
Leu Ala Asp Leu Asp Lys Glu Glu Lys Glu Lys Asp Trp Tyr Tyr Ala
145                 150                 155                 160

Gln Leu Gln Asn Leu Thr Lys Arg Ile Asp Ser Leu Pro Leu Thr Glu
                165                 170                 175

Asn Phe Ser Leu Gln Thr Asp Leu Thr Arg Arg Gln Leu Glu Tyr Glu
            180                 185                 190

Ala Arg Gln Ile Arg Val Ala Met Glu Glu Gln Leu Gly Thr Cys Gln
        195                 200                 205

Asp Met Glu Lys Arg Ala Gln Arg Arg Ile Ala Arg Ile Gln Gln Ile
    210                 215                 220

Glu Lys Asp Ile Leu Arg Ile Arg Gln Leu Leu Gln Ser Gln Ala Thr
225                 230                 235                 240

Glu Ala Glu Arg Ser Ser Gln Asn Lys His Glu Thr Gly Ser His Asp
                245                 250                 255

Ala Glu Arg Gln Asn Glu Gly Gln Gly Val Gly Glu Ile Asn Met Ala
            260                 265                 270

Thr Ser Gly Asn Gly Gln Gly Ser Thr Thr Arg Met Asp His Glu Thr
        275                 280                 285

Ala Ser Val Leu Ser Ser Ser Ser Thr His Ser Ala Pro Arg Arg Leu
    290                 295                 300

Thr Ser His Leu Gly Thr Lys Val Glu Met Val Tyr Ser Leu Leu Ser
305                 310                 315                 320

Met Leu Gly Thr His Asp Lys Asp Asp Met Ser Arg Thr Leu Leu Ala
                325                 330                 335

Met Ser Ser Ser Gln Asp Ser Cys Ile Ser Met Arg Gln Ser Gly Cys
            340                 345                 350

Leu Pro Leu Leu Ile Gln Leu Leu His Gly Asn Asp Lys Asp Ser Val
        355                 360                 365

Leu Leu Gly Asn Ser Arg Gly Ser Lys Glu Ala Arg Ala Arg Ala Ser
    370                 375                 380

Ala Ala Leu His Asn Ile Ile His Ser Gln Pro Asp Asp Lys Arg Gly
385                 390                 395                 400

Arg Arg Glu Ile Arg Val Leu His Leu Leu Glu Gln Ile Arg Ala Tyr
                405                 410                 415

Cys Glu Thr Cys Trp Glu Trp Gln Glu Ala His Glu Pro Gly Met Asp
            420                 425                 430

Gln Asp Lys Asn Pro Met Pro Ala Pro Val Glu His Gln Ile Cys Pro
        435                 440                 445

Ala Val Cys Val Leu Met Lys Leu Ser Phe Asp Glu Glu His Arg His
    450                 455                 460

Ala Met Asn Glu Leu Gly Gly Leu Gln Ala Ile Ala Glu Leu Leu Gln
465                 470                 475                 480

Val Asp Cys Glu Met Tyr Gly Leu Thr Asn Asp His Tyr Ser Ile Thr
                485                 490                 495

Leu Arg Arg Tyr Ala Gly Met Ala Leu Thr Asn Leu Thr Phe Gly Asp
            500                 505                 510

Val Ala Asn Lys Ala Thr Leu Cys Ser Met Lys Gly Cys Met Arg Ala
        515                 520                 525

Leu Val Ala Gln Leu Lys Ser Glu Ser Glu Asp Leu Gln Gln Val Ile
    530                 535                 540

Ala Ser Val Leu Arg Asn Leu Ser Trp Arg Ala Asp Val Asn Ser Lys
545                 550                 555                 560
```

-continued

```
Lys Thr Leu Arg Glu Val Gly Ser Val Lys Ala Leu Met Glu Cys Ala
                565                 570                 575

Leu Glu Val Lys Lys Glu Ser Thr Leu Lys Ser Val Leu Ser Ala Leu
            580                 585                 590

Trp Asn Leu Ser Ala His Cys Thr Glu Asn Lys Ala Asp Ile Cys Ala
        595                 600                 605

Val Asp Gly Ala Leu Ala Phe Leu Val Gly Thr Leu Thr Tyr Arg Ser
    610                 615                 620

Gln Thr Asn Thr Leu Ala Ile Ile Glu Ser Gly Gly Gly Ile Leu Arg
625                 630                 635                 640

Asn Val Ser Ser Leu Ile Ala Thr Asn Glu Asp His Arg Gln Ile Leu
                645                 650                 655

Arg Glu Asn Asn Cys Leu Gln Thr Leu Leu Gln His Leu Lys Ser His
            660                 665                 670

Ser Leu Thr Ile Val Ser Asn Ala Cys Gly Thr Leu Trp Asn Leu Ser
        675                 680                 685

Ala Arg Asn Pro Lys Asp Gln Glu Ala Leu Trp Asp Met Gly Ala Val
    690                 695                 700

Ser Met Leu Lys Asn Leu Ile His Ser Lys His Lys Met Ile Ala Met
705                 710                 715                 720

Gly Ser Ala Ala Ala Leu Arg Asn Leu Met Ala Asn Arg Pro Ala Lys
                725                 730                 735

Tyr Lys Asp Ala Asn Ile Met Ser Pro Gly Ser Ser Leu Pro Ser Leu
            740                 745                 750

His Val Arg Lys Gln Lys Ala Leu Glu Ala Glu Leu Asp Ala Gln His
        755                 760                 765

Leu Ser Glu Thr Phe Asp Asn Ile Asp Asn Leu Ser Pro Lys Ala Ser
    770                 775                 780

His Arg Ser Lys Gln Arg His Lys Gln Ser Leu Tyr Gly Asp Tyr Val
785                 790                 795                 800

Phe Asp Thr Asn Arg His Asp Asp Asn Arg Ser Asp Asn Phe Asn Thr
                805                 810                 815

Gly Asn Met Thr Val Leu Ser Pro Tyr Leu Asn Thr Thr Val Leu Pro
            820                 825                 830

Ser Ser Ser Ser Ser Arg Gly Ser Leu Asp Ser Ser Arg Ser Glu Lys
        835                 840                 845

Asp Arg Ser Leu Glu Arg Glu Arg Gly Ile Gly Leu Gly Asn Tyr His
    850                 855                 860

Pro Ala Thr Glu Asn Pro Gly Thr Ser Ser Lys Arg Gly Leu Gln Ile
865                 870                 875                 880

Ser Thr Thr Ala Ala Gln Ile Ala Lys Val Met Glu Glu Val Ser Ala
                885                 890                 895

Ile His Thr Ser Gln Glu Asp Arg Ser Ser Gly Ser Thr Thr Glu Leu
            900                 905                 910

His Cys Val Thr Asp Glu Arg Asn Ala Leu Arg Arg Ser Ser Ala Ala
        915                 920                 925

His Thr His Ser Asn Thr Tyr Asn Phe Thr Lys Ser Glu Asn Ser Asn
    930                 935                 940

Arg Thr Cys Ser Met Pro Tyr Ala Lys Leu Glu Tyr Lys Arg Ser Ser
945                 950                 955                 960

Asn Asp Ser Leu Asn Ser Val Ser Ser Asn Asp Gly Tyr Gly Lys Arg
                965                 970                 975

Gly Gln Met Lys Pro Ser Ile Glu Ser Tyr Ser Glu Asp Asp Glu Ser
```

-continued

```
            980                 985                 990

Lys Phe Cys Ser Tyr Gly Gln Tyr Pro Ala Asp Leu Ala His Lys Ile
        995                 1000                1005

His Ser Ala Asn His Met Asp Asp Asn Asp Gly Glu Leu Asp Thr Pro
    1010                1015                1020

Ile Asn Tyr Ser Leu Lys Tyr Ser Asp Glu Gln Leu Asn Ser Gly Arg
1025                1030                1035                1040

Gln Ser Pro Ser Gln Asn Glu Arg Trp Ala Arg Pro Lys His Ile Ile
                1045                1050                1055

Glu Asp Glu Ile Lys Gln Ser Glu Gln Arg Gln Ser Arg Asn Gln Ser
            1060                1065                1070

Thr Thr Tyr Pro Val Tyr Thr Glu Ser Thr Asp Asp Lys His Leu Lys
        1075                1080                1085

Phe Gln Pro His Phe Gly Gln Gln Glu Cys Val Ser Pro Tyr Arg Ser
    1090                1095                1100

Arg Gly Ala Asn Gly Ser Glu Thr Asn Arg Val Gly Ser Asn His Gly
1105                1110                1115                1120

Ile Asn Gln Asn Val Ser Gln Ser Leu Cys Gln Glu Asp Asp Tyr Glu
                1125                1130                1135

Asp Asp Lys Pro Thr Asn Tyr Ser Glu Arg Tyr Ser Glu Glu Glu Gln
            1140                1145                1150

His Glu Glu Glu Glu Arg Pro Thr Asn Tyr Ser Ile Lys Tyr Asn Glu
        1155                1160                1165

Glu Lys Arg His Val Asp Gln Pro Ile Asp Tyr Ser Leu Lys Tyr Ala
    1170                1175                1180

Thr Asp Ile Pro Ser Ser Gln Lys Gln Ser Phe Ser Phe Ser Lys Ser
1185                1190                1195                1200

Ser Ser Gly Gln Ser Ser Lys Thr Glu His Met Ser Ser Ser Ser Glu
                1205                1210                1215

Asn Thr Ser Thr Pro Ser Ser Asn Ala Lys Arg Gln Asn Gln Leu His
            1220                1225                1230

Pro Ser Ser Ala Gln Ser Arg Ser Gly Gln Pro Gln Lys Ala Ala Thr
        1235                1240                1245

Cys Lys Val Ser Ser Ile Asn Gln Glu Thr Ile Gln Thr Tyr Cys Val
    1250                1255                1260

Glu Asp Thr Pro Ile Cys Phe Ser Arg Cys Ser Ser Leu Ser Ser Leu
1265                1270                1275                1280

Ser Ser Ala Glu Asp Glu Ile Gly Cys Asn Gln Thr Thr Gln Glu Ala
                1285                1290                1295

Asp Ser Ala Asn Thr Leu Gln Ile Ala Glu Ile Lys Gly Lys Ile Gly
            1300                1305                1310

Thr Arg Ser Ala Glu Asp Pro Val Ser Glu Val Pro Ala Val Ser Gln
        1315                1320                1325

His Pro Arg Thr Lys Ser Ser Arg Leu Gln Gly Ser Ser Leu Ser Ser
    1330                1335                1340

Glu Ser Ala Arg His Lys Ala Val Glu Phe Pro Ser Gly Ala Lys Ser
1345                1350                1355                1360

Pro Ser Lys Ser Gly Ala Gln Thr Pro Lys Ser Pro Pro Glu His Tyr
                1365                1370                1375

Val Gln Glu Thr Pro Leu Met Phe Ser Arg Cys Thr Ser Val Ser Ser
            1380                1385                1390

Leu Asp Ser Phe Glu Ser Arg Ser Ile Ala Ser Ser Val Gln Ser Glu
        1395                1400                1405
```

-continued

```
Pro Cys Ser Gly Met Val Ser Gly Ile Ile Ser Pro Ser Asp Leu Pro
    1410                1415                1420

Asp Ser Pro Gly Gln Thr Met Pro Pro Ser Arg Ser Lys Thr Pro Pro
1425                1430                1435                1440

Pro Pro Pro Gln Thr Ala Gln Thr Lys Arg Glu Val Pro Lys Asn Lys
                1445                1450                1455

Ala Pro Thr Ala Glu Lys Arg Glu Ser Gly Pro Lys Gln Ala Ala Val
            1460                1465                1470

Asn Ala Ala Val Gln Arg Val Gln Val Leu Pro Asp Ala Asp Thr Leu
        1475                1480                1485

Leu His Phe Ala Thr Glu Ser Thr Pro Asp Gly Phe Ser Cys Ser Ser
    1490                1495                1500

Ser Leu Ser Ala Leu Ser Leu Asp Glu Pro Phe Ile Gln Lys Asp Val
1505                1510                1515                1520

Glu Leu Arg Ile Met Pro Pro Val Gln Glu Asn Asp Asn Gly Asn Glu
                1525                1530                1535

Thr Glu Ser Glu Gln Pro Lys Glu Ser Asn Glu Asn Gln Glu Lys Glu
            1540                1545                1550

Ala Glu Lys Thr Ile Asp Ser Glu Lys Asp Leu Leu Asp Asp Ser Asp
        1555                1560                1565

Asp Asp Asp Ile Glu Ile Leu Glu Glu Cys Ile Ile Ser Ala Met Pro
    1570                1575                1580

Thr Lys Ser Ser Arg Lys Gly Lys Lys Pro Ala Gln Thr Ala Ser Lys
1585                1590                1595                1600

Leu Pro Pro Pro Val Ala Arg Lys Pro Ser Gln Leu Pro Val Tyr Lys
                1605                1610                1615

Leu Leu Pro Ser Gln Asn Arg Leu Gln Pro Gln Lys His Val Ser Phe
            1620                1625                1630

Thr Pro Gly Asp Asp Met Pro Arg Val Tyr Cys Val Glu Gly Thr Pro
        1635                1640                1645

Ile Asn Phe Ser Thr Ala Thr Ser Leu Ser Asp Leu Thr Ile Glu Ser
    1650                1655                1660

Pro Pro Asn Glu Leu Ala Ala Gly Glu Gly Val Arg Gly Gly Ala Gln
1665                1670                1675                1680

Ser Gly Glu Phe Glu Lys Arg Asp Thr Ile Pro Thr Glu Gly Arg Ser
                1685                1690                1695

Thr Asp Glu Ala Gln Gly Gly Lys Thr Ser Ser Val Thr Ile Pro Glu
            1700                1705                1710

Leu Asp Asp Asn Lys Ala Glu Glu Gly Asp Ile Leu Ala Glu Cys Ile
        1715                1720                1725

Asn Ser Ala Met Pro Lys Gly Lys Ser His Lys Pro Phe Arg Val Lys
    1730                1735                1740

Lys Ile Met Asp Gln Val Gln Gln Ala Ser Ala Ser Ser Ser Ala Pro
1745                1750                1755                1760

Asn Lys Asn Gln Leu Asp Gly Lys Lys Lys Lys Pro Thr Ser Pro Val
                1765                1770                1775

Lys Pro Ile Pro Gln Asn Thr Glu Tyr Arg Thr Arg Val Arg Lys Asn
            1780                1785                1790

Ala Asp Ser Lys Asn Asn Leu Asn Ala Glu Arg Val Phe Ser Asp Asn
        1795                1800                1805

Lys Asp Ser Lys Lys Gln Asn Leu Lys Asn Asn Ser Lys Asp Phe Asn
    1810                1815                1820
```

-continued

```
Asp Lys Leu Pro Asn Asn Glu Asp Arg Val Arg Gly Ser Phe Ala Phe
1825                1830                1835                1840

Asp Ser Pro His His Tyr Thr Pro Ile Glu Gly Thr Pro Tyr Cys Phe
                1845                1850                1855

Ser Arg Asn Asp Ser Leu Ser Ser Leu Asp Phe Asp Asp Asp Asp Val
            1860                1865                1870

Asp Leu Ser Arg Glu Lys Ala Glu Leu Arg Lys Ala Lys Glu Asn Lys
        1875                1880                1885

Glu Ser Glu Ala Lys Val Thr Ser His Thr Glu Leu Thr Ser Asn Gln
    1890                1895                1900

Gln Ser Ala Asn Lys Thr Gln Ala Ile Ala Lys Gln Pro Ile Asn Arg
1905                1910                1915                1920

Gly Gln Pro Lys Pro Ile Leu Gln Lys Gln Ser Thr Phe Pro Gln Ser
                1925                1930                1935

Ser Lys Asp Ile Pro Asp Arg Gly Ala Ala Thr Asp Glu Lys Leu Gln
            1940                1945                1950

Asn Phe Ala Ile Glu Asn Thr Pro Val Cys Phe Ser His Asn Ser Ser
        1955                1960                1965

Leu Ser Ser Leu Ser Asp Ile Asp Gln Glu Asn Asn Asn Lys Glu Asn
    1970                1975                1980

Glu Pro Ile Lys Glu Thr Glu Pro Pro Asp Ser Gln Gly Glu Pro Ser
1985                1990                1995                2000

Lys Pro Gln Ala Ser Gly Tyr Ala Pro Lys Ser Phe His Val Glu Asp
                2005                2010                2015

Thr Pro Val Cys Phe Ser Arg Asn Ser Ser Leu Ser Ser Leu Ser Ile
            2020                2025                2030

Asp Ser Glu Asp Asp Leu Leu Gln Glu Cys Ile Ser Ser Ala Met Pro
        2035                2040                2045

Lys Lys Lys Lys Pro Ser Arg Leu Lys Gly Asp Asn Glu Lys His Ser
    2050                2055                2060

Pro Arg Asn Met Gly Gly Ile Leu Gly Glu Asp Leu Thr Leu Asp Leu
2065                2070                2075                2080

Lys Asp Ile Gln Arg Pro Asp Ser Glu His Gly Leu Ser Pro Asp Ser
                2085                2090                2095

Glu Asn Phe Asp Trp Lys Ala Ile Gln Glu Gly Ala Asn Ser Ile Val
            2100                2105                2110

Ser Ser Leu His Gln Ala Ala Ala Ala Ala Cys Leu Ser Arg Gln Ala
        2115                2120                2125

Ser Ser Asp Ser Asp Ser Ile Leu Ser Leu Lys Ser Gly Ile Ser Leu
    2130                2135                2140

Gly Ser Pro Phe His Leu Thr Pro Asp Gln Glu Glu Lys Pro Phe Thr
2145                2150                2155                2160

Ser Asn Lys Gly Pro Arg Ile Leu Lys Pro Gly Glu Lys Ser Thr Leu
                2165                2170                2175

Glu Thr Lys Lys Ile Glu Ser Glu Ser Lys Gly Ile Lys Gly Gly Lys
            2180                2185                2190

Lys Val Tyr Lys Ser Leu Ile Thr Gly Lys Val Arg Ser Asn Ser Glu
        2195                2200                2205

Ile Ser Gly Gln Met Lys Gln Pro Leu Gln Ala Asn Met Pro Ser Ile
    2210                2215                2220

Ser Arg Gly Arg Thr Met Ile His Ile Pro Gly Val Arg Asn Ser Ser
2225                2230                2235                2240

Ser Ser Thr Ser Pro Val Ser Lys Lys Gly Pro Pro Leu Lys Thr Pro
```

-continued

```
                2245                2250                2255

Ala Ser Lys Ser Pro Ser Glu Gly Gln Thr Ala Thr Thr Ser Pro Arg
            2260                2265                2270

Gly Ala Lys Pro Ser Val Lys Ser Glu Leu Ser Pro Val Ala Arg Gln
        2275                2280                2285

Thr Ser Gln Ile Gly Gly Ser Ser Lys Ala Pro Ser Arg Ser Gly Ser
    2290                2295                2300

Arg Asp Ser Thr Pro Ser Arg Pro Ala Gln Gln Pro Leu Ser Arg Pro
2305                2310                2315                2320

Ile Gln Ser Pro Gly Arg Asn Ser Ile Ser Pro Gly Arg Asn Gly Ile
                2325                2330                2335

Ser Pro Pro Asn Lys Leu Ser Gln Leu Pro Arg Thr Ser Ser Pro Ser
            2340                2345                2350

Thr Ala Ser Thr Lys Ser Ser Gly Ser Gly Lys Met Ser Tyr Thr Ser
        2355                2360                2365

Pro Gly Arg Gln Met Ser Gln Gln Asn Leu Thr Lys Gln Thr Gly Leu
    2370                2375                2380

Ser Lys Asn Ala Ser Ser Ile Pro Arg Ser Glu Ser Ala Ser Lys Gly
2385                2390                2395                2400

Leu Asn Gln Met Asn Asn Gly Asn Gly Ala Asn Lys Lys Val Glu Leu
                2405                2410                2415

Ser Arg Met Ser Ser Thr Lys Ser Ser Gly Ser Glu Ser Asp Arg Ser
            2420                2425                2430

Glu Arg Pro Val Leu Val Arg Gln Ser Thr Phe Ile Lys Glu Ala Pro
        2435                2440                2445

Ser Pro Thr Leu Arg Arg Lys Leu Glu Glu Ser Ala Ser Phe Glu Ser
    2450                2455                2460

Leu Ser Pro Ser Ser Arg Pro Ala Ser Pro Thr Arg Ser Gln Ala Gln
2465                2470                2475                2480

Thr Pro Val Leu Ser Pro Ser Leu Pro Asp Met Ser Leu Ser Thr His
                2485                2490                2495

Ser Ser Val Gln Ala Gly Gly Trp Arg Lys Leu Pro Pro Asn Leu Ser
            2500                2505                2510

Pro Thr Ile Glu Tyr Asn Asp Gly Arg Pro Ala Lys Arg His Asp Ile
        2515                2520                2525

Ala Arg Ser His Ser Glu Ser Pro Ser Arg Leu Pro Ile Asn Arg Ser
    2530                2535                2540

Gly Thr Trp Lys Arg Glu His Ser Lys His Ser Ser Ser Leu Pro Arg
2545                2550                2555                2560

Val Ser Thr Trp Arg Arg Thr Gly Ser Ser Ser Ser Ile Leu Ser Ala
                2565                2570                2575

Ser Ser Glu Ser Ser Glu Lys Ala Lys Ser Glu Asp Glu Lys His Val
            2580                2585                2590

Asn Ser Ile Ser Gly Thr Lys Gln Ser Lys Glu Asn Gln Val Ser Ala
        2595                2600                2605

Lys Gly Thr Trp Arg Lys Ile Lys Glu Asn Glu Phe Ser Pro Thr Asn
    2610                2615                2620

Ser Thr Ser Gln Thr Val Ser Ser Gly Ala Thr Asn Gly Ala Glu Ser
2625                2630                2635                2640

Lys Thr Leu Ile Tyr Gln Met Ala Pro Ala Val Ser Lys Thr Glu Asp
                2645                2650                2655

Val Trp Val Arg Ile Glu Asp Cys Pro Ile Asn Asn Pro Arg Ser Gly
            2660                2665                2670
```

-continued

```
Arg Ser Pro Thr Gly Asn Thr Pro Pro Val Ile Asp Ser Val Ser Glu
        2675                2680                2685

Lys Ala Asn Pro Asn Ile Lys Asp Ser Lys Asp Asn Gln Ala Lys Gln
    2690                2695                2700

Asn Val Gly Asn Gly Ser Val Pro Met Arg Thr Val Gly Leu Glu Asn
2705                2710                2715                2720

Arg Leu Thr Ser Phe Ile Gln Val Asp Ala Pro Asp Gln Lys Gly Thr
                2725                2730                2735

Glu Ile Lys Pro Gly Gln Asn Asn Pro Val Pro Val Ser Glu Thr Asn
            2740                2745                2750

Glu Ser Pro Ile Val Glu Arg Thr Pro Phe Ser Ser Ser Ser Ser Ser
        2755                2760                2765

Lys His Ser Ser Pro Ser Gly Thr Val Ala Ala Arg Val Thr Pro Phe
    2770                2775                2780

Asn Tyr Asn Pro Ser Pro Arg Lys Ser Ser Ala Asp Ser Thr Ser Ala
2785                2790                2795                2800

Arg Pro Ser Gln Ile Pro Thr Pro Val Asn Asn Asn Thr Lys Lys Arg
                2805                2810                2815

Asp Ser Lys Thr Asp Ser Thr Glu Ser Ser Gly Thr Gln Ser Pro Lys
            2820                2825                2830

Arg His Ser Gly Ser Tyr Leu Val Thr Ser Val
        2835                2840
```

(2) INFORMATION FOR SEQ ID NO: 3:

(i) SEQUENCE CHARACTERISTICS:
(A) LENGTH: 3172 base pairs
(B) TYPE: nucleic acid
(C) STRANDEDNESS: double
(D) TOPOLOGY: linear (ii) MOLECULE TYPE: cDNA (vi) ORIGINAL SOURCE:
(A) ORGANISM: Homo sapiens (vii) IMMEDIATE SOURCE:
(B) CLONE: DP1(TB2)

(ix) FEATURE:
(A) NAME/KEY: CDS
(B) LOCATION: 1..630

(xi) SEQUENCE DESCRIPTION: SEQ ID NO: 3:

```
GCA GTC GCC GCT CCA GTC TAT CCG GCA CTA GGA ACA GCC CCG GGN GGC       48
Ala Val Ala Ala Pro Val Tyr Pro Ala Leu Gly Thr Ala Pro Gly Gly
  1               5                  10                  15

GAG ACG GTC CCC GCC ATG TCT GCG GCC ATG AGG GAG AGG TTC GAC CGG       96
Glu Thr Val Pro Ala Met Ser Ala Ala Met Arg Glu Arg Phe Asp Arg
             20                  25                  30

TTC CTG CAC GAG AAG AAC TGC ATG ACT GAC CTT CTG GCC AAG CTC GAG      144
Phe Leu His Glu Lys Asn Cys Met Thr Asp Leu Leu Ala Lys Leu Glu
         35                  40                  45

GCC AAA ACC GGC GTG AAC AGG AGC TTC ATC GCT CTT GGT GTC ATC GGA      192
Ala Lys Thr Gly Val Asn Arg Ser Phe Ile Ala Leu Gly Val Ile Gly
     50                  55                  60

CTG GTG GCC TTG TAC CTG GTG TTC GGT TAT GGA GCC TCT CTC CTC TGC      240
Leu Val Ala Leu Tyr Leu Val Phe Gly Tyr Gly Ala Ser Leu Leu Cys
 65                  70                  75                  80

AAC CTG ATA GGA TTT GGC TAC CCA GCC TAC ATC TCA ATT AAA GCT ATA      288
Asn Leu Ile Gly Phe Gly Tyr Pro Ala Tyr Ile Ser Ile Lys Ala Ile
```

-continued

```
                85                  90                  95

GAG AGT CCC AAC AAA GAA GAT GAT ACC CAG TGG CTG ACC TAC TGG GTA      336
Glu Ser Pro Asn Lys Glu Asp Asp Thr Gln Trp Leu Thr Tyr Trp Val
            100                 105                 110

GTG TAT GGT GTG TTC AGC ATT GCT GAA TTC TTC TCT GAT ATC TTC CTG      384
Val Tyr Gly Val Phe Ser Ile Ala Glu Phe Phe Ser Asp Ile Phe Leu
        115                 120                 125

TCA TGG TTC CCC TTC TAC TAC ATG CTG AAG TGT GGC TTC CTG TTG TGG      432
Ser Trp Phe Pro Phe Tyr Tyr Met Leu Lys Cys Gly Phe Leu Leu Trp
    130                 135                 140

TGC ATG GCC CCG AGC CCT TCT AAT GGG GCT GAA CTG CTC TAC AAG CGC      480
Cys Met Ala Pro Ser Pro Ser Asn Gly Ala Glu Leu Leu Tyr Lys Arg
145                 150                 155                 160

ATC ATC CGT CCT TTC TTC CTG AAG CAC GAG TCC CAG ATG GAC AGT GTG      528
Ile Ile Arg Pro Phe Phe Leu Lys His Glu Ser Gln Met Asp Ser Val
                165                 170                 175

GTC AAG GAC CTT AAA GAC AAG TCC AAA GAG ACT GCA GAT GCC ATC ACT      576
Val Lys Asp Leu Lys Asp Lys Ser Lys Glu Thr Ala Asp Ala Ile Thr
            180                 185                 190

AAA GAA GCG AAG AAA GCT ACC GTG AAT TTA CTG GGT GAA GAA AAG AAG      624
Lys Glu Ala Lys Lys Ala Thr Val Asn Leu Leu Gly Glu Glu Lys Lys
        195                 200                 205

AGC ACC TAAACCAGAC TAAACCAGAC TGGATGGAAA CTTCCTGCCC TCTCTGTACC       680
Ser Thr
    210

TTCCTACTGG AGCTTGATGT TATATTAGGG ACTGTGGTAT AATTATTTTA ATAATGTTGC    740

CTTGGAAACA TTTTTGAGAT ATTAAAGATT GGAATGTGTT GTAAGTTTCT TTGCTTACTT    800

TTACTGTCTA TATATATAGG GAGCACTTTA AACTTAATGC AGTGGGCAGT GTCCACGTTT    860

TTGGAAAATG TATTTTGCCT CTGGGTAGGA AAAGATGTAT GTTGCTATCC TGCAGGAAAT    920

ATAAACTTAA AATAAAATTA TATACCCCAC AGGCTGTGTA CTTTACTGGG CTCTCCCTGC    980

ACGSATTTTC TCTGTAGTTA CATTTAGGRT AATCTTTATG GTTCTACTTC CTRTAATGTA   1040

CAATTTTATA TAATTCNGRA ATGTTTTTAA TGTATTTGTG CACATGTACA TATGGAAATG   1100

TTACTGTCTG ACTACANCAT GCATCATGCT CATGGGGAGG GAGCAGGGGA AGGTTGTATG   1160

TGTCATTTAT AACTTCTGTA CAGTAAGACC ACCTGCCAAA AGCTGGAGGA ACCATTGTGC   1220

TGGTGTGGTC TACTAAATAA TACTTTAGGA AATACGTGAT TAATATGCAA GTGAACAAAG   1280

TGAGAAATGA AATCGAATGG AGATTGGCCT GGTTGTTTCC GTAGTATATG GCATATGAAT   1340

ACCAGGATAG CTTTATAAAG CAGTTAGTTA GTTAGTTACT CACTCTAGTG ATAAATCGGG   1400

AAATTTACAC ACACACACAC ACACACACAC ACACACACAC ACACACACAC ACACACACAG   1460

AGTACCCTGT AACTCTCAAT TCCCTGAAAA ACTAGTAATA CTGTCTTATC TGCTATAAAC   1520

TTTACATATT TGTCTATTGT CAAGATGCTA CANTGGAMNC CATTTCTGGT TTTATCTTCA   1580

NAGSGGAGAN ACATGTTGAT TTAGTCTTCT TTCCCAATCT TCTTTTTTAA MCCAGTTTNA   1640

GGMNCTTCTG RAGATTTGYC CACCTCTGAT TACATGTATG TTCTYGTTTG TATCATKAGC   1700

AACAACATGC TAATGRCGAC ACCTAGCTCT RAGMGCAATT CTGGGAGANT GARAGGNWGT   1760

ATARAGTMNC CCATAATCTG CTTGGCAATA GTTAAGTCAA TCTATCTTCA GTTTTTCTCT   1820

GGCCTTTAAG GTCAAACACA AGAGGCTTCC CTAGTTTACA AGTCAGAGTC ACTTGTAGTC   1880

CATTTAAATG CCCTCATCCG TATTCTTTGT GTTGATAAGC TGCACAKGAC TACATAGTAA   1940

GTACAGANCA GTAAAGTTAA NNCGGATGTC TCCATTGATC TGCCAANTCG NTATAGAGAG   2000

CAATTTGTCT GGACTAGAAA ATCTGAGTTT TACACCATAC TGTTAAGAGT CCTTTTGAAT   2060
```

-continued

```
TAAACTAGAC TAAAACAAGT GTATAACTAA ACTAACAAGA TTAAATATCC AGCCAGTACA   2120

GTATTTTTTA AGGCAAATAA AGATGATTAG CTCACCTTGA GNTAACAATC AGGTAAGATC   2180

ATNACAATGT CTCATGATGT NAANAATATT AAAGATATCA ATACTAAGTG ACAGTATCAC   2240

NNCTAATATA ATATGGATCA GAGCATTTAT TTTGGGGAGG AAAACAGTGG TGATTACCGG   2300

CATTTTATTA AACTTAAAAC TTTGTAGAAA GCAAACAAAA TTGTTCTTGG GAGAAAATCA   2360

ACTTTTAGAT TAAAAAAATT TTAAGTAWCT AGGAGTATTT AAATCCTTTT CCCATAAATA   2420

AAAGTACAGT TTTCTTGGTG GCAGAATGAA AATCAGCAAC NTCTAGCATA TAGACTATAT   2480

AATCAGATTG ACAGCATATA GAATATATTA TCAGACAAGA TGAGGAGGTA CAAAAGTTAC   2540

TATTGCTCAT AATGACTTAC AGGCTAAAAN TAGNTNTAAA ATACTATATT AAATTCTGAA   2600

TGCAATTTTT TTTTGTTCCC TTGAGACCAA AATTTAAGTT AACTGTTGCT GGCAGTCTAA   2660

GTGTAAATGT TAACAGCAGG AGAAGTTAAG AATTGAGCAG TTCTGTTGCA TGATTTCCCA   2720

AATGAAATAC TGCCTTGGCT AGAGTTTGAA AAACTAATTG AGCCTGTGCC TGGCTAGAAA   2780

ACAAGCGTTT ATTTGAATGT GAATAGTGTT TCAAAGGTAT GTAGTTACAG AATTCCTACC   2840

AAACAGCTTA AATTCTTCAA GAAAGAATTC CTGCAGCAGT TATTCCCTTA CCTGAAGGCT   2900

TCAATCATTT GGATCAACAA CTGCTACTCT CGGGAAGACT CCTCTACTCA CAGCTGAAGA   2960

AAATGAGCAC ACCCTTCACA CTGTTATCAC CTATCCTGAA GATGTGATAC ACTGAATGGA   3020

AATAAATAGA TGTAAATAAA ATTGAGWTCT CATTTAAAAA AAACCATGTG CCCAATGGGA   3080

AAATGACCTC ATGTTGTGGT TTAAACAGCA ACTGCACCCA CTAGCACAGC CCATTGAGCT   3140

ANCCTATATA TACATCTCTG TCAGTGCCCC TC                                 3172
```

(2) INFORMATION FOR SEQ ID NO: 4:

(i) SEQUENCE CHARACTERISTICS:
(A) LENGTH: 210 amino acids
(B) TYPE: amino acid
(D) TOPOLOGY: linear (ii) MOLECULE TYPE: protein (xi) SEQUENCE DESCRIPTION: SEQ ID NO: 4:

```
Ala Val Ala Ala Pro Val Tyr Pro Ala Leu Gly Thr Ala Pro Gly Gly
  1               5                  10                  15

Glu Thr Val Pro Ala Met Ser Ala Ala Met Arg Glu Arg Phe Asp Arg
             20                  25                  30

Phe Leu His Glu Lys Asn Cys Met Thr Asp Leu Leu Ala Lys Leu Glu
         35                  40                  45

Ala Lys Thr Gly Val Asn Arg Ser Phe Ile Ala Leu Gly Val Ile Gly
     50                  55                  60

Leu Val Ala Leu Tyr Leu Val Phe Gly Tyr Gly Ala Ser Leu Leu Cys
 65                  70                  75                  80

Asn Leu Ile Gly Phe Gly Tyr Pro Ala Tyr Ile Ser Ile Lys Ala Ile
                 85                  90                  95

Glu Ser Pro Asn Lys Glu Asp Asp Thr Gln Trp Leu Thr Tyr Trp Val
            100                 105                 110

Val Tyr Gly Val Phe Ser Ile Ala Glu Phe Phe Ser Asp Ile Phe Leu
        115                 120                 125

Ser Trp Phe Pro Phe Tyr Tyr Met Leu Lys Cys Gly Phe Leu Leu Trp
    130                 135                 140

Cys Met Ala Pro Ser Pro Ser Asn Gly Ala Glu Leu Leu Tyr Lys Arg
```

-continued

```
145                 150                 155                 160

Ile Ile Arg Pro Phe Phe Leu Lys His Glu Ser Gln Met Asp Ser Val
                165                 170                 175

Val Lys Asp Leu Lys Asp Lys Ser Lys Glu Thr Ala Asp Ala Ile Thr
            180                 185                 190

Lys Glu Ala Lys Lys Ala Thr Val Asn Leu Leu Gly Glu Glu Lys Lys
        195                 200                 205

Ser Thr
    210


(2) INFORMATION FOR SEQ ID NO: 5:

     (i) SEQUENCE CHARACTERISTICS:
          (A) LENGTH: 434 amino acids
          (B) TYPE: amino acid
          (C) STRANDEDNESS: single
          (D) TOPOLOGY: linear

    (ii) MOLECULE TYPE: protein

    (vi) ORIGINAL SOURCE:
          (A) ORGANISM: Homo sapiens

   (vii) IMMEDIATE SOURCE:
          (B) CLONE: TB1

    (xi) SEQUENCE DESCRIPTION: SEQ ID NO: 5:

Val Ala Pro Val Val Val Gly Ser Gly Arg Ala Pro Arg His Pro Ala
1               5                   10                  15

Pro Ala Ala Met His Pro Arg Arg Pro Asp Gly Phe Asp Gly Leu Gly
            20                  25                  30

Tyr Arg Gly Gly Ala Arg Asp Glu Gln Gly Phe Gly Gly Ala Phe Pro
        35                  40                  45

Ala Arg Ser Phe Ser Thr Gly Ser Asp Leu Gly His Trp Val Thr Thr
    50                  55                  60

Pro Pro Asp Ile Pro Gly Ser Arg Asn Leu His Trp Gly Glu Lys Ser
65                  70                  75                  80

Pro Pro Tyr Gly Val Pro Thr Thr Ser Thr Pro Tyr Glu Gly Pro Thr
                85                  90                  95

Glu Glu Pro Phe Ser Ser Gly Gly Gly Gly Ser Val Gln Gly Gln Ser
            100                 105                 110

Ser Glu Gln Leu Asn Arg Phe Ala Gly Phe Gly Ile Gly Leu Ala Ser
        115                 120                 125

Leu Phe Thr Glu Asn Val Leu Ala His Pro Cys Ile Val Leu Arg Arg
    130                 135                 140

Gln Cys Gln Val Asn Tyr His Ala Gln His Tyr His Leu Thr Pro Phe
145                 150                 155                 160

Thr Val Ile Asn Ile Met Tyr Ser Phe Asn Lys Thr Gln Gly Pro Arg
                165                 170                 175

Ala Leu Trp Lys Gly Met Gly Ser Thr Phe Ile Val Gln Gly Val Thr
            180                 185                 190

Leu Gly Ala Glu Gly Ile Ile Ser Glu Phe Thr Pro Leu Pro Arg Glu
        195                 200                 205

Val Leu His Lys Trp Ser Pro Lys Gln Ile Gly Glu His Leu Leu Leu
    210                 215                 220

Lys Ser Leu Thr Tyr Val Val Ala Met Pro Phe Tyr Ser Ala Ser Leu
225                 230                 235                 240

Ile Glu Thr Val Gln Ser Glu Ile Ile Arg Asp Asn Thr Gly Ile Leu
```

-continued

```
                245                 250                 255

Glu Cys Val Lys Glu Gly Ile Gly Arg Val Ile Gly Met Gly Val Pro
            260                 265                 270

His Ser Lys Arg Leu Leu Pro Leu Leu Ser Leu Ile Phe Pro Thr Val
        275                 280                 285

Leu His Gly Val Leu His Tyr Ile Ile Ser Ser Val Ile Gln Lys Phe
    290                 295                 300

Val Leu Leu Ile Leu Lys Arg Lys Thr Tyr Asn Ser His Leu Ala Glu
305                 310                 315                 320

Ser Thr Ser Pro Val Gln Ser Met Leu Asp Ala Tyr Phe Pro Glu Leu
                325                 330                 335

Ile Ala Asn Phe Ala Ala Ser Leu Cys Ser Asp Val Ile Leu Tyr Pro
            340                 345                 350

Leu Glu Thr Val Leu His Arg Leu His Ile Gln Gly Thr Arg Thr Ile
        355                 360                 365

Ile Asp Asn Thr Asp Leu Gly Tyr Glu Val Leu Pro Ile Asn Thr Gln
    370                 375                 380

Tyr Glu Gly Met Arg Asp Cys Ile Asn Thr Ile Arg Gln Glu Glu Gly
385                 390                 395                 400

Val Phe Gly Phe Tyr Lys Gly Phe Gly Ala Val Ile Ile Gln Tyr Thr
                405                 410                 415

Leu His Ala Ala Val Leu Gln Ile Thr Lys Ile Ile Tyr Ser Thr Leu
            420                 425                 430

Leu Gln
```

(2) INFORMATION FOR SEQ ID NO: 6:

(i) SEQUENCE CHARACTERISTICS:
(A) LENGTH: 185 amino acids
(B) TYPE: amino acid
(C) STRANDEDNESS: single
(D) TOPOLOGY: linear (ii) MOLECULE TYPE: protein (vi) ORIGINAL SOURCE:
(A) ORGANISM: Homo sapiens (vii) IMMEDIATE SOURCE:
(B) CLONE: YS-39(TB2)

(xi) SEQUENCE DESCRIPTION: SEQ ID NO: 6:

```
Glu Leu Arg Arg Phe Asp Arg Phe Leu His Glu Lys Asn Cys Met Thr
1               5                   10                  15

Asp Leu Leu Ala Lys Leu Glu Ala Lys Thr Gly Val Asn Arg Ser Phe
            20                  25                  30

Ile Ala Leu Gly Val Ile Gly Leu Val Ala Leu Tyr Leu Val Phe Gly
        35                  40                  45

Tyr Gly Ala Ser Leu Leu Cys Asn Leu Ile Gly Phe Gly Tyr Pro Ala
    50                  55                  60

Tyr Ile Ser Ile Lys Ala Ile Glu Ser Pro Asn Lys Glu Asp Asp Thr
65                  70                  75                  80

Gln Trp Leu Thr Tyr Trp Val Val Tyr Gly Val Phe Ser Ile Ala Glu
                85                  90                  95

Phe Phe Ser Asp Ile Phe Leu Ser Trp Phe Pro Phe Tyr Tyr Ile Leu
            100                 105                 110

Lys Cys Gly Phe Leu Leu Trp Cys Met Ala Pro Ser Pro Ser Asn Gly
        115                 120                 125
```

-continued

```
Ala Glu Leu Leu Tyr Lys Arg Ile Ile Arg Pro Phe Phe Leu Lys His
    130                 135                 140

Glu Ser Gln Met Asp Ser Val Val Lys Asp Leu Lys Asp Lys Ala Lys
145                 150                 155                 160

Glu Thr Ala Asp Ala Ile Thr Lys Glu Ala Lys Lys Ala Thr Val Asn
                165                 170                 175

Leu Leu Gly Glu Glu Lys Lys Ser Thr
            180                 185


(2) INFORMATION FOR SEQ ID NO: 7:

     (i) SEQUENCE CHARACTERISTICS:
          (A) LENGTH: 2843 amino acids
          (B) TYPE: amino acid
          (C) STRANDEDNESS: single
          (D) TOPOLOGY: linear

    (ii) MOLECULE TYPE: protein

    (vi) ORIGINAL SOURCE:
          (A) ORGANISM: Homo sapiens

   (vii) IMMEDIATE SOURCE:
          (B) CLONE: APC

    (xi) SEQUENCE DESCRIPTION: SEQ ID NO: 7:

Met Ala Ala Ala Ser Tyr Asp Gln Leu Leu Lys Gln Val Glu Ala Leu
1               5                   10                  15

Lys Met Glu Asn Ser Asn Leu Arg Gln Glu Leu Glu Asp Asn Ser Asn
            20                  25                  30

His Leu Thr Lys Leu Glu Thr Glu Ala Ser Asn Met Lys Glu Val Leu
        35                  40                  45

Lys Gln Leu Gln Gly Ser Ile Glu Asp Glu Ala Met Ala Ser Ser Gly
    50                  55                  60

Gln Ile Asp Leu Leu Glu Arg Leu Lys Glu Leu Asn Leu Asp Ser Ser
65                  70                  75                  80

Asn Phe Pro Gly Val Lys Leu Arg Ser Lys Met Ser Leu Arg Ser Tyr
                85                  90                  95

Gly Ser Arg Glu Gly Ser Val Ser Ser Arg Ser Gly Glu Cys Ser Pro
            100                 105                 110

Val Pro Met Gly Ser Phe Pro Arg Arg Gly Phe Val Asn Gly Ser Arg
        115                 120                 125

Glu Ser Thr Gly Tyr Leu Glu Glu Leu Glu Lys Glu Arg Ser Leu Leu
    130                 135                 140

Leu Ala Asp Leu Asp Lys Glu Glu Lys Glu Lys Asp Trp Tyr Tyr Ala
145                 150                 155                 160

Gln Leu Gln Asn Leu Thr Lys Arg Ile Asp Ser Leu Pro Leu Thr Glu
                165                 170                 175

Asn Phe Ser Leu Gln Thr Asp Met Thr Arg Arg Gln Leu Glu Tyr Glu
            180                 185                 190

Ala Arg Gln Ile Arg Val Ala Met Glu Glu Gln Leu Gly Thr Cys Gln
        195                 200                 205

Asp Met Glu Lys Arg Ala Gln Arg Arg Ile Ala Arg Ile Gln Gln Ile
    210                 215                 220

Glu Lys Asp Ile Leu Arg Ile Arg Gln Leu Leu Gln Ser Gln Ala Thr
225                 230                 235                 240

Glu Ala Glu Arg Ser Ser Gln Asn Lys His Glu Thr Gly Ser His Asp
                245                 250                 255
```

-continued

```
Ala Glu Arg Gln Asn Glu Gly Gln Gly Val Gly Glu Ile Asn Met Ala
            260                 265                 270

Thr Ser Gly Asn Gly Gln Gly Ser Thr Thr Arg Met Asp His Glu Thr
        275                 280                 285

Ala Ser Val Leu Ser Ser Ser Ser Thr His Ser Ala Pro Arg Arg Leu
    290                 295                 300

Thr Ser His Leu Gly Thr Lys Val Glu Met Val Tyr Ser Leu Leu Ser
305                 310                 315                 320

Met Leu Gly Thr His Asp Lys Asp Asp Met Ser Arg Thr Leu Leu Ala
                325                 330                 335

Met Ser Ser Ser Gln Asp Ser Cys Ile Ser Met Arg Gln Ser Gly Cys
            340                 345                 350

Leu Pro Leu Leu Ile Gln Leu Leu His Gly Asn Asp Lys Asp Ser Val
        355                 360                 365

Leu Leu Gly Asn Ser Arg Gly Ser Lys Glu Ala Arg Ala Arg Ala Ser
    370                 375                 380

Ala Ala Leu His Asn Ile Ile His Ser Gln Pro Asp Asp Lys Arg Gly
385                 390                 395                 400

Arg Arg Glu Ile Arg Val Leu His Leu Leu Glu Gln Ile Arg Ala Tyr
                405                 410                 415

Cys Glu Thr Cys Trp Glu Trp Gln Glu Ala His Glu Pro Gly Met Asp
            420                 425                 430

Gln Asp Lys Asn Pro Met Pro Ala Pro Val Glu His Gln Ile Cys Pro
        435                 440                 445

Ala Val Cys Val Leu Met Lys Leu Ser Phe Asp Glu Glu His Arg His
    450                 455                 460

Ala Met Asn Glu Leu Gly Gly Leu Gln Ala Ile Ala Glu Leu Leu Gln
465                 470                 475                 480

Val Asp Cys Glu Met Tyr Gly Leu Thr Asn Asp His Tyr Ser Ile Thr
                485                 490                 495

Leu Arg Arg Tyr Ala Gly Met Ala Leu Thr Asn Leu Thr Phe Gly Asp
            500                 505                 510

Val Ala Asn Lys Ala Thr Leu Cys Ser Met Lys Gly Cys Met Arg Ala
        515                 520                 525

Leu Val Ala Gln Leu Lys Ser Glu Ser Glu Asp Leu Gln Gln Val Ile
    530                 535                 540

Ala Ser Val Leu Arg Asn Leu Ser Trp Arg Ala Asp Val Asn Ser Lys
545                 550                 555                 560

Lys Thr Leu Arg Glu Val Gly Ser Val Lys Ala Leu Met Glu Cys Ala
                565                 570                 575

Leu Glu Val Lys Lys Glu Ser Thr Leu Lys Ser Val Leu Ser Ala Leu
            580                 585                 590

Trp Asn Leu Ser Ala His Cys Thr Glu Asn Lys Ala Asp Ile Cys Ala
        595                 600                 605

Val Asp Gly Ala Leu Ala Phe Leu Val Gly Thr Leu Thr Tyr Arg Ser
    610                 615                 620

Gln Thr Asn Thr Leu Ala Ile Ile Glu Ser Gly Gly Gly Ile Leu Arg
625                 630                 635                 640

Asn Val Ser Ser Leu Ile Ala Thr Asn Glu Asp His Arg Gln Ile Leu
                645                 650                 655

Arg Glu Asn Asn Cys Leu Gln Thr Leu Leu Gln His Leu Lys Ser His
            660                 665                 670
```

-continued

```
Ser Leu Thr Ile Val Ser Asn Ala Cys Gly Thr Leu Trp Asn Leu Ser
        675                 680                 685

Ala Arg Asn Pro Lys Asp Gln Glu Ala Leu Trp Asp Met Gly Ala Val
    690                 695                 700

Ser Met Leu Lys Asn Leu Ile His Ser Lys His Lys Met Ile Ala Met
705                 710                 715                 720

Gly Ser Ala Ala Ala Leu Arg Asn Leu Met Ala Asn Arg Pro Ala Lys
                725                 730                 735

Tyr Lys Asp Ala Asn Ile Met Ser Pro Gly Ser Ser Leu Pro Ser Leu
            740                 745                 750

His Val Arg Lys Gln Lys Ala Leu Glu Ala Glu Leu Asp Ala Gln His
        755                 760                 765

Leu Ser Glu Thr Phe Asp Asn Ile Asp Asn Leu Ser Pro Lys Ala Ser
    770                 775                 780

His Arg Ser Lys Gln Arg His Lys Gln Ser Leu Tyr Gly Asp Tyr Val
785                 790                 795                 800

Phe Asp Thr Asn Arg His Asp Asp Asn Arg Ser Asp Asn Phe Asn Thr
                805                 810                 815

Gly Asn Met Thr Val Leu Ser Pro Tyr Leu Asn Thr Thr Val Leu Pro
            820                 825                 830

Ser Ser Ser Ser Ser Arg Gly Ser Leu Asp Ser Ser Arg Ser Glu Lys
        835                 840                 845

Asp Arg Ser Leu Glu Arg Glu Arg Gly Ile Gly Leu Gly Asn Tyr His
    850                 855                 860

Pro Ala Thr Glu Asn Pro Gly Thr Ser Ser Lys Arg Gly Leu Gln Ile
865                 870                 875                 880

Ser Thr Thr Ala Ala Gln Ile Ala Lys Val Met Glu Glu Val Ser Ala
                885                 890                 895

Ile His Thr Ser Gln Glu Asp Arg Ser Ser Gly Ser Thr Thr Glu Leu
            900                 905                 910

His Cys Val Thr Asp Glu Arg Asn Ala Leu Arg Arg Ser Ser Ala Ala
        915                 920                 925

His Thr His Ser Asn Thr Tyr Asn Phe Thr Lys Ser Glu Asn Ser Asn
    930                 935                 940

Arg Thr Cys Ser Met Pro Tyr Ala Lys Leu Glu Tyr Lys Arg Ser Ser
945                 950                 955                 960

Asn Asp Ser Leu Asn Ser Val Ser Ser Ser Asp Gly Tyr Gly Lys Arg
                965                 970                 975

Gly Gln Met Lys Pro Ser Ile Glu Ser Tyr Ser Glu Asp Asp Glu Ser
            980                 985                 990

Lys Phe Cys Ser Tyr Gly Gln Tyr Pro Ala Asp Leu Ala His Lys Ile
        995                 1000                1005

His Ser Ala Asn His Met Asp Asp Asn Asp Gly Glu Leu Asp Thr Pro
    1010                1015                1020

Ile Asn Tyr Ser Leu Lys Tyr Ser Asp Glu Gln Leu Asn Ser Gly Arg
1025                1030                1035                1040

Gln Ser Pro Ser Gln Asn Glu Arg Trp Ala Arg Pro Lys His Ile Ile
                1045                1050                1055

Glu Asp Glu Ile Lys Gln Ser Glu Gln Arg Gln Ser Arg Asn Gln Ser
            1060                1065                1070

Thr Thr Tyr Pro Val Tyr Thr Glu Ser Thr Asp Asp Lys His Leu Lys
        1075                1080                1085

Phe Gln Pro His Phe Gly Gln Gln Glu Cys Val Ser Pro Tyr Arg Ser
```

-continued

```
    1090                1095                1100

Arg Gly Ala Asn Gly Ser Glu Thr Asn Arg Val Gly Ser Asn His Gly
1105                1110                1115                1120

Ile Asn Gln Asn Val Ser Gln Ser Leu Cys Gln Glu Asp Asp Tyr Glu
                1125                1130                1135

Asp Asp Lys Pro Thr Asn Tyr Ser Glu Arg Tyr Ser Glu Glu Glu Gln
            1140                1145                1150

His Glu Glu Glu Glu Arg Pro Thr Asn Tyr Ser Ile Lys Tyr Asn Glu
        1155                1160                1165

Glu Lys Arg His Val Asp Gln Pro Ile Asp Tyr Ser Leu Lys Tyr Ala
    1170                1175                1180

Thr Asp Ile Pro Ser Ser Gln Lys Gln Ser Phe Ser Phe Ser Lys Ser
1185                1190                1195                1200

Ser Ser Gly Gln Ser Ser Lys Thr Glu His Met Ser Ser Ser Ser Glu
                1205                1210                1215

Asn Thr Ser Thr Pro Ser Ser Asn Ala Lys Arg Gln Asn Gln Leu His
            1220                1225                1230

Pro Ser Ser Ala Gln Ser Arg Ser Gly Gln Pro Gln Lys Ala Ala Thr
        1235                1240                1245

Cys Lys Val Ser Ser Ile Asn Gln Glu Thr Ile Gln Thr Tyr Cys Val
    1250                1255                1260

Glu Asp Thr Pro Ile Cys Phe Ser Arg Cys Ser Ser Leu Ser Ser Leu
1265                1270                1275                1280

Ser Ser Ala Glu Asp Glu Ile Gly Cys Asn Gln Thr Thr Gln Glu Ala
                1285                1290                1295

Asp Ser Ala Asn Thr Leu Gln Ile Ala Glu Ile Lys Glu Lys Ile Gly
            1300                1305                1310

Thr Arg Ser Ala Glu Asp Pro Val Ser Glu Val Pro Ala Val Ser Gln
        1315                1320                1325

His Pro Arg Thr Lys Ser Ser Arg Leu Gln Gly Ser Ser Leu Ser Ser
    1330                1335                1340

Glu Ser Ala Arg His Lys Ala Val Glu Phe Ser Ser Gly Ala Lys Ser
1345                1350                1355                1360

Pro Ser Lys Ser Gly Ala Gln Thr Pro Lys Ser Pro Pro Glu His Tyr
                1365                1370                1375

Val Gln Glu Thr Pro Leu Met Phe Ser Arg Cys Thr Ser Val Ser Ser
            1380                1385                1390

Leu Asp Ser Phe Glu Ser Arg Ser Ile Ala Ser Ser Val Gln Ser Glu
        1395                1400                1405

Pro Cys Ser Gly Met Val Ser Gly Ile Ile Ser Pro Ser Asp Leu Pro
    1410                1415                1420

Asp Ser Pro Gly Gln Thr Met Pro Pro Ser Arg Ser Lys Thr Pro Pro
1425                1430                1435                1440

Pro Pro Pro Gln Thr Ala Gln Thr Lys Arg Glu Val Pro Lys Asn Lys
                1445                1450                1455

Ala Pro Thr Ala Glu Lys Arg Glu Ser Gly Pro Lys Gln Ala Ala Val
            1460                1465                1470

Asn Ala Ala Val Gln Arg Val Gln Val Leu Pro Asp Ala Asp Thr Leu
        1475                1480                1485

Leu His Phe Ala Thr Glu Ser Thr Pro Asp Gly Phe Ser Cys Ser Ser
    1490                1495                1500

Ser Leu Ser Ala Leu Ser Leu Asp Glu Pro Phe Ile Gln Lys Asp Val
1505                1510                1515                1520
```

-continued

```
Glu Leu Arg Ile Met Pro Pro Val Gln Glu Asn Asp Asn Gly Asn Glu
                1525                1530                1535

Thr Glu Ser Glu Gln Pro Lys Glu Ser Asn Glu Asn Gln Glu Lys Glu
            1540                1545                1550

Ala Glu Lys Thr Ile Asp Ser Glu Lys Asp Leu Leu Asp Asp Ser Asp
        1555                1560                1565

Asp Asp Asp Ile Glu Ile Leu Glu Glu Cys Ile Ile Ser Ala Met Pro
    1570                1575                1580

Thr Lys Ser Ser Arg Lys Ala Lys Lys Pro Ala Gln Thr Ala Ser Lys
1585                1590                1595                1600

Leu Pro Pro Pro Val Ala Arg Lys Pro Ser Gln Leu Pro Val Tyr Lys
                1605                1610                1615

Leu Leu Pro Ser Gln Asn Arg Leu Gln Pro Gln Lys His Val Ser Phe
            1620                1625                1630

Thr Pro Gly Asp Asp Met Pro Arg Val Tyr Cys Val Glu Gly Thr Pro
        1635                1640                1645

Ile Asn Phe Ser Thr Ala Thr Ser Leu Ser Asp Leu Thr Ile Glu Ser
    1650                1655                1660

Pro Pro Asn Glu Leu Ala Ala Gly Glu Gly Val Arg Gly Gly Ala Gln
1665                1670                1675                1680

Ser Gly Glu Phe Glu Lys Arg Asp Thr Ile Pro Thr Glu Gly Arg Ser
                1685                1690                1695

Thr Asp Glu Ala Gln Gly Gly Lys Thr Ser Ser Val Thr Ile Pro Glu
            1700                1705                1710

Leu Asp Asp Asn Lys Ala Glu Glu Gly Asp Ile Leu Ala Glu Cys Ile
        1715                1720                1725

Asn Ser Ala Met Pro Lys Gly Lys Ser His Lys Pro Phe Arg Val Lys
    1730                1735                1740

Lys Ile Met Asp Gln Val Gln Gln Ala Ser Ala Ser Ser Ser Ala Pro
1745                1750                1755                1760

Asn Lys Asn Gln Leu Asp Gly Lys Lys Lys Lys Pro Thr Ser Pro Val
                1765                1770                1775

Lys Pro Ile Pro Gln Asn Thr Glu Tyr Arg Thr Arg Val Arg Lys Asn
            1780                1785                1790

Ala Asp Ser Lys Asn Asn Leu Asn Ala Glu Arg Val Phe Ser Asp Asn
        1795                1800                1805

Lys Asp Ser Lys Lys Gln Asn Leu Lys Asn Asn Ser Lys Asp Phe Asn
    1810                1815                1820

Asp Lys Leu Pro Asn Asn Glu Asp Arg Val Arg Gly Ser Phe Ala Phe
1825                1830                1835                1840

Asp Ser Pro His His Tyr Thr Pro Ile Glu Gly Thr Pro Tyr Cys Phe
                1845                1850                1855

Ser Arg Asn Asp Ser Leu Ser Ser Leu Asp Phe Asp Asp Asp Asp Val
            1860                1865                1870

Asp Leu Ser Arg Glu Lys Ala Glu Leu Arg Lys Ala Lys Glu Asn Lys
        1875                1880                1885

Glu Ser Glu Ala Lys Val Thr Ser His Thr Glu Leu Thr Ser Asn Gln
    1890                1895                1900

Gln Ser Ala Asn Lys Thr Gln Ala Ile Ala Lys Gln Pro Ile Asn Arg
1905                1910                1915                1920

Gly Gln Pro Lys Pro Ile Leu Gln Lys Gln Ser Thr Phe Pro Gln Ser
                1925                1930                1935
```

-continued

```
Ser Lys Asp Ile Pro Asp Arg Gly Ala Ala Thr Asp Glu Lys Leu Gln
            1940                1945                1950

Asn Phe Ala Ile Glu Asn Thr Pro Val Cys Phe Ser His Asn Ser Ser
        1955                1960                1965

Leu Ser Ser Leu Ser Asp Ile Asp Gln Glu Asn Asn Asn Lys Glu Asn
    1970                1975                1980

Glu Pro Ile Lys Glu Thr Glu Pro Pro Asp Ser Gln Gly Glu Pro Ser
1985                1990                1995                2000

Lys Pro Gln Ala Ser Gly Tyr Ala Pro Lys Ser Phe His Val Glu Asp
                2005                2010                2015

Thr Pro Val Cys Phe Ser Arg Asn Ser Ser Leu Ser Ser Leu Ser Ile
            2020                2025                2030

er Glu Asp Asp Leu Leu Gln Glu Cys Ile Ser Ser Ala Met Pro
   2035                2040                2045

ys Lys Lys Pro Ser Arg Leu Lys Gly Asp Asn Glu Lys His Ser
050                2055                2060

rg Asn Met Gly Gly Ile Leu Gly Glu Asp Leu Thr Leu Asp Leu
               2070                2075                2080

sp Ile Gln Arg Pro Asp Ser Glu His Gly Leu Ser Pro Asp Ser
           2085                2090                2095

sn Phe Asp Trp Lys Ala Ile Gln Glu Gly Ala Asn Ser Ile Val
       2100                2105                2110

er Leu His Gln Ala Ala Ala Ala Ala Cys Leu Ser Arg Gln Ala
   2115                2120                2125

er Asp Ser Asp Ser Ile Leu Ser Leu Lys Ser Gly Ile Ser Leu
130                2135                2140

er Pro Phe His Leu Thr Pro Asp Gln Glu Glu Lys Pro Phe Thr
               2150                2155                2160

sn Lys Gly Pro Arg Ile Leu Lys Pro Gly Glu Lys Ser Thr Leu
           2165                2170                2175

hr Lys Lys Ile Glu Ser Glu Ser Lys Gly Ile Lys Gly Gly Lys
       2180                2185                2190

al Tyr Lys Ser Leu Ile Thr Gly Lys Val Arg Ser Asn Ser Glu
   2195                2200                2205

er Gly Gln Met Lys Gln Pro Leu Gln Ala Asn Met Pro Ser Ile
210                2215                2220

rg Gly Arg Thr Met Ile His Ile Pro Gly Val Arg Asn Ser Ser
               2230                2235                2240

er Thr Ser Pro Val Ser Lys Lys Gly Pro Pro Leu Lys Thr Pro
           2245                2250                2255

er Lys Ser Pro Ser Glu Gly Gln Thr Ala Thr Thr Ser Pro Arg
       2260                2265                2270

la Lys Pro Ser Val Lys Ser Glu Leu Ser Pro Val Ala Arg Gln
   2275                2280                2285

er Gln Ile Gly Gly Ser Ser Lys Ala Pro Ser Arg Ser Gly Ser
290                2295                2300

sp Ser Thr Pro Ser Arg Pro Ala Gln Gln Pro Leu Ser Arg Pro
               2310                2315                2320

ln Ser Pro Gly Arg Asn Ser Ile Ser Pro Gly Arg Asn Gly Ile
           2325                2330                2335

ro Pro Asn Lys Leu Ser Gln Leu Pro Arg Thr Ser Ser Pro Ser
       2340                2345                2350

la Ser Thr Lys Ser Ser Gly Ser Gly Lys Met Ser Tyr Thr Ser
```

-continued

```
   2355                2360                2365

ly Arg Gln Met Ser Gln Gln Asn Leu Thr Lys Gln Thr Gly Leu
370                 2375                2380

ys Asn Ala Ser Ser Ile Pro Arg Ser Glu Ser Ala Ser Lys Gly
                2390                2395                2400

sn Gln Met Asn Asn Gly Asn Gly Ala Asn Lys Lys Val Glu Leu
            2405                2410                2415

rg Met Ser Ser Thr Lys Ser Ser Gly Ser Glu Ser Asp Arg Ser
        2420                2425                2430

rg Pro Val Leu Val Arg Gln Ser Thr Phe Ile Lys Glu Ala Pro
   2435                2440                2445

ro Thr Leu Arg Arg Lys Leu Glu Glu Ser Ala Ser Phe Glu Ser
450                 2455                2460

er Pro Ser Ser Arg Pro Ala Ser Pro Thr Arg Ser Gln Ala Gln
                2470                2475                2480

ro Val Leu Ser Pro Ser Leu Pro Asp Met Ser Leu Ser Thr His
            2485                2490                2495

er Val Gln Ala Gly Gly Trp Arg Lys Leu Pro Pro Asn Leu Ser
        2500                2505                2510

hr Ile Glu Tyr Asn Asp Gly Arg Pro Ala Lys Arg His Asp Ile
   2515                2520                2525

rg Ser His Ser Glu Ser Pro Ser Arg Leu Pro Ile Asn Arg Ser
530                 2535                2540

hr Trp Lys Arg Glu His Ser Lys His Ser Ser Ser Leu Pro Arg
                2550                2555                2560

er Thr Trp Arg Arg Thr Gly Ser Ser Ser Ser Ile Leu Ser Ala
            2565                2570                2575

er Glu Ser Ser Glu Lys Ala Lys Ser Glu Asp Glu Lys His Val
        2580                2585                2590

er Ile Ser Gly Thr Lys Gln Ser Lys Glu Asn Gln Val Ser Ala
   2595                2600                2605

ly Thr Trp Arg Lys Ile Lys Glu Asn Glu Phe Ser Pro Thr Asn
610                 2615                2620

hr Ser Gln Thr Val Ser Ser Gly Ala Thr Asn Gly Ala Glu Ser
                2630                2635                2640

hr Leu Ile Tyr Gln Met Ala Pro Ala Val Ser Lys Thr Glu Asp
            2645                2650                2655

rp Val Arg Ile Glu Asp Cys Pro Ile Asn Asn Pro Arg Ser Gly
        2660                2665                2670

er Pro Thr Gly Asn Thr Pro Pro Val Ile Asp Ser Val Ser Glu
   2675                2680                2685

la Asn Pro Asn Ile Lys Asp Ser Lys Asp Asn Gln Ala Lys Gln
690                 2695                2700

al Gly Asn Gly Ser Val Pro Met Arg Thr Val Gly Leu Glu Asn
                2710                2715                2720

eu Asn Ser Phe Ile Gln Val Asp Ala Pro Asp Gln Lys Gly Thr
            2725                2730                2735

le Lys Pro Gly Gln Asn Asn Pro Val Pro Val Ser Glu Thr Asn
        2740                2745                2750

er Ser Ile Val Glu Arg Thr Pro Phe Ser Ser Ser Ser Ser Ser
   2755                2760                2765

is Ser Ser Pro Ser Gly Thr Val Ala Ala Arg Val Thr Pro Phe
770                 2775                2780
```

-continued

```
yr Asn Pro Ser Pro Arg Lys Ser Ser Ala Asp Ser Thr Ser Ala
               2790                2795                2800

ro Ser Gln Ile Pro Thr Pro Val Asn Asn Asn Thr Lys Lys Arg
           2805                2810                2815

er Lys Thr Asp Ser Thr Glu Ser Ser Gly Thr Gln Ser Pro Lys
       2820                2825                2830

is Ser Gly Ser Tyr Leu Val Thr Ser Val
   2835                2840


ATION FOR SEQ ID NO: 8:

EQUENCE CHARACTERISTICS:
(A) LENGTH: 31 amino acids
(B) TYPE: amino acid
(D) TOPOLOGY: linear

OLECULE TYPE: peptide

MMEDIATE SOURCE:
(B) CLONE: ral2(yeast)

i) SEQUENCE DESCRIPTION: SEQ ID NO: 8:

Leu Thr Gly Ala Lys Gly Leu Gln Leu Arg Ala Leu Arg Arg Ile Ala
1               5                   10                  15

Arg Ile Glu Gln Gly Gly Thr Ala Ile Ser Pro Thr Ser Pro Leu
            20                  25                  30


(2) INFORMATION FOR SEQ ID NO: 9:

     (i) SEQUENCE CHARACTERISTICS:
          (A) LENGTH: 29 amino acids
          (B) TYPE: amino acid
          (D) TOPOLOGY: linear

    (ii) MOLECULE TYPE: peptide

    (vi) ORIGINAL SOURCE:
          (A) ORGANISM: Homo sapiens

   (vii) IMMEDIATE SOURCE:
          (B) CLONE: m3(mAChR)

    (xi) SEQUENCE DESCRIPTION: SEQ ID NO: 9:

Leu Tyr Trp Arg Ile Tyr Lys Glu Thr Glu Lys Arg Thr Lys Glu Leu
1               5                   10                  15

Ala Gly Leu Gln Ala Ser Gly Thr Glu Ala Glu Thr Glu
            20                  25


(2) INFORMATION FOR SEQ ID NO: 10:

     (i) SEQUENCE CHARACTERISTICS:
          (A) LENGTH: 29 amino acids
          (B) TYPE: amino acid
          (D) TOPOLOGY: linear

    (ii) MOLECULE TYPE: peptide

    (vi) ORIGINAL SOURCE:
          (A) ORGANISM: Homo sapiens

   (vii) IMMEDIATE SOURCE:
          (B) CLONE: MCC

    (xi) SEQUENCE DESCRIPTION: SEQ ID NO: 10:

Leu Tyr Pro Asn Leu Ala Glu Glu Arg Ser Arg Trp Glu Lys Glu Leu
1               5                   10                  15
```

-continued

```
Ala Gly Leu Arg Glu Glu Asn Glu Ser Leu Thr Ala Met
            20                  25


(2) INFORMATION FOR SEQ ID NO: 11:

     (i) SEQUENCE CHARACTERISTICS:
          (A) LENGTH: 40 base pairs
          (B) TYPE: nucleic acid
          (C) STRANDEDNESS: single
          (D) TOPOLOGY: linear

    (ii) MOLECULE TYPE: cDNA

    (vi) ORIGINAL SOURCE:
          (A) ORGANISM: Homo sapiens

    (xi) SEQUENCE DESCRIPTION: SEQ ID NO: 11:

GTATCAAGAC TGTGACTTTT AATTGTAGTT TATCCATTTT                          40


(2) INFORMATION FOR SEQ ID NO: 12:

     (i) SEQUENCE CHARACTERISTICS:
          (A) LENGTH: 40 base pairs
          (B) TYPE: nucleic acid
          (C) STRANDEDNESS: single
          (D) TOPOLOGY: linear

    (ii) MOLECULE TYPE: cDNA

    (vi) ORIGINAL SOURCE:
          (A) ORGANISM: Homo sapiens

    (xi) SEQUENCE DESCRIPTION: SEQ ID NO: 12:

TTTAGAATTT CATGTTAATA TATTGTGTTC TTTTTAACAG                          40


(2) INFORMATION FOR SEQ ID NO: 13:

     (i) SEQUENCE CHARACTERISTICS:
          (A) LENGTH: 40 base pairs
          (B) TYPE: nucleic acid
          (C) STRANDEDNESS: single
          (D) TOPOLOGY: linear

    (ii) MOLECULE TYPE: cDNA

    (vi) ORIGINAL SOURCE:
          (A) ORGANISM: Homo sapiens

    (xi) SEQUENCE DESCRIPTION: SEQ ID NO: 13:

GTAGATTTTA AAAAGGTGTT TTAAAATAAT TTTTTAAGCT                          40


(2) INFORMATION FOR SEQ ID NO: 14:

     (i) SEQUENCE CHARACTERISTICS:
          (A) LENGTH: 40 base pairs
          (B) TYPE: nucleic acid
          (C) STRANDEDNESS: single
          (D) TOPOLOGY: linear

    (ii) MOLECULE TYPE: cDNA

    (vi) ORIGINAL SOURCE:
          (A) ORGANISM: Homo sapiens

    (xi) SEQUENCE DESCRIPTION: SEQ ID NO: 14:

AAGCAATTGT TGTATAAAAA CTTGTTTCTA TTTTATTTAG                          40


(2) INFORMATION FOR SEQ ID NO: 15:

     (i) SEQUENCE CHARACTERISTICS:
```

-continued (A) LENGTH: 40 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 15:

GTAACTTTTC TTCATATAGT AAACATTGCC TTGTGTACTC 40

(2) INFORMATION FOR SEQ ID NO: 16:

(i) SEQUENCE CHARACTERISTICS:
(A) LENGTH: 40 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 16:

NNNNNNNNNN NNNGTCCCTT TTTTTAAAAA AAAAAAATAG 40

(2) INFORMATION FOR SEQ ID NO: 17:

(i) SEQUENCE CHARACTERISTICS:
(A) LENGTH: 40 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 17:

GTAAGTAACT TGGCAGTACA ACTTATTTGA AACTTTAATA 40

(2) INFORMATION FOR SEQ ID NO: 18:

(i) SEQUENCE CHARACTERISTICS:
(A) LENGTH: 40 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 18:

ATACAAGATA TTGATACTTT TTTATTATTT GTGGTTTTAG 40

(2) INFORMATION FOR SEQ ID NO: 19:

(i) SEQUENCE CHARACTERISTICS:
(A) LENGTH: 40 base pairs
(B) TYPE: nucleic acid
(C) STRANDEDNESS: single
(D) TOPOLOGY: linear (ii) MOLECULE TYPE: cDNA -continued (vi) ORIGINAL SOURCE:
(A) ORGANISM: Homo sapiens (xi) SEQUENCE DESCRIPTION: SEQ ID NO: 19:

GTAAGTTACT TGTTTCTAAG TGATAAAACA GYGAAGAGCT 40

(2) INFORMATION FOR SEQ ID NO: 20:

(i) SEQUENCE CHARACTERISTICS:
(A) LENGTH: 40 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 20:

AATAAAAACA TAACTAATTA GGTTTCTTGT TTTATTTTAG 40

(2) INFORMATION FOR SEQ ID NO: 21:

(i) SEQUENCE CHARACTERISTICS:
(A) LENGTH: 40 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 21:

GTTAGTAAAT TSCCTTTTTT GTTTGTGGGT ATAAAAATAG 40

(2) INFORMATION FOR SEQ ID NO: 22:

(i) SEQUENCE CHARACTERISTICS:
(A) LENGTH: 40 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 22:

ACCATTTTTG CATGTACTGA TGTTAACTCC ATCTTAACAG 40

(2) INFORMATION FOR SEQ ID NO: 23:

(i) SEQUENCE CHARACTERISTICS:
(A) LENGTH: 40 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 23:

GTAAATAAAT TATTTTATCA TATTTTTTAA AATTATTTAA 40

(2) INFORMATION FOR SEQ ID NO: 24:

(i) SEQUENCE CHARACTERISTICS:
(A) LENGTH: 64 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 24:

CATGATGTTA TCTGTATTTA CCTATAGTCT AAATTATACC ATCTATAATG TGCTTAATTT 60

TTAG 64

(2) INFORMATION FOR SEQ ID NO: 25:

(i) SEQUENCE CHARACTERISTICS:
(A) LENGTH: 52 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 25:

GTAACAGAAG ATTACAAACC CTGGTCACTA ATGCCATGAC TACTTTGCTA AG 52

(2) INFORMATION FOR SEQ ID NO: 26:

(i) SEQUENCE CHARACTERISTICS:
(A) LENGTH: 46 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 26:

GGATATTAAA GTCGTAATTT TGTTTCTAAA CTCATTTGGC CCACAG 46

(2) INFORMATION FOR SEQ ID NO: 27:

(i) SEQUENCE CHARACTERISTICS:
(A) LENGTH: 40 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 27:

GTATGTTCTC TATAGTGTAC ATCGTAGTGC ATGTTTCAAA 40

(2) INFORMATION FOR SEQ ID NO: 28:

(i) SEQUENCE CHARACTERISTICS:
(A) LENGTH: 56 base pairs

-continued (B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 28:

CATCATTGCT CTTCAAATAA CAAAGCATTA TGGTTTATGT TGATTTTATT TTTCAG 56

(2) INFORMATION FOR SEQ ID NO: 29:

(i) SEQUENCE CHARACTERISTICS:
(A) LENGTH: 43 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 29:

GTAAGACAAA AATGTTTTTT AATGACATAG ACAATTACTG GTG 43

(2) INFORMATION FOR SEQ ID NO: 30:

(i) SEQUENCE CHARACTERISTICS:
(A) LENGTH: 40 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 30:

TTAGATGATT GTCTTTTTCC TCTTGCCCTT TTTAAATTAG 40

(2) INFORMATION FOR SEQ ID NO: 31:

(i) SEQUENCE CHARACTERISTICS:
(A) LENGTH: 44 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 31:

GTATGTTTTT ATAACATGTA TTTCTTAAGA TAGCTCAGGT ATGA 44

(2) INFORMATION FOR SEQ ID NO: 32:

(i) SEQUENCE CHARACTERISTICS:
(A) LENGTH: 54 base pairs
(B) TYPE: nucleic acid
(C) STRANDEDNESS: single
(D) TOPOLOGY: linear (ii) MOLECULE TYPE: cDNA (vi) ORIGINAL SOURCE:

-continued (A) ORGANISM: Homo sapiens (xi) SEQUENCE DESCRIPTION: SEQ ID NO: 32:

GCTTGGCTTC AAGTTGNCTT TTTAATGATC CTCTATTCTG TATTTAATTT ACAG 54

(2) INFORMATION FOR SEQ ID NO: 33:

(i) SEQUENCE CHARACTERISTICS:
(A) LENGTH: 65 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 33:

GTACTATTTA GAATTTCACC TGTTTTTCTT TTTTCTCTTT TTCTTTGAGG CAGGGTCTCA 60

CTCTG 65

(2) INFORMATION FOR SEQ ID NO: 34:

(i) SEQUENCE CHARACTERISTICS:
(A) LENGTH: 52 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 34:

GCAACTAGTA TGATTTTATG TATAAATTAA TCTAAAATTG ATTAATTTCC AG 52

(2) INFORMATION FOR SEQ ID NO: 35:

(i) SEQUENCE CHARACTERISTICS:
(A) LENGTH: 42 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 35:

GTACCTTTGA AAACATTTAG TACTATAATA TGAATTTCAT GT 42

(2) INFORMATION FOR SEQ ID NO: 36:

(i) SEQUENCE CHARACTERISTICS:
(A) LENGTH: 40 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 36:

CCAACTCNAA TTAGATGACC CATATTCAGA AACTTACTAG 40

-continued (2) INFORMATION FOR SEQ ID NO: 37:

(i) SEQUENCE CHARACTERISTICS:
(A) LENGTH: 54 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 37:

GTATATATAG AGTTTTATAT TACTTTTAAA GTACAGAATT CATACTCTCA AAAA 54

(2) INFORMATION FOR SEQ ID NO: 38:

(i) SEQUENCE CHARACTERISTICS:
(A) LENGTH: 41 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 38:

ATTGTGACCT TAATTTTGTG ATCTCTTGAT TTTTATTTCA G 41

(2) INFORMATION FOR SEQ ID NO: 39:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 39:

TCCCCGCCTG CCGCTCTC 18

(2) INFORMATION FOR SEQ ID NO: 40:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 40:

GCAGCGGCGG CTCCCGTG 18

(2) INFORMATION FOR SEQ ID NO: 41:

(i) SEQUENCE CHARACTERISTICS:
(A) LENGTH: 20 base pairs
(B) TYPE: nucleic acid

-continued (C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 41:

GTGAACGGCT CTCATGCTGC 20

(2) INFORMATION FOR SEQ ID NO: 42:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 42:

ACGTGCGGGG AGGAATGGA 19

(2) INFORMATION FOR SEQ ID NO: 43:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 43:

ATGATATCTT ACCAAATGAT ATAC 24

(2) INFORMATION FOR SEQ ID NO: 44:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 44:

TTATTCCTAC TTCTTCTATA CAG 23

(2) INFORMATION FOR SEQ ID NO: 45:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens -continued (xi) SEQUENCE DESCRIPTION: SEQ ID NO: 45:

TACCCATGCT GGCTCTTTTT C 21

(2) INFORMATION FOR SEQ ID NO: 46:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 46:

TGGGGCCATC TTGTTCCTGA 20

(2) INFORMATION FOR SEQ ID NO: 47:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 47:

ACATTAGGCA CAAAGCTTGC AA 22

(2) INFORMATION FOR SEQ ID NO: 48:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 48:

ATCAAGCTCC AGTAAGAAGG TA 22

(2) INFORMATION FOR SEQ ID NO: 49:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 49:

TGCGGCTCCT GGGTTGTTG 19

(2) INFORMATION FOR SEQ ID NO: 50:

-continued (i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 50:

GCCCCTTCCT TTCTGAGGAC 20

(2) INFORMATION FOR SEQ ID NO: 51:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 51:

TTTTCTCCTG CCTCTTACTG C 21

(2) INFORMATION FOR SEQ ID NO: 52:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 52:

ATGACACCCC CCATTCCCTC 20

(2) INFORMATION FOR SEQ ID NO: 53:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 53:

CCACTTAAAG CACATATATT TAGT 24

(2) INFORMATION FOR SEQ ID NO: 54:

(i) SEQUENCE CHARACTERISTICS:
(A) LENGTH: 22 base pairs
(B) TYPE: nucleic acid
(C) STRANDEDNESS: single
(D) TOPOLOGY: linear -continued (ii) MOLECULE TYPE: cDNA (vi) ORIGINAL SOURCE:
(A) ORGANISM: Homo sapiens (xi) SEQUENCE DESCRIPTION: SEQ ID NO: 54:

GTATGGAAAA TAGTGAAGAA CC 22

(2) INFORMATION FOR SEQ ID NO: 55:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 55:

TTCTTAAGTC CTGTTTTTCT TTTG 24

(2) INFORMATION FOR SEQ ID NO: 56:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 56:

TTTAGAACCT TTTTTGTGTT GTG 23

(2) INFORMATION FOR SEQ ID NO: 57:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 57:

CTCAGATTAT ACACTAAGCC TAAC 24

(2) INFORMATION FOR SEQ ID NO: 58:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 58:

-continued

CATGTCTCTT ACAGTAGTAC CA 22

(2) INFORMATION FOR SEQ ID NO: 59:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 59:

AGGTCCAAGG GTAGCCAAGG 20

(2) INFORMATION FOR SEQ ID NO: 60:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 60:

TAAAAATGGA TAAACTACAA TTAAAAG 27

(2) INFORMATION FOR SEQ ID NO: 61:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 61:

AAATACAGAA TCATGTCTTG AAGT 24

(2) INFORMATION FOR SEQ ID NO: 62:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 62:

ACACCTAAAG ATGACAATTT GAG 23

(2) INFORMATION FOR SEQ ID NO: 63:

(i) SEQUENCE CHARACTERISTICS:
(A) LENGTH: 24 base pairs

-continued (B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 63:

TAACTTAGAT AGCAGTAATT TCCC 24

(2) INFORMATION FOR SEQ ID NO: 64:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 64:

ACAATAAACT GGAGTACACA AGG 23

(2) INFORMATION FOR SEQ ID NO: 65:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 65:

ATAGGTCATT GCTTCTTGCT GAT 23

(2) INFORMATION FOR SEQ ID NO: 66:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 66:

TGAATTTTAA TGGATTACCT AGGT 24

(2) INFORMATION FOR SEQ ID NO: 67:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: cDNA (vi) ORIGINAL SOURCE:

-continued (A) ORGANISM: Homo sapiens (xi) SEQUENCE DESCRIPTION: SEQ ID NO: 67:

CTTTTTTTGC TTTTACTGAT TAACG 25

(2) INFORMATION FOR SEQ ID NO: 68:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 68:

TGTAATTCAT TTTATTCCTA ATACCTC 27

(2) INFORMATION FOR SEQ ID NO: 69:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 69:

GGTAGCCATA GTATGATTAT TTCT 24

(2) INFORMATION FOR SEQ ID NO: 70:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 70:

CTACCTATTT TTATACCCAC AAAC 24

(2) INFORMATION FOR SEQ ID NO: 71:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 71:

AAGAAAGCCT ACACCATTTT TGC 23

-continued (2) INFORMATION FOR SEQ ID NO: 72:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 72:

GATCATTCTT AGAACCATCT TGC 23

(2) INFORMATION FOR SEQ ID NO: 73:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 73:

ACCTATAGTC TAAATTATAC CATC 24

(2) INFORMATION FOR SEQ ID NO: 74:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 74:

GTCATGGCAT TAGTGACCAG 20

(2) INFORMATION FOR SEQ ID NO: 75:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 75:

AGTCGTAATT TTGTTTCTAA ACTC 24

(2) INFORMATION FOR SEQ ID NO: 76:

(i) SEQUENCE CHARACTERISTICS:
(A) LENGTH: 21 base pairs
(B) TYPE: nucleic acid
(C) STRANDEDNESS: single
(D) TOPOLOGY: linear -continued (ii) MOLECULE TYPE: cDNA (vi) ORIGINAL SOURCE:
(A) ORGANISM: Homo sapiens (xi) SEQUENCE DESCRIPTION: SEQ ID NO: 76:

TGAAGGACTC GGATTTCACC C 21

(2) INFORMATION FOR SEQ ID NO: 77:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 77:

TCATTCACTC ACAGCCTGAT GAC 23

(2) INFORMATION FOR SEQ ID NO: 78:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 78:

GCTTTGAAAC ATGCACTACG AT 22

(2) INFORMATION FOR SEQ ID NO: 79:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 79:

AAACATCATT GCTCTTCAAA TAAC 24

(2) INFORMATION FOR SEQ ID NO: 80:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 80:

-continued

TACCATGATT TAAAAATCCA CCAG 24

(2) INFORMATION FOR SEQ ID NO: 81:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 81:

GATGATTGTC TTTTTCCTCT TGC 23

(2) INFORMATION FOR SEQ ID NO: 82:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 82:

CTGAGCTATC TTAAGAAATA CATG 24

(2) INFORMATION FOR SEQ ID NO: 83:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 83:

TTTTAAATGA TCCTCTATTC TGTAT 25

(2) INFORMATION FOR SEQ ID NO: 84:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 84:

ACAGAGTCAG ACCCTGCCTC AAAG 24

(2) INFORMATION FOR SEQ ID NO: 85:

(i) SEQUENCE CHARACTERISTICS:

-continued (A) LENGTH: 23 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 85:

TTTCTATTCT TACTGCTAGC ATT 23

(2) INFORMATION FOR SEQ ID NO: 86:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 86:

ATACACAGGT AAGAAATTAG GA 22

(2) INFORMATION FOR SEQ ID NO: 87:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 87:

TAGATGACCC ATATTCTGTT TC 22

(2) INFORMATION FOR SEQ ID NO: 88:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 88:

CAATTAGGTC TTTTTGAGAG TA 22

(2) INFORMATION FOR SEQ ID NO: 89:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: cDNA -continued (vi) ORIGINAL SOURCE:
(A) ORGANISM: Homo sapiens (xi) SEQUENCE DESCRIPTION: SEQ ID NO: 89:

GTTACTGCAT ACACATTGTG AC 22

(2) INFORMATION FOR SEQ ID NO: 90:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 90:

GCTTTTTGTT TCCTAACATG AAG 23

(2) INFORMATION FOR SEQ ID NO: 91:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 91:

TCTCCCACAG GTAATACTCC C 21

(2) INFORMATION FOR SEQ ID NO: 92:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 92:

GCTAGAACTG AATGGGGTAC G 21

(2) INFORMATION FOR SEQ ID NO: 93:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 93:

CAGGACAAAA TAATCCTGTC CC 22

-continued (2) INFORMATION FOR SEQ ID NO: 94:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 94:

ATTTTCTTAG TTTCATTCTT CCTC 24

(2) INFORMATION FOR SEQ ID NO: 95:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 95:

AGAAGGATCC CTTGTGCAGT GTGGA 25

(2) INFORMATION FOR SEQ ID NO: 96:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 96

GACAGGATCC TGAAGCTGAG TTTG 24

(2) INFORMATION FOR SEQ ID NO: 97:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 97:

TCAGAAAGTG CTGAAGAG 18

(2) INFORMATION FOR SEQ ID NO: 98:

(i) SEQUENCE CHARACTERISTICS:
(A) LENGTH: 19 base pairs
(B) TYPE: nucleic acid
(C) STRANDEDNESS: single -continued (D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 98:

GGAATAATTA GGTCTCCAA 19

(2) INFORMATION FOR SEQ ID NO: 99:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 99:

GCAAATCCTA AGAGAGAACA A 21

(2) INFORMATION FOR SEQ ID NO: 100:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 100:

GATGGCAAGC TTGAGCCAG 19

(2) INFORMATION FOR SEQ ID NO: 101:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 101:

GTTCCAGCAG TGTCACAG 18

(2) INFORMATION FOR SEQ ID NO: 102:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens -continued (xi) SEQUENCE DESCRIPTION: SEQ ID NO: 102:

GGGAGATTTC GCTCCTGA 18

(2) INFORMATION FOR SEQ ID NO: 103:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 103:

AGTACAAGGA TGCCAATATT ATG 23

(2) INFORMATION FOR SEQ ID NO: 104:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 104:

ACTTCTATCT TTTTCAGAAC GAG 23

(2) INFORMATION FOR SEQ ID NO: 105:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 105:

ATTTGAATAC TACAGTGTTA CCC 23

(2) INFORMATION FOR SEQ ID NO: 106:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 106:

CTTGTATTCT AATTTGGCAT AAGG 24

(2) INFORMATION FOR SEQ ID NO: 107:

-continued (i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 107:

CTGCCCATAC ACATTCAAAC AC 22

(2) INFORMATION FOR SEQ ID NO: 108:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 108:

TGTTTGCGTC TTGCCCATCT T 21

(2) INFORMATION FOR SEQ ID NO: 109:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 109:

AGTCTTAAAT ATTCAGATGA GCAG 24

(2) INFORMATION FOR SEQ ID NO: 110:

(i) SEQUENCE CHARACTERISTICS:
(A) LENGTH: 26 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 110:

GTTTCTCTTC ATTATATTTT ATGCTA 26

(2) INFORMATION FOR SEQ ID NO: 111:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 111:

AAGCCTACCA ATTATAGTGA ACG 23

(2) INFORMATION FOR SEQ ID NO: 112:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 112:

AGCTGATGAC AAAGATGATA ATC 23

(2) INFORMATION FOR SEQ ID NO: 113:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 113:

AAGAAACAAT ACAGACTTAT TGTG 24

(2) INFORMATION FOR SEQ ID NO: 114:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 114:

ATGAGTGGGG TCTCCTGAAC 20

(2) INFORMATION FOR SEQ ID NO: 115:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 115:

ATCTCCCTCC AAAAGTGGTG C 21

-continued (2) INFORMATION FOR SEQ ID NO: 116:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 116:

TCCATCTGGA GTACTTTCTG TG 22

(2) INFORMATION FOR SEQ ID NO: 117:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 117:

AGTAAATGCT GCAGTTCAGA GG 22

(2) INFORMATION FOR SEQ ID NO: 118:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 118:

CCGTGGCATA TCATCCCCC 19

(2) INFORMATION FOR SEQ ID NO: 119:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 119:

CCCAGACTGC TTCAAAATTA CC 22

(2) INFORMATION FOR SEQ ID NO: 120:

(i) SEQUENCE CHARACTERISTICS:
(A) LENGTH: 21 base pairs
(B) TYPE: nucleic acid

-continued (C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 120:

GAGCCTCATC TGTACTTCTG C 21

(2) INFORMATION FOR SEQ ID NO: 121:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 121:

CCCTCCAAAT GAGTTAGCTG C 21

(2) INFORMATION FOR SEQ ID NO: 122:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 122:

TTGTGGTATA GGTTTTACTG GTG 23

(2) INFORMATION FOR SEQ ID NO: 123:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 123:

ACCCAACAAA AATCAGTTAG ATG 23

(2) INFORMATION FOR SEQ ID NO: 124:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens -continued (xi) SEQUENCE DESCRIPTION: SEQ ID NO: 124:

GTGGCTGGTA ACTTTAGCCT C 21

(2) INFORMATION FOR SEQ ID NO: 125:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 125:

ATGATGTTGA CCTTTCCAGG G 21

(2) INFORMATION FOR SEQ ID NO: 126:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 126:

ATTGTGTAAC TTTTCATCAG TTGC 24

(2) INFORMATION FOR SEQ ID NO: 127:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 127:

AAAGACATAC CAGACAGAGG G 21

(2) INFORMATION FOR SEQ ID NO: 128:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 128:

CTTTTTTGGC ATTGCGGAGC T 21

(2) INFORMATION FOR SEQ ID NO: 129:

-continued (i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 129:

AAGATGACCT GTTGCAGGAA TG 22

(2) INFORMATION FOR SEQ ID NO: 130:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 130:

GAATCAGACC AAGCTTGTCT AGAT 24

(2) INFORMATION FOR SEQ ID NO: 131:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 131:

CAATAGTAAG TAGTTTACAT CAAG 24

(2) INFORMATION FOR SEQ ID NO: 132:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 132:

AAACAGGACT TGTACTGTAG GA 22

(2) INFORMATION FOR SEQ ID NO: 133:

(i) SEQUENCE CHARACTERISTICS:
(A) LENGTH: 21 base pairs
(B) TYPE: nucleic acid
(C) STRANDEDNESS: single
(D) TOPOLOGY: linear -continued (ii) MOLECULE TYPE: cDNA (vi) ORIGINAL SOURCE:
(A) ORGANISM: Homo sapiens (xi) SEQUENCE DESCRIPTION: SEQ ID NO: 133:

CAGCCCCTTC AAGCAAACAT C 21

(2) INFORMATION FOR SEQ ID NO: 134:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 134:

GAGGACTTAT TCCATTTCTA CC 22

(2) INFORMATION FOR SEQ ID NO: 135:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 135:

CAGTCTCCTG GCCGAAACTC 20

(2) INFORMATION FOR SEQ ID NO: 136:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 136:

GTTGACTGGC GTACTAATAC AG 22

(2) INFORMATION FOR SEQ ID NO: 137:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 137:

-continued

TGGTAATGGA GCCAATAAAA AGG 23

(2) INFORMATION FOR SEQ ID NO: 138:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 138:

TGGGACTTTT CGCCATCCAC 20

(2) INFORMATION FOR SEQ ID NO: 139:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 139:

TGTCTCTATC CACACATTCG TC 22

(2) INFORMATION FOR SEQ ID NO: 140:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 140:

ATGTTTTTCA TCCTCACTTT TTGC 24

(2) INFORMATION FOR SEQ ID NO: 141:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 141:

GGAGAAGAAC TGGAAGTTCA TC 22

(2) INFORMATION FOR SEQ ID NO: 142:

(i) SEQUENCE CHARACTERISTICS:
(A) LENGTH: 25 base pairs

-continued (B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 142:

TTGAATCTTT AATGTTTGGA TTTGC 25

(2) INFORMATION FOR SEQ ID NO: 143:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 143:

TCTCCCACAG GTAATACTCC C 21

(2) INFORMATION FOR SEQ ID NO: 144:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 144:

GCTACAACTG AATGGGGTAC G 21

(2) INFORMATION FOR SEQ ID NO: 145:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO: 145:

CAGGACAAAA TAATCCTGTC CC 22

(2) INFORMATION FOR SEQ ID NO: 146:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: cDNA (vi) ORIGINAL SOURCE:

-continued (A) ORGANISM: Homo sapiens (xi) SEQUENCE DESCRIPTION: SEQ ID NO: 146:

ATTTTCTTAC TTTCATTCTT CCTC 24

(2) INFORMATION FOR SEQ ID NO: 147:

(i) SEQUENCE CHARACTERISTICS:
(A) LENGTH: 20 amino acids
(B) TYPE: amino acid
(D) TOPOLOGY: linear (ii) MOLECULE TYPE: protein (vi) ORIGINAL SOURCE:
(A) ORGANISM: Artificial sequence (consensus)

(xi) SEQUENCE DESCRIPTION: SEQ ID NO: 147:

Phe Xaa Val Glu Xaa Thr Pro Xaa Cys Phe Ser Arg Xaa Ser Ser Leu Ser
1 5 10 15

Leu Ser
20

(2) INFORMATION FOR SEQ ID NO: 148:

(i) SEQUENCE CHARACTERISTICS:
(A) LENGTH: 20 amino acids
(B) TYPE: amino acid
(D) TOPOLOGY: linear (ii) MOLECULE TYPE: protein (vi) ORIGINAL SOURCE:
(A) ORGANISM: Homo sapiens (xi) SEQUENCE DESCRIPTION: SEQ ID NO: 148:

Tyr Cys Val Glu Asp Thr Pro Ile Cys Phe Ser Arg Cys Ser Ser Leu
1 5 10 15

Ser Ser Leu Ser
20

(2) INFORMATION FOR SEQ ID NO: 149:

(i) SEQUENCE CHARACTERISTICS:
(A) LENGTH: 20 amino acids
(B) TYPE: amino acid
(D) TOPOLOGY: linear (ii) MOLECULE TYPE: protein (vi) ORIGINAL SOURCE:
(A) ORGANISM: Homo sapiens (xi) SEQUENCE DESCRIPTION: SEQ ID NO: 149:

His Thr Val Gln Glu Thr Pro Leu Met Phe Ser Arg Cys Thr Ser Val
1 5 10 15

Ser Ser Leu Asp
20

(2) INFORMATION FOR SEQ ID NO: 150:

(i) SEQUENCE CHARACTERISTICS:
(A) LENGTH: 20 amino acids
(B) TYPE: amino acid
(D) TOPOLOGY: linear (ii) MOLECULE TYPE: protein -continued (vi) ORIGINAL SOURCE:
(A) ORGANISM: Homo sapiens (xi) SEQUENCE DESCRIPTION: SEQ ID NO: 150:

```
Phe Ala Thr Glu Ser Thr Pro Asp Gly Phe Ser Cys Ser Ser Ser Leu
 1               5                  10                  15

Ser Ala Leu Ser
            20
```

(2) INFORMATION FOR SEQ ID NO: 151:

(i) SEQUENCE CHARACTERISTICS:
(A) LENGTH: 20 amino acids
(B) TYPE: amino acid
(D) TOPOLOGY: linear (ii) MOLECULE TYPE: protein (vi) ORIGINAL SOURCE:
(A) ORGANISM: Homo sapiens (xi) SEQUENCE DESCRIPTION: SEQ ID NO: 151:

```
Tyr Cys Val Glu Gly Thr Pro Ile Asn Phe Ser Thr Ala Thr Ser Leu
 1               5                  10                  15

Ser Asp Leu Thr
            20
```

(2) INFORMATION FOR SEQ ID NO: 152:

(i) SEQUENCE CHARACTERISTICS:
(A) LENGTH: 20 amino acids
(B) TYPE: amino acid
(D) TOPOLOGY: linear (ii) MOLECULE TYPE: protein (vi) ORIGINAL SOURCE:
(A) ORGANISM: Homo sapiens (xi) SEQUENCE DESCRIPTION: SEQ ID NO: 152:

```
Thr Pro Ile Glu Gly Thr Pro Tyr Cys Phe Ser Arg Asn Asp Ser Leu
 1               5                  10                  15

Ser Ser Leu Asp
            20
```

(2) INFORMATION FOR SEQ ID NO: 153:

(i) SEQUENCE CHARACTERISTICS:
(A) LENGTH: 20 amino acids
(B) TYPE: amino acid
(D) TOPOLOGY: linear (ii) MOLECULE TYPE: protein (vi) ORIGINAL SOURCE:
(A) ORGANISM: Homo sapiens (xi) SEQUENCE DESCRIPTION: SEQ ID NO: 153:

```
Phe Ala Ile Glu Asn Thr Pro Val Cys Pro Ser His Asn Ser Ser Leu
 1               5                  10                  15

Ser Ser Leu Ser
            20
```

(2) INFORMATION FOR SEQ ID NO: 154:

(i) SEQUENCE CHARACTERISTICS:
(A) LENGTH: 20 amino acids

-continued

```
          (B) TYPE: amino acid
          (D) TOPOLOGY: linear

    (ii) MOLECULE TYPE: protein

    (vi) ORIGINAL SOURCE:
          (A) ORGANISM: Homo sapiens

    (xi) SEQUENCE DESCRIPTION: SEQ ID NO: 154:

Arg His Val Glu Asp Thr Pro Val Cys Phe Ser Arg Asn Ser Ser Leu
 1               5                  10                  15

Ser Ser Leu Ser
            20
```

We claim:

1. A preparation of antibodies which specifically binds to a human APC (adenomatous polyposis coli) protein having an amino acid sequence as shown in [SEQ ID NO:1, 2, or 7,] *SEQ ID NO:2 or 7* and does not specifically bind to other human proteins.

[2. A preparation of antibodies which specifically binds to a human APC protein which is the product of a mutant allele found in tumor, wherein the antibodies do not specifically bind to other human proteins, and wherein the human APC protein is a mutant form of the amino acid sequence shown in SEQ ID NOS:2 and 7, and the mutant allele is a mutant form of the nucleotide sequence shown in SEQ ID NO:1.]

[3. The preparation of claim 2 wherein the mutant allele contains a mutation selected from the group consisting of mutations at codons 243, 279, 288, 301,331,413,437, 456, 500, 712, and 1338.]

[4. The preparation of claim 2 wherein the mutant allele contains a premature stop codon.]

[5. The preparation of claim 2 wherein the mutant allele contains a missense mutation.]

[6. The preparation of claim 2 wherein the mutant allele contains a frameshift mutation.]

[7. The preparation of claim 2 wherein the mutant allele contains a splice junction mutation.]

[8. The preparation of claim 2 wherein the mutant allele contains an insertion mutation.]

* * * * *